(12) United States Patent
Marbán et al.

(10) Patent No.: US 11,220,687 B2
(45) Date of Patent: *Jan. 11, 2022

(54) EXOSOMES AND MICRO-RIBONUCLEIC ACIDS FOR TISSUE REGENERATION

(71) Applicant: Cedars-Sinai Medical Center, Los Angeles, CA (US)

(72) Inventors: Eduardo Marbán, Los Angeles, CA (US); Ke Cheng, Los Angeles, CA (US); Ahmed Ibrahim, Los Angeles, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/572,101

(22) Filed: Sep. 16, 2019

(65) Prior Publication Data

US 2020/0024604 A1    Jan. 23, 2020

Related U.S. Application Data

(62) Division of application No. 15/790,962, filed on Oct. 23, 2017, now Pat. No. 10,457,942, which is a division of application No. 14/421,355, filed as application No. PCT/US2013/054732 on Aug. 13, 2013, now Pat. No. 9,828,603.

(60) Provisional application No. 61/682,666, filed on Aug. 13, 2012.

(51) Int. Cl.
| | |
|---|---|
| *C12N 15/113* | (2010.01) |
| *C12N 15/11* | (2006.01) |
| *A61K 31/7105* | (2006.01) |
| *A61K 35/34* | (2015.01) |
| *C12N 5/077* | (2010.01) |
| *A61K 47/46* | (2006.01) |
| *A61K 9/00* | (2006.01) |
| *A61K 47/42* | (2017.01) |

(52) U.S. Cl.
CPC ........ *C12N 15/113* (2013.01); *A61K 31/7105* (2013.01); *A61K 35/34* (2013.01); *A61K 47/46* (2013.01); *C12N 5/0657* (2013.01); *C12N 15/111* (2013.01); *A61K 9/0019* (2013.01); *A61K 47/42* (2013.01); *C12N 2310/141* (2013.01); *C12N 2320/30* (2013.01); *C12N 2502/1329* (2013.01); *C12N 2502/28* (2013.01); *Y02A 50/30* (2018.01)

(58) Field of Classification Search
CPC ... C12N 15/113; C12N 5/0657; C12N 15/111; C12N 2502/1329; C12N 2502/28; C12N 2310/141; C12N 2320/30; A61K 47/46; A61K 31/7105; A61K 35/34; A61K 9/0019; A61K 47/42; Y02A 50/30; A61P 9/14; A61P 9/10; A61P 9/00; A61P 43/00; A61P 35/00; A61P 29/00

See application file for complete search history.

(56) References Cited

U.S. PATENT DOCUMENTS

| | | |
|---|---|---|
| 3,470,876 A | 10/1969 | Barchilon |
| 3,964,468 A | 6/1976 | Schulz |
| 4,106,488 A | 8/1978 | Gordon |
| 4,659,839 A | 4/1987 | Nicolotti et al. |
| 4,921,482 A | 5/1990 | Hammerslag et al. |
| 4,960,134 A | 10/1990 | Webster, Jr. |
| 5,028,588 A | 7/1991 | Hoffman et al. |
| 5,052,402 A | 10/1991 | Bencini et al. |
| 5,104,787 A | 4/1992 | Lindstrom et al. |
| 5,175,004 A | 12/1992 | Matsumura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist et al. |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwich et al. |
| 5,618,294 A | 4/1997 | Aust et al. |

(Continued)

FOREIGN PATENT DOCUMENTS

| | | |
|---|---|---|
| CA | 2488346 | 12/2003 |
| CN | 1537646 | 10/2004 |

(Continued)

OTHER PUBLICATIONS

Gallet et al. (European Heart Journal (2017), 38(3): 201-211). (Year: 2017).*

(Continued)

*Primary Examiner* — J. E. Angell

(74) *Attorney, Agent, or Firm* — Knobbe, Martens, Olson & Bear, LLP

(57) ABSTRACT

Several embodiments relate to methods of repairing and/or regenerating damaged or diseased tissue comprising administering to the damaged or diseased tissues compositions comprising exosomes. In several embodiments, the exosomes comprise one or more microRNA that result in alterations in gene or protein expression, which in turn result in improved cell or tissue viability and/or function.

14 Claims, 34 Drawing Sheets

(56) References Cited

U.S. PATENT DOCUMENTS

| | | |
|---|---|---|
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,748 A | 7/1998 | Palmer et al. |
| 5,824,031 A | 10/1998 | Cookston et al. |
| 5,840,502 A | 11/1998 | Van Vlasselaer |
| 5,851,212 A | 12/1998 | Zirps et al. |
| 5,856,155 A | 1/1999 | Li |
| 5,872,109 A | 2/1999 | Akima et al. |
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,153,582 A | 11/2000 | Skelnik |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss et al. |
| 6,866,843 B2 | 3/2005 | Habener et al. |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marbán et al. |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Alt |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa et al. |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,268,619 B2 | 9/2012 | Giacomello et al. |
| 8,562,972 B2 | 10/2013 | Edinger et al. |
| 8,772,030 B2 | 7/2014 | Giacomello et al. |
| 8,846,396 B2 | 9/2014 | Giacomello et al. |
| 8,945,558 B2 | 2/2015 | Kobara |
| 9,249,392 B2 | 2/2016 | Marbán et al. |
| 9,828,603 B2 * | 11/2017 | Marban ................ A61K 47/46 |
| 9,845,457 B2 | 12/2017 | Marbán et al. |
| 9,884,076 B2 | 2/2018 | Kreke et al. |
| 10,457,942 B2 | 10/2019 | Marbán et al. |
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2002/0155101 A1 | 10/2002 | Donahue et al. |
| 2002/0156383 A1 | 10/2002 | Altman et al. |
| 2002/0177772 A1 | 11/2002 | Altman et al. |
| 2003/0054973 A1 | 3/2003 | Anversa |
| 2003/0129221 A1 | 7/2003 | Semple et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0126879 A1 | 7/2004 | Schneider et al. |
| 2004/0136966 A1 | 7/2004 | Anversa et al. |
| 2004/0137621 A1 | 7/2004 | Rosen et al. |
| 2004/0153139 A1 | 8/2004 | Altman |
| 2004/0158313 A1 | 8/2004 | Altman |
| 2004/0168341 A1 | 9/2004 | Petersen et al. |
| 2004/0214182 A1 | 10/2004 | Sharma et al. |
| 2004/0254134 A1 | 12/2004 | Marbán et al. |
| 2005/0031854 A1 | 2/2005 | Lorenz et al. |
| 2005/0058630 A1 | 3/2005 | Harris et al. |
| 2005/0074880 A1 | 4/2005 | Sang et al. |
| 2005/0090732 A1 | 4/2005 | Ivkov |
| 2005/0176620 A1 | 8/2005 | Prestwich et al. |

(56) References Cited

U.S. PATENT DOCUMENTS

| | | |
|---|---|---|
| 2005/0214938 A1 | 9/2005 | Gold et al. |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0205071 A1 | 9/2006 | Hasson et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0239983 A1 | 10/2006 | Anversa |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0020758 A1 | 1/2007 | Giacomello et al. |
| 2007/0048383 A1 | 3/2007 | Helmus |
| 2007/0053839 A1 | 3/2007 | Zhang |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0099268 A1 | 5/2007 | Cohen et al. |
| 2007/0129296 A1 | 6/2007 | Zhou |
| 2007/0134210 A1 | 6/2007 | Heidaran |
| 2007/0142774 A1 | 6/2007 | Rosenman |
| 2007/0166288 A1 | 7/2007 | Murray et al. |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0286848 A1 | 12/2007 | Louis-Georges et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0103536 A1 | 5/2008 | Xiao |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0213812 A1 | 9/2008 | Andrews et al. |
| 2008/0260704 A1 | 10/2008 | Riordan et al. |
| 2008/0267921 A1 | 10/2008 | Marbán et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0011004 A1 | 1/2009 | Lutz et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0099611 A1 | 4/2009 | Sigg et al. |
| 2009/0123366 A1 | 5/2009 | Dobson et al. |
| 2009/0136582 A1 | 5/2009 | Albrecht et al. |
| 2009/0143296 A1 | 6/2009 | Anversa et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0068811 A1 | 3/2010 | Marbán et al. |
| 2010/0081200 A1 | 4/2010 | Rajala et al. |
| 2010/0233216 A1 | 9/2010 | Cantaluppi et al. |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0003008 A1 | 1/2011 | Lim |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0091448 A1 | 4/2011 | Moon et al. |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0177054 A1 | 7/2011 | Gibbings et al. |
| 2011/0256105 A1 | 10/2011 | Marbán et al. |
| 2011/0256621 A1 | 10/2011 | Albrecht et al. |
| 2011/0258716 A1 | 10/2011 | Baltimore et al. |
| 2011/0280834 A1 | 11/2011 | Forrester et al. |
| 2011/0300111 A1 | 12/2011 | White et al. |
| 2011/0300112 A1 | 12/2011 | Marbán et al. |
| 2012/0021019 A1 | 1/2012 | Giacomello et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093879 A1 | 4/2012 | Giacomello et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbán et al. |
| 2012/0258093 A1 | 10/2012 | Butler-Browne et al. |
| 2012/0315252 A1 | 12/2012 | Marbán et al. |
| 2013/0059006 A1 | 3/2013 | Schmuck et al. |
| 2013/0177593 A1 | 7/2013 | Gunn et al. |
| 2013/0189780 A1 | 7/2013 | Shoemaker et al. |
| 2013/0266543 A1 | 10/2013 | Nadal-Ginard |
| 2013/0280205 A1 | 10/2013 | Mozaffari et al. |
| 2013/0288962 A1 | 10/2013 | Anversa et al. |
| 2013/0295060 A1 | 11/2013 | Yang et al. |
| 2013/0309304 A1 | 11/2013 | Nadal-Ginard |
| 2014/0031256 A1 | 1/2014 | Lim |
| 2014/0120066 A1 | 5/2014 | Yeghiazarians et al. |
| 2014/0121171 A1 | 5/2014 | Muñoz-Cánoves et al. |
| 2014/0156200 A1 | 6/2014 | Verhaegh et al. |
| 2014/0235526 A1 | 8/2014 | Srivastava et al. |
| 2014/0275976 A1 | 9/2014 | Moro |
| 2015/0010640 A1 | 1/2015 | Marbán et al. |
| 2015/0140658 A1 | 5/2015 | Kamp et al. |
| 2015/0246030 A1 | 9/2015 | Armer et al. |
| 2015/0273113 A1 | 10/2015 | Marbán et al. |
| 2015/0328263 A1 | 11/2015 | Kaushal |
| 2016/0158291 A1 | 6/2016 | Kreke et al. |
| 2016/0244723 A1 | 8/2016 | Giacomello et al. |
| 2017/0037375 A1 | 2/2017 | Palecek et al. |
| 2017/0049793 A1 | 2/2017 | Moon et al. |
| 2017/0087087 A1 | 3/2017 | Leonard et al. |
| 2017/0290860 A1 | 10/2017 | Marbán et al. |
| 2017/0304368 A1 | 10/2017 | Marbán et al. |

(56) References Cited

U.S. PATENT DOCUMENTS

| | | | |
|---|---|---|---|
| 2018/0100149 A1 | 4/2018 | Marbán et al. |
| 2019/0000888 A1 | 1/2019 | Marbán et al. |
| 2019/0062740 A1 | 2/2019 | Zhu |
| 2019/0160111 A1 | 5/2019 | Marbán et al. |
| 2019/0255119 A1 | 8/2019 | Marbán et al. |
| 2020/0121727 A1 | 4/2020 | Marbán et al. |
| 2020/0316226 A1 | 10/2020 | Marbán et al. |
| 2021/0032598 A1 | 2/2021 | Ibrahim et al. |
| 2021/0085724 A1 | 3/2021 | Marbán et al. |
| 2021/0207145 A1 | 7/2021 | Marbán et al. |

FOREIGN PATENT DOCUMENTS

| | | |
|---|---|---|
| CN | 1772300 | 5/2006 |
| CN | 1785430 | 6/2006 |
| EP | 1 254 952 | 11/2002 |
| EP | 1 857 544 | 11/2007 |
| EP | 1 970 446 | 9/2008 |
| EP | 2 182 053 | 5/2010 |
| EP | 2 228 444 | 9/2010 |
| EP | 1 631 318 | 11/2010 |
| EP | 1 650 293 | 12/2010 |
| EP | 2 371 370 | 10/2011 |
| EP | 2 385 120 | 11/2011 |
| EP | 2 446 929 | 5/2012 |
| EP | 1 945 256 | 7/2012 |
| EP | 2 094 869 | 7/2012 |
| EP | 2 486 944 | 8/2012 |
| EP | 2 277 548 | 1/2013 |
| EP | 2 687 219 | 1/2014 |
| JP | 2005-506845 | 3/2005 |
| JP | 2005-110565 | 4/2005 |
| JP | 2006-006125 | 1/2006 |
| JP | 2008-504816 | 2/2008 |
| JP | 2008-518730 | 6/2008 |
| KR | 100830889 | 5/2008 |
| KR | 10-1818560 | 1/2018 |
| WO | WO 97/005265 | 2/1997 |
| WO | WO 97/012912 | 4/1997 |
| WO | WO 98/004708 | 2/1998 |
| WO | WO 98/032866 | 7/1998 |
| WO | WO 99/011809 | 3/1999 |
| WO | WO 99/039624 | 8/1999 |
| WO | WO 99/049015 | 9/1999 |
| WO | WO 99/051297 | 10/1999 |
| WO | WO 00/009185 | 2/2000 |
| WO | WO 00/024452 | 5/2000 |
| WO | WO 01/010482 | 2/2001 |
| WO | WO 01/026585 | 4/2001 |
| WO | WO 01/026706 | 4/2001 |
| WO | WO 01/026727 | 4/2001 |
| WO | WO 01/048151 | 7/2001 |
| WO | WO 01/076679 | 10/2001 |
| WO | WO 01/076682 | 10/2001 |
| WO | WO 02/009650 | 2/2002 |
| WO | WO 02/013760 | 2/2002 |
| WO | WO 02/051489 | 7/2002 |
| WO | WO 03/004626 | 1/2003 |
| WO | WO 03/006950 | 1/2003 |
| WO | WO 03/008535 | 1/2003 |
| WO | WO 03/049626 | 6/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/007529 | 1/2006 |
| WO | WO 2006/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO 2008/036776 | 3/2008 |
| WO | WO 2008/043521 | 4/2008 |
| WO | WO 2008/058216 | 5/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO 2009/056116 | 5/2009 |
| WO | WO 2009/058818 | 5/2009 |
| WO | WO 2009/062143 | 5/2009 |
| WO | WO 2009/062169 | 5/2009 |
| WO | WO 2009/067644 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/100137 | 8/2009 |
| WO | WO 2009/103818 | 8/2009 |
| WO | WO 2009/149956 | 12/2009 |
| WO | WO 2009/152111 | 12/2009 |
| WO | WO 2010/015665 | 2/2010 |
| WO | WO 2010/028090 | 3/2010 |
| WO | WO 2010/033285 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO 2011/029092 | 3/2011 |
| WO | WO 2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |
| WO | WO 2011/062244 | 5/2011 |
| WO | WO 2011/064354 | 6/2011 |
| WO | WO 2011/084460 | 7/2011 |
| WO | WO 2011/121120 | 10/2011 |
| WO | WO 2011/127625 | 10/2011 |
| WO | WO 2011/138328 | 11/2011 |
| WO | WO 2011/143499 | 11/2011 |
| WO | WO 2012/019103 | 2/2012 |
| WO | WO 2012/020307 | 2/2012 |
| WO | WO 2012/020308 | 2/2012 |
| WO | WO 2012/055971 | 5/2012 |
| WO | WO 2012/065027 | 5/2012 |
| WO | WO 2012/125471 | 9/2012 |
| WO | WO 2012/135253 | 10/2012 |
| WO | WO 2012/149557 | 11/2012 |
| WO | WO 2012/162741 | 12/2012 |
| WO | WO 2013/048734 | 4/2013 |
| WO | WO 2013/170170 | 11/2013 |
| WO | WO 2013/184527 | 12/2013 |
| WO | WO 2014/013258 | 1/2014 |
| WO | WO 2014/028493 | 2/2014 |
| WO | WO 2014/114465 | 7/2014 |
| WO | WO 2014/160153 | 10/2014 |
| WO | WO 2015/055857 | 4/2015 |
| WO | WO 2015/085096 | 6/2015 |
| WO | WO 2015/092020 | 6/2015 |
| WO | WO 2015/120150 | 8/2015 |
| WO | WO 2016/054591 | 4/2016 |
| WO | WO 2016/057560 | 4/2016 |
| WO | WO 2017/160884 | 9/2017 |
| WO | WO 2017/173034 | 10/2017 |
| WO | WO 2019/015702 | 1/2019 |
| WO | WO 2019/028223 | 2/2019 |
| WO | WO 2019/050071 | 3/2019 |
| WO | WO 2019/126068 | 6/2019 |
| WO | WO 2019/152549 | 8/2019 |
| WO | WO 2020/227489 | 11/2020 |
| WO | WO 2021/178514 | 9/2021 |
| WO | WO 2021/188899 | 9/2021 |

OTHER PUBLICATIONS

Abdel-Latif et al., "Adult Bone Marrow-Derived Cells for Cardiac Repair: A Systematic Review and Meta-Analysis", Archives of Internal Medicine, vol. 167, May 28, 2007, pp. 989-997.

(56) References Cited

OTHER PUBLICATIONS

Abela et al., "A New Method for Isolation of Cardiac Myocytes by Percutaneous Endomyocardial Biopsy", Catheterization and Cardiovascular Diagnosis, 1996, vol. 37, pp. 227-230.
Ajijola et al., "Ventricular Tachycardia in Ischemic Heart Disease Substrates", Indian Heart Journal, 2014, pp. S24-S34, S28 & S30, vol. 66, Supplement 1.
Albini et al., "A Rapid in Vitro Assay for Quantitating the Invasive Potential of Tumor Cells", Cancer Research, Jun. 15, 1987, pp. 3239-3245, vol. 47.
Ames et al., "Oxidants, Antioxidants, and the Degenerative Diseases of Aging", Proceedings of the National Academy of Sciences of the United States of America, Sep. 1993, vol. 90, pp. 7915-7922.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.
Andersen et al., "Murine 'Cardiospheres' Are Not a Source of Stem Cells with Cardiomyogenic Potential," Stem Cells, 2009, vol. 27, No. 7, pp. 1571-1581.
Anversa et al., "Primitive Cells and Tissue Regeneration", Circulation Research, 2003, vol. 92, pp. 579-582.
Assmus et al., "Transplantation of Progenitor Cells and Regeneration Enhancement in Acute Myocardial Infarction (TOPCARE-AMI)", Circulation, Dec. 10, 2002, vol. 106, pp. 3009-3017.
"ATS/ACCP Statement on Cardiopulmonary Exercise Testing", American Thoracic Society/American College of Chest Physicians, American Journal of Respiratory and Critical Care Medicine, 2003, vol. 167, pp. 211-277.
Ausma et al., "Dedifferentiation of Atrial Cardiomyocytes: From in Vivo to In Vitro", Cardiovascular Research, Jul. 2002, vol. 55, No. 1, pp. 9-12.
Baker et al. "Adaptation to Culture of Human Embryonic Stem Cells and Oncogenesis in Vivo" Nature Biotechnology, Feb. 2007, vol. 25, No. 2, pp. 207-215.
Balser et al., "Global Parameter Optimization for Cardiac Potassium Channel Gating Models", Biophysical Journal, Mar. 1990, vol. 57, pp. 433-444.
Balser et al., "Local Anesthetics as Effectors of Allosteric Gating", Journal of Clinical Investigation, Dec. 1996, vol. 98, No. 12, pp. 2874-2886.
Barbash et al., "Systemic Delivery of Bone-Marrow-Derived Mesenchymal Stem Cells to the Infarcted Myocardium Feasibility, Cell Migration, and Body Distribution," Circulation, Apr. 19, 2003, vol. 108, pp. 863-868.
Barile et al., "Cardiac Stem Cells: Isolation, Expansion and Experimental use for Myocardial Regeneration", Nature Clinical Practice Cardiovascular Medicine, Feb. 2007, vol. 4, No. 1, pp. S9-S14.
Barile et al., "Endogenous Cardiac Stem Cells", Progress in Cardiovascular Diseases, Jul.-Aug. 2007, vol. 50, No. 1, pp. 31-48.
Barile et al., "Human Cardiospheres as a Source of Multipotent Stem and Progenitor Cells", Hindawi Publishing Corporation, Stem Cells International, 2013, vol. 2013, pp. 10.
Barr et al., "Efficient Catheter-Mediated Gene Transfer Into the Heart Using Replication-Defective Adenovirus", Gene Therapy, Jan. 1994, vol. 1, No. 1, pp. 51-58.
Barry et al., "Differential Expression of Voltage-Gated $K^+$ Channel Subunits in Adult Rat Heart", Circulation Research, 1995, vol. 77, pp. 361-369.
Barth et al., "Lentiviral Vectors Bearing the Cardiac Promoter of the $Na^+$-$Ca^{2+}$ Exchanger Report Cardiogenic Differentiation in Stem Cells", Molecular Therapy, May 2008, vol. 16, No. 5, pp. 957-964.
Bearzi et al., "Human Cardiac Stem Cells", Proceedings of the National Academy of Sciences of the United States of America (PNAS), Aug. 28, 2007, pp. 14068-14073, vol. 104, No. 35.
Beltrami et al., "Adult Cardiac Stem Cells are Multipotent and Support Myocardial Regeneration", Cell, Sep. 19, 2003, vol. 114, No. 6, pp. 763-776.
Beltrami et al., "Evidence That Human Cardiac Myocytes Divide After Myocardial Infarction", The New England Journal of Medicine, Jun. 7, 2001, vol. 344, pp. 1750-1757.
Beltrami et al., "Multipotent Cells Can be Generated In Vitro from Several Adult Human Organs (Heart, Liver and Bone Marrow)", Stem Cells in Hematology, Blood, 2007, pp. 3438-3446, vol. 110, No. 9.
Bénardeau et al., "Primary Culture of Human Atrial Myocytes is Associated with the Appearance of Structural and Functional Characteristics of Immature Myocardium", Journal of Molecular and Cellular Cardiology, 1997, vol. 29, pp. 1307-1320.
Bergmann et al., "Evidence for Cardiomyocyte Renewal in Humans", Science, Apr. 3, 2009, vol. 324, pp. 98-102.
Bernanke et al., "Effects of Hyaluronic Acid on Cardiac Cushion Tissue Cells in Collagen Matrix Cultures", Texas Reports on Biology and Medicine, 1979, pp. 271-285, vol. 39.
"Bioptome.com", Scholten Surgical Instruments, Inc., downloaded from http://www.bioptome.com/pages.php?page=Products, 2001, first date of publication unknown, printed on Nov. 1, 2005, pp. 2.
Bird et al., "The Human Adult Cardiomyocyte Phenotype", Cardiovascular Research, May 1, 2003, vol. 58, No. 2, pp. 423-434.
Birks et al., "Left Ventricular Assist Device and Drug Therapy for the Reversal of Heart Failure", The New England Journal of Medicine, 2006, vol. 355, No. 18, pp. 1873-1884.
Bjelakovic et al., "Mortality in Randomized Trials of Antioxidant Supplements for Primary and Secondary Prevention: Systematic Review and Meta-Analysis", JAMA, 2007, vol. 297, pp. 842-857.
Bosnali et al., "Generation of Transducible Versions of Transcription Factors Oct4 and Sox2", Biological Chemistry, Jul. 2008, vol. 389, pp. 851-861.
Bredemeyer et al., "ATM Stabilizes DNA Double-Strand-Break Complexes During V(D)J Recombination", Nature, Jul. 27, 2006, vol. 442, pp. 466-470.
Burstein et al., "Systemic and Coronary Delivery of Marrow Stromal Cells for Cellular Cardiomyoplasty: Advantages and Precautions", Basic and Applied Myology, 2003, vol. 13, No. 1, pp. 7-10.
Cai et al., "Injectable Glycosaminoglycan Hydrogels for Controlled Release of Human Basic Fibroblast Growth Factor," Biomaterials, 2005, vol. 26, pp. 6054-6067.
Cambier et al., "Y RNA Fragment in Extracellular Vesicles Confers Cardioprotection via Modulation of IL-10 Expression and Secretion", EMBO Molecular Medicine, 2017, vol. 9, No. 3, pp. 337-352.
"CArdiosphere-Derived aUtologous StemCElls to Reverse ventricUlar dySfunction (CADUCEUS)", ClinicalTrials.gov, Identifier NCT00893360, 2009, pp. 6.
Chambers et al., "Functional Expression Cloning of Nanog, a Pluripotency Sustaining Factor in Embryonic Stem Cells", Cell, May 30, 2003, vol. 113, No. 5, pp. 643-655.
Chen et al., "Enhanced Tumorigenesis in p53 Knockout Mice Exposed in Utero to High-Dose Vitamin E", Carcinogenesis, 2006, vol. 27, No. 7, pp. 1358-1368.
Chen et al., "Mesenchymal Stem Cell Secretes Microparticles Enriched in Pre-MicroRNAs", Nucleic Acids Research, 2010, vol. 38, No. 1, pp. 215-224.
Chen et al., "Reduced Tumorigenesis in p53 Knockout Mice Exposed in Utero to Low-Dose Vitamin E", Cancer, Apr. 1, 2009, vol. 115, pp. 1563-1575.
Chen et al., "The Role of Notch 1 Activation in Cardiosphere Derived Cell Differentiation", Stem Cells and Development, 2012, pp. 2122-2129, vol. 21, No. 12.
Chen et al., "Vascular Endothelial Growth Factor Promotes Cardiomyocyte Differentiation of Embryonic Stem Cells", American Journal of Physiology—Heart and Circulatory Physiology, Oct. 2006, vol. 291, No. 4, pp. H1653-H1658.
Cheng et al., "Functional Performance of Human Cardiosphere-Derived Cells Delivered in an in situ Polymerizable Hyaluronan-Gelatin Hydrogel", Biomaterials, 2012, pp. 8.
Cheng et al., "Magnetic Targeting Enhances Engraftment and Functional Benefit of Iron-Labeled Cardiosphere-Derived Cells in Myocardial Infarction", Circulation Research, 2010, pp. 1570-1581, vol. 106.

(56) References Cited

OTHER PUBLICATIONS

Cheng et al., "Relative Roles of CD90 and c-Kit to the Regenerative Efficacy of Cardiosphere-Derived Cells in Humans and in a Mouse Mode of Myocardial Infarction", Journal of the American Heart Association, Oct. 9, 2014, pp. 1-10, vol. 3, No. 5.

Cheng et al., "Transplantation of Platelet Gel Spike with Cardiosphere-Derived Cells Boosts Structural and Functional Benefits Relative to Gel Transplantation Alone in Rats with Myocardial Infarction", Biomaterials, 2012, vol. 33, pp. 2872-2879.

Chimenti et al., "Abstract 3182: Paracrine Contribution versus Direct Regeneration in Cardiosphere-Derived Cell Therapy for Acute Myocardial Infarction", Circulation, 2009, vol. 120, p. S756.

Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.

Chlopčíková et al., "Neonatal Rat Cardiomyocytes—A Model for the Study of Morphological Biochemical and Electrophysiological Characteristics of the Heart", Biomedical Papers, 2001, vol. 145, No. 2, pp. 49-55.

Cho et al., "Secondary Sphere Formation Enhances the Functionality of Cardiac Progenitor Cells", Molecular Therapy, Sep. 2012, vol. 20, No. 9, pp. 1750-1766.

Christman et al., "Biomaterials for the Treatment of Myocardial Infarction", Journal of the American College Of Cardiology, 2006, vol. 48, No. 5, pp. 907-913.

Conkright et al., "A Gene Encoding an Intestinal-Enriched Member of the Krüppel-Like Factor Family Expressed in Intestinal Epithelia Cells", Nucleic Acids Research, 1999, vol. 27, No. 5, pp. 1263-1270.

Crisostomo et al., "Embryonic Stem Cells Attenuate Myocardial Dysfunction and Inflammation After Surgical Global Ischemia Via Paracrine Actions", American Journal of Physiology—Heart and Circulatory Physiology, 2008, vol. 295, pp. H1726-H1735.

Csete, Marie, "Oxygen in the Cultivation of Stem Cells", Annals New York Academy of Sciences, 2005, vol. 1049, pp. 1-8.

"Culture Media Database", EGM-2 (Endothelial Growth Medium 2)—ID 63, downloaded from http://bio.lonza.com/3018.html#ext-comp-1003:tab_63:change, printed on Jan. 14, 2013, p. 1.

Davis et al., "Isolation and Expansion of Functionally-Competent Cardiac Progenitor Cells Directly from Heart Biopsies", Journal of Molecular and Cellular Cardiology, Aug. 2010, vol. 49, No. 2, pp. 312-321.

Davis et al., "Validation of the Cardiosphere Method to Culture Cardiac Progenitor Cells from Myocardial Tissue", PLoS One, 2009, vol. 4, No. 9, e7195, pp. 1-8.

Davis et al., "Human Cardiospheres are a Source of Stem Cells with Cardiomyogenic Potential", Stem Cells, 2010, vol. 28, No. 5, pp. 903-904.

De Bakker et al., "Slow Conduction in the Infarcted Human Heart 'Zigzag' Course of Activation", Circulation, Sep. 1993, pp. 915-926, vol. 88, No. 3.

De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.

De Pomerai et al., "Influence of Serum Factors on the Prevalence of 'Normal' and 'Foreign' Differentiation Pathways in the Cultures of Chick Embryo Neuroretinal Cells", Journal of Embryology and Experimental Morphology, 1981, pp. 291-308, vol. 62.

Deal et al., "Molecular Physiology of Cardiac Potassium Channels", Physiological Reviews, Jan. 1996, vol. 76, No. 1, pp. 49-67.

Del Monte et al., "Abrogation of Ventricular Arrhythmias in a Model of Ischemia and Reperfusion by Targeting Myocardial Calcium Cycling", Proceedings of the National Academy of Sciences of the United States of America (PNAS), Apr. 13, 2004, vol. 101, No. 15, pp. 5622-5627.

Deregibus et al., "Endothelial Progenitor Cell-Derived Microvesicles Activate an Angiogenic Program in Endothelial Cells by a Horizontal Transfer of mRNA", Blood, Oct. 1, 2007, vol. 110, No. 7, pp. 2440-2448.

Derossi et al., "The Third Helix of the Antennapedia Homeodomain Translocates through Biological Membranes", The Journal of Biological Chemistry, Apr. 8, 1994, vol. 269, No. 14, pp. 10444-10450.

Di Meglio et al., "In Vitro Cultured Progenitors and Precursors of Cardiac Cell Lineages from Human Normal and Post-Ischemic Hearts", European Journal of Histochemistry, Oct.-Dec. 2007, vol. 51, No. 4, pp. 275-285.

Dispersyn et al., "Adult Rabbit Cardiomyocytes Undergo Hibernation-Like Dedifferentiation When Co-Cultured with Cardiac Fibroblasts", Cardiovascular Research, 2001, vol. 51, pp. 230-240.

Dispersyn et al., "Dissociation of Cardiomyocyte Apoptosis and Dedifferentiation in Infarct Border Zones", European Heart Journal, 2002, vol. 23, pp. 849-857.

Dixon et al., "Quantitative Analysis of Potassium Channel mRNA Expression in Atrial and Ventricular Muscle of Rats", Circulation Research, Aug. 1994, vol. 75, No. 2, pp. 252-260.

Dixon et al., "Role of the Kv4.3 $K^+$ Channel in Ventricular Muscle", Circulation Research, 1996, vol. 79, pp. 659-668.

Djokic et al., "Post-Transplant Lymphoproliferative Disorder Subtypes Correlate with Different Recurring Chromosomal Abnormalities", Genes, Chromosomes & Cancer, 2006, vol. 45, pp. 313-318.

Donahue et al., "Ultrarapid, Highly Efficient Viral Gene Transfer to the Heart", Proceedings of the National Academy of Sciences of the United States of America, Apr. 1997, vol. 94, pp. 4664-4668.

Dong et al., "Islet Cell and Extrapancreatic Expression of the LIM Domain Homeobox Gene isl-1", Molecular Endocrinology, 1991, vol. 5, No. 11, pp. 1633-1641.

Drakos et al., "Impact of Mechanical Unloading on Microvasculature and Associated Central Remodeling Features of the Failing Human Heart", Journal of the American College of Cardiology, Jul. 27, 2010, vol. 56, No. 5, pp. 382-391.

Driesen et al., "Structural Adaptation in Adult Rabbit Ventricular Myocytes: Influence of Dynamic Physical Interaction With Fibroblasts", Cell Biochemistry and Biophysics, 2006, vol. 44: 119-128.

Driesen et al., "Structural Remodeling of Cardiomyocytes in the Border Zone of Infarcted Rabbit Heart", Molecular and Cellular Biochemistry, 2007, pp. 225-232, vol. 302.

Duff et al., "CD105 is Important for Angiogenesis: Evidence and Potential Applications," FASEB Journal, Jun. 2003, vol. 17, No. 9, pp. 984-992.

Eguchi, Masakatsu, "Recent Advances in Selective Opioid Receptor Agonists and Antagonists", Medicinal Research Reviews, 2004, vol. 24, No. 2, pp. 182-212.

Elliott et al., "Intercellular Trafficking and Protein Delivery by a Herpesvirus Structural Protein", Cell, Jan. 24, 1997, vol. 88, pp. 223-233.

Elliott et al., "Intercellular Trafficking of VP22-GFP Fusion Proteins", Gene Therapy, 1999, vol. 6, pp. 149-151.

Engel et al., FGF1/p38 MAP Kinase Inhibitor Therapy Induces Cardiomyocyte Mitosis, Reduces Scarring, and Rescues Function after Myocardial Infarction, Proceedings of the National Academy of Sciences of the United States of America (PNAS), Oct. 17, 2006, vol. 103, No. 42, pp. 15546-15551.

Engel et al. "p38 MAP Kinase Inhibition Enables Proliferation of Adult Mammalian Cardiomyocytes", Genes & Development, May 2005, vol. 19, No. 10, pp. 1175-1187.

Eppenberger-Eberhardt et al., "Reexpression of α-Smooth Muscle Acting Isoform in Cultured Adult Rat Cardiomyocytes", Developmental Biology, Jun. 1990, vol. 139, No. 2, pp. 269-278.

Eschenhagen et al., "Engineering Myocardial Tissue", Circulation Research, 2005, vol. 97, pp. 1220-1231.

Falck et al., "Conserved Modes of Recruitment of ATM, ATR and DNA-PKcs to Sites of DNA Damage", Nature, Mar. 31, 2005, vol. 434, pp. 605-611.

Fehrer et al., "Reduced Oxygen Tension Attenuates Differentiation Capacity of Human Mesenchymal Stem Cells and Prolongs their Lifespan", Aging Cell, 2007, vol. 6, pp. 745-757.

Fiset et al., Shal-Type Channels Contribute to the $Ca^{2+}$-Independent Transient Outward $K^+$ Current in Rat Ventricle, Journal of Physiology, 1997, vol. 500, No. 1, pp. 51-64.

Foreman et al., "Reactive Oxygen Species Produced by NADPH Oxidase Regulate Plant Cell Growth", Nature, Mar. 27, 2003, vol. 422, pp. 442-446.

(56) References Cited

OTHER PUBLICATIONS

Frankel et al., "Cellular Uptake of the Tat Protein from Human Immunodeficiency Virus", Cell, vol. 55, Dec. 23, 1988, pp. 1189-1193.

Freyman et al., "A Quantitative, Randomized Study Evaluating Three Methods of Mesenchymal Stem Cell Delivery Following Myocardial Infarction", European Heart Journal, 2006, vol. 27, pp. 1114-1122.

Furlani et al., "A Transformed Cell Population Derived From Cultured Mesenchymal Stem Cells Has no Functional Effect After Transplantation Into the Injured Heart", Cell Transplantation, 2009, vol. 18, pp. 319-331.

Gallet et al., "Intracoronary Delivery of Self-Assembling Heart-Derived Microtissues (Cardiospheres) For Prevention of Adverse Remodeling In a Pig Model of Convalescent Myocardial Infarction", http://circinterventions.ahajournals.org, Dec. 8, 2015, pp. 21.

Galli et al., "Neural Stem Cells: An Overview", Circulation Research, 2003, vol. 92, No. 6, pp. 598-608.

Gatti et al., Microvesicles Derived from Human Adult Mesenchymal Stem Cells Protect Against Ischaemia-Reperfusion-Induced Acute and Chronic Kidney Injury, Nephrology Dialysis Transplantation, 2011, vol. 26, No. 5, pp. 1474-1483.

George et al., "Echocardiographic Assessment of Flow Across Continuous-Flow Ventricular Assist Devices at Low Speeds", The Journal of Heart and Lung Transplantation, Nov. 2010, vol. 29, No. 11, pp. 1245-1252.

Gibco, "Insulin-Transferrin-Selenium", Product Sheet, 2014.

Gibco, "Insulin-Transferrin-Selenium: 100X (For General Tissue Culture Applications)", Product Sheet, Form No. 2672, Jun. 2001, p. 1.

Gidh-Jain et al., Differential Expression of Voltage-Gated $K^+$ Channel Genes in Left Ventricular Remodeled Myocardium After Experimental Myocardial Infarction, Circulation Research, 1996, vol. 79, pp. 669-675.

Glover et al., "Reduction of Infarct Size and Postischemic Inflammation from ATL-146e, a Highly Selective Adenosine $A_{2A}$ Receptor Agonist in Reperfused Canine Myocardium", American Journal of Physiology—Heart and Circulatory Physiology, Apr. 2005, vol. 288, No. 4, pp. H1851-H1858.

Gómez-Márquez et al., "Thymosin-β4 Gene: Preliminary Characterization and Expression in Tissues, Thymic Cells, and Lymphocytes", The Journal of Immunology, Oct. 15, 1989, vol. 143, No. 8, pp. 2740-2744.

Good et al., "β-Amyloid Peptide Blocks the Fast-Inactivating $K^+$ Current in Rat Hippocampal Neurons", Biophysical Journal, Jan. 1996, vol. 70, pp. 296-304.

Goumans et al., "TGF-β1 Induces Efficient Differentiation of Human Cardiomyocyte Progenitor Cells into Functional Cardiomyocytes In Vitro", Stem Cell Research, 2008, vol. 1, pp. 138-149.

Grayson et al. "Hypoxia Enhances Proliferation and Tissue Formation of Human Mesenchymal Stem Cells", Biochemical and Biophysical Research Communications, 2007, vol. 358, pp. 948-953.

Green et al., "Autonomous Functional Domains of Chemically Synthesized Human Immunodeficiency Virus Tat Trans-Activator Protein", Dec. 23, 1988, Cell, vol. 55, pp. 1179-1188.

Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.

Grigorian-Shamagian et al., "Harnessing the Heart's Resistance to Malignant Tumors; Cardiac-Derived Extracellular Vesicles Decrease Fibrosarcoma Growth and Leukemia-Related Mortality in Rodents", Oncotarget, 2017, vol. 8, No. 59, p. 99624-99636.

Grossman et al., "Contractile State of the Left Ventricle in Man as Evaluated from End-Systolic Pressure-Volume Relations", Circulation, vol. 56, No. 5, Nov. 1977, pp. 845-852.

Gu, Yiping, "Bispecific Antibody Targeted Stem Cell Therapy for Myocardial Repair", Dissertation, University of California San Francisco and University of California Berkeley, 2008, pp. 94.

Gubbay et al., "A Gene Mapping to the Sex-Determining Region of the Mouse Y Chromosome is a Member of a Novel Family of Embryonically Expressed Genes", Nature, Jul. 19, 1990, vol. 346, pp. 245-250.

Hacein-Bey-Abina et al., "LMO2-Associated Clonal T Cell Proliferation in Two Patients after Gene Therapy for SCID-X1", Science, Oct. 17, 2003, vol. 302, pp. 415-419 with Erratum in 1 page.

Haderk et al., "Tumor-Derived Exosomes Modulate PD-L1 Expression in Monocytes", Science Immunology, Jul. 28, 2017, vol. 2, No. 13, pp. 1-11.

Hagège, MD, PhD, et al., "Skeletal Myoblast Transplantation in Ischemic Heart Failure: Long-Term Follow-Up of the First Phase I Cohort of Patients", Circulation, Jul. 4, 2006, vol. 114, No. 1, pp. 1108-1113.

Haider et al., "Bone Marrow Stem Cell Transplantation for Cardiac Repair", American Journal of Physiology—Heart and Circulatory Physiology, 2005, H2557-H2567, vol. 288.

Hainsworth et al., "The Nitrone Disodium 2,4-Sulphophenyl-N-Tert-Butylnitrone is Without Cytoprotective Effect on Sodium Nitroprusside-Induced Cell Death in N1E-115 Neuroblastoma Cells in vitro", Journal of Cerebral Blood Flow & Metabolism, 2008, vol. 28, pp. 24-28.

Haj-Yahia et al., "Limited Surgical Approach for Explanting the HeartMate II Left Ventricular Assist Device after Myocardial Recovery", The Journal of Thoracic and Cardiovascular Surgery, 2008, vol. 135, No. 2, pp. 453-454.

Harvey, "Molecular Determinants of Cardiac Development and Congenital Disease," Mouse Development, Patterning, Morphogenesis, and Organogensis, 2002, pp. 331-370, Chapter 16.

Heng et al., "Incorporating Protein Transduction Domains (PTD) Within Recombinant 'Fusion' Transcription Factors. A Novel Strategy for Directing Stem Cell Differentiation?" Biomedicine and Pharmacotherapy, Apr. 1, 2005, vol. 59, No. 3, pp. 132-134.

Hergenreider et al., "Atheroprotective Communication Between Endothelial Cells and Smooth Muscle Cells Through miRNAs", Nature Cell Biology, Mar. 2012, vol. 14, No. 3, pp. 249-256.

Herrera et al., "Human Liver Stem Cell-Derived Microvesicles Accelerate Hepatic Regeneration in Hepatectomized Rats", Journal of Cellular and Molecular Medicine, 2010, vol. 14, No. 6B, pp. 1605-1618.

Hierlihy et al., "The Post-Natal Heart Contains a Myocardial Stem Cell Population", FEBS Letters, 2002, vol. 530, No. 1-3, pp. 239-243.

Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.

Hochedlinger et al., "Nuclear Reprogramming and Pluripotency", Nature, Jun. 29, 2006, vol. 441, pp. 1061-1067.

Hu et al., "MicroRNA-210 as a Novel Therapy for Treatment of Ischemic Heart Disease", Circulation, Sep. 14, 2010, vol. 122, Supplement 11, S124-S131, pp. 17.

Hullinger et al., Inhibition of miR-15 Protects Against Cardiac Ischemic Injury, Circulation Research, Jan. 6, 2012, vol. 110, No. 1, pp. 71-81.

Ibrahim et al., "Exosomes as Critical Agents of Cardiac Regeneration Triggered by Cell Therapy", Stem Cell Reports, May 6, 2014, vol. 2, pp. 606-619.

Ibrahim et al., "Exosomes: Fundamental Biology and Roles in Cardiovascular Physiology", Annual Review of Physiology, 2016, vol. 78, pp. 67-83.

Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.

Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.

International Preliminary Report on Patentability and Written Opinion received in PCT/US2013/054732, dated Feb. 26, 2015 in 14 pages.

(56) References Cited

OTHER PUBLICATIONS

International Search Report and Written Opinion received in PCT Application No. PCT/US2013/054732, dated Mar. 4, 2014 in 19 pages.
Ivanovic, Zoran, "Hypoxia or In Situ Normoxia: The Stem Cell Paradigm", Journal of Cellular Physiology, 2009, vol. 219, pp. 271-275.
Jackson et al., "Regeneration of Ischemic Cardiac Muscle and Vascular Endothelium by Adult Stem Cells", The Journal of Clinical Investigation, Jun. 2001, pp. 1395-1402, vol. 107, No. 11.
Jayawardena et al., MicroRNA-Mediated In Vitro and In Vivo Direct Reprogramming of Cardiac Fibroblasts to Cardiomyocytes, Circulation Research, 2012, vol. 110, No. 11, pp. 1465-1473.
Johnston, MD, et al., "Engraftment, Differentiation, and Functional Benefits of Autologous Cardiosphere-Derived Cells in Porcine Ischemic Cardiomyopathy", Circulation, Sep. 22, 2009, vol. 120, pp. 1075-1083.
Jutkiewicz, Emily, The Antidepressant-Like Effects of Delta-Opioid Receptor Agonists, Molecular Interventions, 2006, vol. No. 3, pp. 162-169.
Kääb et al., "Ionic Mechanism of Action Potential Prolongation in Ventricular Myocytes From Dogs With Pacing-Induced Heart Failure", Circulation Research, 1996, vol. 78, No. 2, pp. 262-273.
Kamdar et al., "Dystrophin-Deficient Cardiomyopathy", Journal of the American College of Cardiology, 2016, vol. 67, No. 21, pp. 2533-2546.
Karlsson et al., "Insulin Gene Enhancer Binding Protein Isl-1 is a Member of a Novel Class of Proteins Containing Both a Homeo-and a Cys-His Domain", Nature, Apr. 26, 1990, vol. 344, pp. 879-882.
Karoubi et al., "Single-Cell Hydrogel Encapsulation for Enhanced Survival of Human Marrow Stromal Cells", Biomaterials, 2009, vol. 30, pp. 5445-5455.
Kaspar et al., "Current Understanding and Management of Dilated Cardiomyopathy in Duchenne and Becker Muscular Dystrophy", Journal of the American Association of Nurse Practitioners, May 2009, vol. 21, No. 5, pp. 241-249.
Kawaguchi et al., "Cell Shape and Cardiosphere Differentiation: A Revelation by Proteomic Profiling", Hindawi Publishing Corporation, Biochemistry Research International, vol. 2013, Article ID 730874, pp. 1-9.
Kim et al., "Generation of Human Induced Pluripotent Stem Cells by Direct Delivery of Reprogramming Proteins", Cell Stem Cell, Jun. 5, 2009, vol. 4, No. 6, pp. 472-476.
Kisselbach et al., "CD90 Expression on Human Primary Cells and Elimination of Contaminating Fibroblasts from Cell Cultures", Cytotechnology, 2009, pp. 31-44, vol. 59.
Kooijmans et al., "PEGylated and Targeted Extracellular Vesicles Display Enhanced Cell Specificity and Circulation Time", Journal of Controlled Release, 2016, vol. 224, pp. 77-85.
Kühn et al., "Periostin Induces Proliferation of Differentiated Cardiomyocytes and Promotes Cardiac Repair", Nature Medicine, Aug. 2007, vol. 13, No. 8, pp. 962-969.
Kutschka et al., "Collagen Matrices Enhance Survival of Transplanted Cardiomyoblasts and Contribute to Functional Improvement of Ischemic Rat Hearts", Circulation, Jul. 4, 2006, vol. 114, pp. 1167-1173.
Kwon et al., "Cellular Manipulation of Human Embryonic Stem Cells by TAT-PDX1 Protein Transduction," Molecular Therapy, Jul. 1, 2005, vol. 12, No. 1, pp. 28-32.
Kyrtatos et al., "Magnetic Tagging Increases Delivery of Circulating Progenitors in Vascular Injury", Journal of the American College of Cardiology: Cardiovascular Interventions, 2009, pp. 794-802, vol. 2, No. 8.
Laflamme et al., "Cardiomyocytes Derived from Human Embryonic Stem Cells in Pro-Survival Factors Enhance Function of Infarcted Rat Hearts", Nature Biotechnology, Sep. 2007, vol. 25, No. 9, pp. 1015-1024.
Lai et al., "Exosome Secreted by MSC Reduces Myocardial Ischemia/Reperfusion Injury", Stem Cell Research, 2010, vol. 4, pp. 214-222.

Lapchak et al., "Intravenous Xenogeneic Human Cardiosphere-Derived Cell Extracellular Vesicles (Exosomes) Improves Behavioral Function in Small-Clot Embolized Rabbits", Experimental Neurology, vol. 307, Sep. 2018, pp. 109-117.
Landázuri et al., "Complexation of Retroviruses with Charged Polymers Enhances Gene Transfer by Increasing the Rate that Viruses are Delivered to Cells", The Journal of Gene Medicine, 2004, vol. 6, pp. 12, pp. 1304-1319.
Lavon et al., "Derivation of Euploid Human Embryonic Stem Cells from Aneuploid Embryos", Stem Cells, 2008, vol. 26, pp. 1874-1882.
Lee et al., "Antibody Targeting of Stem Cells to Infarcted Myocardium", Stem Cells: Translational and Clinical Research, 2007, pp. 712-717, vol. 25.
Lee et al., "Cardiac Gene Transfer by Intracoronary Infusion of Adenovirus Vector-Mediated Reporter Gene in the Transplanted Mouse Heart", The Journal of Thoracic and Cardiovascular Surgery, 1996, pp. 246-252, vol. 111.
Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Leferovich et al., "Heart Regeneration in Adult MRL Mice", Proceedings of the National Academy of Sciences of the United States of America (PNAS), Aug. 14, 2001, vol. 98, No. 17, pp. 9830-9835.
Leor, MD, et al., "Transplantation of Fetal Myocardial Tissue Into the Infarcted Myocardium of Rat", Circulation, Nov. 1, 1996, vol. 94, No. 9, II-332-II-336.
Levenberg at al., "Endothelial Cells Derived from Human Embryonic Stem Cells", Proceedings of the National Academy of Sciences of the United States of America (PNAS), Developmental Biology, Apr. 2, 2002, pp. 4391-4396, vol. 99, No. 7.
Levine et al., "Vitamin C Pharmacokinetics in Healthy Volunteers: Evidence for a Recommended Dietary Allowance", Proceedings of the National Academy of Sciences of the United States of America, Apr. 1996, vol. 93, pp. 3704-3709.
Li et al., "Cardiospheres Recapitulate a Niche-Like Microenvironment Rich in Sternness and Cell-Matrix Interactions, Rationalizing Their Enhanced Functional Potency for Myocardial Repair", Stem Cells: Translational and Clinical Research, 2010, pp. 2088-2098, vol. 28.
Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.
Li et al., "Expansion of Human Cardiac Stem Cells in Physiological Oxygen Improves Cell Production Efficiency and Potency for Myocardial Repair", Cardiovascular Research, Jul. 29, 2010, pp. 1-9.
Li et al., "Late-Breaking Basic Science Abstracts From the American Heart Association's Scientific Sessions 2009", Late-Breaking Basic Science Oral Abstracts: Translational Studies, Molecular, Cellular, and Functional Phenotypes of Human Cardiac Stem Cells Dependent Upon Monolayer Versus Three-Dimensional Culture Conditions, Abstract 5173, Circulation Research, Dec. 4, 2009, vol. 105, No. 12, pp. e56-e62.
Li et al., "Molecular, Cellular, and Functional Phenotypes of Human Cardiac Stem Cells Dependent Upon Monolayer Versus Three-Dimensional Culture Conditions", Circulation Research, Dec. 4, 2009, Abs. 5173, vol. 105, No. 12, p. e58.
Li et al., "Physiological Levels of Reactive Oxygen Species Are Required to Maintain Genomic Stability in Stem Cells", Stem Cell, Stem Cell Technology: Epigenetics, Genomics, Proteomics, and Metabonomics, May 4, 2010, vol. 28, pp. 1178-1185.
Li, MD, PhD et al., "Imaging Survival and Function of Transplanted Cardiac Resident Stem Cells", Journal of the American College of Cardiology, Apr. 7, 2009, vol. 53, No. 14, pp. 1229-1240.
Liao et al., "Enhanced Efficiency of Generating Induced Pluripotent Stem (iPS) Cells from Human Somatic Cells by a Combination of Six Transcription Factors", Cell Research, 2008, vol. 18, pp. 600-603.

(56) References Cited

OTHER PUBLICATIONS

Lin et al., "Accelerated Growth and Prolonged Lifespan of Adipose Tissue-Derived Human Mesenchymal Stem Cells in a Medium Using Reduced Calcium and Antioxidants", Stem Cells and Development, 2005, vol. 14, pp. 92-102.
Lindsay, Mark A., "Peptide-Mediated Cell Delivery: Application in Protein Target Validation", Current Opinion in Pharmacology, 2002, vol. 2, pp. 587-594.
Lindsley et al., "The PI3K/Akt Pathway: Recent Progress in the Development of ATP-Competitive and Allosteric Akt Kinase Inhibitors", Current Cancer Drug Targets, 2008, vol. 8, pp. 7-18.
Lipinski et al., "Impact of Intracoronary Cell Therapy on Left Ventricular Function in the Setting of Acute Myocardial Infarction: A Collaborative Systematic Review and Meta-Analysis of Controlled Clinical Trials", Journal of the American College of Cardiology, 2007, vol. 50, No. 18, pp. 1761-1767.
Liu et al. "Autologous Stem Cell Transplantation for Myocardial Repair", American Journal of Physiology, Heart and Circulatory Physiology, 2004, pp. H501-H511, vol. 287.
Liu et al., "Osteochondral Defect Repair with Autologous Bone Marrow-Derived Mesenchymal Stem Cells in an Injectable, In Situ, Cross-Linked Synthetic Extracellular Matrix", Tissue Engineering, 2006, pp. 3405-3416, vol. 12, No. 12.
Lowry et al., "Generation of Human Induced Pluripotent Stem Cells from Dermal Fibroblasts", Proceedings of the National Academy of Sciences of the United States of America (PNAS), Feb. 26, 2008, vol. 105, No. 8, pp. 2883-2888.
Lum et al., "The New Face of Bispecific Antibodies: Targeting Cancer and Much More", Experimental Hematology, 2006, pp. 1-6, vol. 34.
Lyngbaek et al., "Cardiac Regeneration by Resident Stem and Progenitor Cells in the Adult Heart", Basic Research in Cardiology, 2007, vol. 102, pp. 101-114.
Maitra et al, Genomic Alterations in Cultured Human Embryonic Stem Cells, Nature Genetics, Oct. 2005, vol. 37, No. 10, pp. 1099-1103.
Maletic-Savatic et al., "Differential Spatiotemporal Expression of $K^+$ Channel Polypeptides in Rat Hippocampal Neurons Developing In Situ and In Vitro", The Journal of Neuroscience, May 1995, vol. 15, No. 5, pp. 3840-3851.
Mangi et al., "Mesenchymal Stem Cells Modified with Akt Prevent Remodeling and Restore Performance of Infarcted Hearts," Nature Medicine, Sep. 2003, vol. 9, No. 9, pp. 1195-1201.
Marbán, Eduardo, "Big Cells, Little Cells, Stem Cells: Agents of Cardiac Plasticity", Circulation Research, 2007, vol. 100, No. 4, pp. 445-446.
Marshall et al., "The Jellyfish Green Fluorescent Protein: A New Tool for Studying Ion Channel Express and Function", Neuron, Feb. 1995, vol. 14, pp. 211-215.
Martens et al., "Percutaneous Cell Delivery Into the Heart Using Hydrogels Polymerizing In Situ", Cell Transplantation, 2009, vol. 18, No. 3, pp. 297-304.
Matsuura et al., "Adult Cardiac Sca-1-positive Cells Differentiate into Beating Cardiomyocytes", The Journal of Biological Chemistry, Mar. 19, 2004, vol. 279, No. 12, pp. 11384-11391.
McGann et al., "Mammalian Myotube Dedifferentiation Induced by Newt Regeneration Extract", Proceedings of the National Academy of Sciences of the United States of America (PNAS), Nov. 20, 2001, vol. 98, No. 24, pp. 13699-13704.
Mehmel et al., "The Linearity of the End-Systolic Pressure-Volume Relationship in Man and its Sensitivity for Assessment of Left Ventricular Function", Circulation, 1981, vol. 63, pp. 1216-1222.
Messina et al., "Isolation and Expansion of Adult Cardiac Stem Cells from Human and Murine Heart", Oct. 29, 2004, Circulation Research, Cellular Biology, American Heart Association, vol. 95, pp. 911-921.
Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.

Miller III, et al., Meta-Analysis: High-Dosage Vitamin E Supplementation May Increase All-Cause Mortality, Annals of Internal Medicine, 2005, vol. 142, pp. 37-46.
Miltenyi et al., "High Gradient Magnetic Cell Separation With MACS[1]", Cytometry, 1990, pp. 231-238, vol. 11.
Mitsui et al., "The Homeoprotein Nanog is Required for Maintenance of Pluripotency in Mouse Epiblast and ES Cells", Cell, May 30, 2003, vol. 113, No. 5, pp. 631-642.
Miyazono et al. "Latent High Molecular Weight Complex of Transforming Growth Factor β1", May 5, 1988, vol. 263, No. 13, pp. 6407-6415.
Montessuit et al., "Regulation of Glucose Transporter Expression in Cardiac Myocytes: p38 MAPK is a Strong Inducer of GLUT4", Cardiovascular Research, Oct. 1, 2004, vol. 64, No. 1, pp. 94-104.
Montessuit et al., "Retinoic Acids Increase Expression of GLUT4 in Dedifferentiated and Hypertrophied Cardiac Myocytes", Basic Research in Cardiology, Jan. 1, 2006, vol. 101, No. 1, pp. 27-35.
Moss et al., "Conservation of the Heterochronic Regulator Lin-28, its Developmental Expression and MicroRNA Complementary Sites", Developmental Biology, 2003, vol. 258, No. 2, pp. 432-442.
Moss, M.D., et al., Prophylactic Implantation of a Defibrillator in Patients with Myocardial Infarction and Reduced Ejection Fraction, The New England Journal of Medicine, Mar. 21, 2002, vol. 346, No. 12, pp. 877-883.
Murata et al., "C4d Deposition and Cellular Infiltrates as Markers of Acute Rejection in Rat Models of Orthotopic Lung Transplantation", Transplantation, Jul. 15, 2008, vol. 86, No. 1, pp. 123-129.
Nadal-Ginard et al, "Myocyte Death, Growth, and Regeneration in Cardiac Hypertrophy and Failure", Circulation Research, 2003, vol. 92, pp. 139-150.
Nadal-Ginard et al., "A Matter of Life and Death: Cardiac Myocyte Apoptosis and Regeneration", Journal of Clinical Investigation, May 2003, vol. 111, No. 10, pp. 1457-1459.
Naka et al., "Regulation of Reactive Oxygen Species and Genomic Stability in Hematopoietic Stem Cells", Antioxidants & Redox Signaling, 2008, vol. 10, No. 11, pp. 1883-1894.
Nakagawa et al., "Generation of Induced Pluripotent Stem Cells without Myc from Mouse and Human Fibroblasts", Nature Biotechnology, Jan. 2008, vol. 26, No. 1, pp. 101-106.
Nakasa et al., "Acceleration of Muscle Regeneration by Local Injection of Muscle-Specific MicroRNAs in Rat Skeletal Muscle Injury Model", Journal of Cellular and Molecular Medicine, 2010, vol. 14, No. 10, pp. 2495-2505.
Nelson et al., "$CXCR4^+/FLK-1^+$ Biomarkers Select a Cardiopoietic Lineage from Embryonic Stem Cells", Stem Cells, 2008, vol. 26, pp. 1464-1473.
Nelson, MD, PhD et al., "Repair of Acute Myocardial Infarction with iPS Induced by Human Sternness Factors", Circulation, Aug. 4, 2009, vol. 120, No. 5, pp. 408-416.
Niethammer et al., "A Tissue-Scale Gradient of Hydrogen Peroxide Mediates Rapid Wound Detection in Zebrafish", Nature, Jun. 18, 2009, vol. 459, pp. 996-999.
Noguchi et al., "Protein Transduction Technology: A Novel Therapeutic Perspective", Acta Medica Okayama, 2006, vol. 60, No. 1, pp. 1-11.
Nussbaum et al., "Transplantation of Undifferentiated Murine Embryonic Stem Cells in the Heart: Teratoma Formation and Immune Response", The FASEB Journal, Research Communication, May 2007, vol. 21, No. 7, pp. 1345-1357.
Odelberg et al., "Dedifferentiation of Mammalian Myotubes Induced by msx1", Cell, Dec. 22, 2000, vol. 103, No. 7, pp. 1099-1109.
Odelberg, Shannon J., Inducing Cellular Dedifferentiation: A Potential Method for Enhancing Endogenous Regeneration in Mammals., Seminars in Cell & Developmental Biology, 2002, vol. 13, No. 5, pp. 335-343.
Offord et al., "Photoprotective Potential of Lycopene, -Carotene, Vitamin E, Vitamin C and Carnosic in UVA-Irradiated Human Skin Fibroblasts", Free Radical Biology & Medicine, 2002, vol. 32, No. 12, pp. 1293-1303.
Oh et al., "Cardiac Muscle Plasticity in Adult and Embryo by Heart-Derived Progenitor Cells", Annals of the New York Academy of Sciences, 2004, vol. 1015, pp. 182-189.

(56) References Cited

OTHER PUBLICATIONS

Oh et al., "Cardiac Progenitor Cells from Adult Myocardium: Homing, Differentiation, and Fusion After Infarction", Proceedings of the National Academy of Sciences of the United States of America (PNAS), Oct. 14, 2003, p. 12313-12318, vol. 100, No. 21.
Okita et al., Generation of Mouse Induced Pluripotent Stem Cells Without Viral Vectors, Nov. 7, 2008, Science, vol. 322, pp. 949-953.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, http://circ.ahajournals.org/content/132/Suppl_3/A13881.short.
Owusu-Ansah et al., "Reactive Oxygen Species Prime *Drosophila* Haematopoietic Progenitors for Differentiation", Nature, Sep. 24, 2009, vol. 461, pp. 537-541.
Park et al., "Reprogramming of Human Somatic Cells to Pluripotency with Defined Factors", Nature, Jan. 10, 2008, vol. 451, pp. 141-146.
Passier et al., "Stem-Cell-Based Therapy and Lessons from the Heart", May 15, 2008, Nature, vol. 453, pp. 322-329.
Passier et al., "Origin and Use of Embryonic and Adult Stem Cells in Differentiation and Tissue Repair", Cardiovascular Research, 2003, vol. 58, No. 2, pp. 324-335.
Payne, Anthony G., "Using Immunomagnetic Technology and Other Means to Facilitate Stem Cell Homing", Medical Hypotheses, 2004, pp. 718-720, vol. 62.
Peterson, MD, MPH, et al., "Risk Stratification After Myocardial Infarction", Annals of Internal Medicine, 1997, vol. 126, No. 7, pp. 561-582.
Pike et al., "Heparin-Regulated Release of Growth Factors In Vitro and Angiogenic Response In Vivo to Implanted Hyaluronan Hydrogels Containing VEGF and bFGF," Biomaterials, 2006, vol. 27, pp. 5242-5241.
Piper et al. "Determinants of Cardiomyocyte Development in Long-Term Primary Culture", Journal of Molecular and Cellular Cardiology, 1988, vol. 20, pp. 825-835.
Plotnikov et al., "Biological Pacemaker Implanted in Canine Left Bundle Branch Provides Ventricular Escape Rhythms that Have Physiologically Acceptable Rates", Circulation, 2004, vol. 109, pp. 506-512.
Potapova et al., "Enhanced Recovery of Mechanical Function in the Canine Heart by Seeding an Extracellular Matrix Patch with Mesenchymal Stem Cells Committed to a Cardiac Lineage", American Journal of Physiology—Heart and Circulatory Physiology, 2008, vol. 295, pp. H2257-H2263.
Prestwich et al., "The Translational Imperative: Making Cell Therapy Simple and Effective", Acta Biomaterialia, 2012, vol. 8, pp. 4200-4207.
Prunier et al., "Delayed Erythropoietin Therapy Reduces Post-MI Cardiac Remodeling Only at a Dose that Mobilizes Endothelial Progenitor Cells", American Journal of Physiology—Heart and Circulatory Physiology, 2007, vol. 292, pp. H522-H529.
Puceat, Michel, "Role of Rac-GTPase and Reactive Oxygen Species in Cardiac Differentiation of Stem Cell", Antioxidants & Redox Signaling, 2005, vol. 7, No. 11 & 12, pp. 1435-1439.
Qin et al., "ATM-Mediated Transcriptional Elevation of Prion in Response to Copper-Induced Oxidative Stress", The Journal of Biological Chemistry, Feb. 13, 2009, vol. 284, No. 7, pp. 4582-4593.
Quaini et al., "Chimerism of the Transplanted Heart", The New England Journal of Medicine, Jan. 3, 2002, vol. 346, No. 1, pp. 5-15.
Quevedo et al., "Allogeneic Mesenchymal Stem Cells Restore Cardiac Function in Chronic Ischemic Cardiomyopathy via Trilineage Differentiating Capacity", Proceedings of the National Academy of Sciences of the United States of America (PNAS), Aug. 18, 2009, vol. 106, No. 33, pp. 14022-14027.
Rajasekaran et al., "Human αB-Crystallin Mutation Causes Oxido-Reductive Stress and Protein Aggregation Cardiomyopathy in Mice", Cell, 2007, vol. 130, No. 3, pp. 427-439.
Ranghino et al., "Endothelial Progenitor Cell-Derived Microvesicles Improve Neovascularization in a Murine Model of Hindlimb Ischemia", International Journal of Immunopathology and Pharmacology, 2012, vol. 25, No. 1, pp. 75-85.
Reiffel, James A., MD, FACC, "Ten Pearls for the Use of Antiarrhythmic Drugs for Atrial Fibrillation", Aug. 17, 2012, Retrieved from http://www.acc.org/latest-in-cardiology/articles/2014/07/18/15/12/ten-pearls-for-the-use-of-antiarrhythmic-drugs-for-atrial-fibrillation, pp. 17.
Riazifar et al., "Stem Cell Extracellular Vesicles: Extended Messages of Regeneration", Reviews in Advance, Oct. 19, 2016, vol. 14, No. 1, pp. 1-30.
Ribera, Angeles B., "Homogeneous Development of Electrical Excitability via Heterogeneous Ion Channel Expression", The Journal of Neuroscience, Feb. 1, 1996, vol. 16, No. 3, pp. 1123-1130.
Risebro et al., "Hand1 Regulates Cardiomyocyte Proliferation Versus Differentiation in the Developing Heart", Development, Nov. 2006, vol. 133, No. 22, pp. 4595-4606.
Rossi et al., "Deficiencies in DNA Damage Repair Limit the Function of Haematopoietic Stem Cells with Age", Nature, Jun. 7, 2007, vol. 447, pp. 725-729.
Rotwein et al., "Organization and Sequence of the Human Insulin-Like Growth Factor I Gene", The Journal of Biological Chemistry, Apr. 15, 1986, vol. 261, No. 11, pp. 4828-4832.
Rubio et al., "Spontaneous Human Adult Stem Cell Transformation", Cancer Research, 2005, vol. 65, pp. 3035-3039.
Rücker-Martin et al., "Dedifferentiation of Atrial Myocytes During Atrial Fibrillation: Role of Fibroblast Proliferation in Vitro", Cardiovascular Research, 2002, vol. 55, pp. 38-52.
Rudy, B. "Diversity and Ubiquity of K Channels", Neuroscience, 1988, vol. 25, No. 3, pp. 729-749.
Saito et al., "Cell Death Caused by Selenium Deficiency and Protective Effect of Antioxidants", The Journal of Biological Chemistry, Oct. 10, 2003, vol. 278, No. 41, pp. 39428-39434.
Sareen et al., Chromosome 7 and 19 Trisomy in Cultured Human Neural Progenitor Cells, PLoS One, Oct. 2009, vol. 4, No. 10, e7630, pp. 12.
Sasano et al., "Molecular Ablation of Ventricular Tachycardia after Myocardial Infarction", Natural Medicine, 2006, vol. 12, No. 11, pp. 1256-1258.
Sasano et al., "Ventricular Tachycardia from the Healed Myocardial Infarction Scar: Validation of an Animal Model and Utility of Gene Therapy", Heart Rhythm, Aug. 2009, vol. 6, No. 8, pp. S91-S97.
Scaria et al., "Host-Virus Genome Interactions: Marco Roles for MicroRNAs", Cellular Microbiology, 2007, vol. 9, No. 12, pp. 2784-2794.
Seifried et al., "A Review of the Interaction Among Dietary Antioxidants and Reactive Oxygen Species", Journal of Nutritional Biochemistry, 2007, vol. 18, pp. 567-579.
Sempere et al., Expression Profiling of Mammalian MicroRNAs Uncovers a Subset of Brain-Expressed MicroRNAs with Possible Roles in Murine and Human Neuronal Differentiation, Genome Biology, 2004, vol. 5, No. 3, pp. R13.1-R13.11.
Serôdio et al., "Cloning of a Novel Component of A-Type K+ Channels Operating at Subthreshold Potentials With Unique Expression in Heart and Brain", Journal of Neurophysiology, May 1996, vol. 75, No. 5, pp. 2174-2179.
Sert et al., "The Radioprotective Effect of Vitamins C, E and Vitamin E + Glutathione on the Small Intestine and the Thyroid Gland in Rats Irradiated with X-Rays", Turkish Journal of Medical Sciences, 2000, vol. 30, pp. 417-425.
Sesso, ScD, MPH, et al., "Vitamins E and C in the Prevention of Cardiovascular Disease in Men: The Physicians' Health Study II Randomized Controlled Trial", The Journal of the American Medical Association (JAMA), 2008, vol. 300, pp. 2123-2133.
Sharkey et al., "Stage-Specific Expression of Cytokine and Receptor Messenger Ribonucleic Acids in Human Preimplantation Embryos", 1995, Biology of Reproduction, 1995, vol. 53, pp. 955-962.
Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.
Shen et al. "Isolation of an Insulin-Like Growth Factor II cDNA with a Unique 5' Untranslated Region from Human Placenta", Mar.

(56) References Cited

OTHER PUBLICATIONS

1988, Proceedings of the National Academy of Sciences of the United States of America (PNAS), vol. 85, pp. 1947-1951.

Shenje et al., "Lineage Tracing of Cardiac Explant Derived Cells", PLoS One, Apr. 2008, vol. 3, No. 4, e1929, pp. 10.

Shimizu et al., "Fabrication of Pulsatile Cardiac Tissue Grafts Using a Novel 3-D Cell Sheet Manipulation Techniques and Temperature-Responsive Cell Culture Surfaces", Circulation Research, 2002, vol. 90, No. 3, pp. 1-10.

Shu et al., "Disulfide-Crosslinked Hyaluronan-Gelatin Hydrogel Films: A Covalent Mimic of the Extracellular Matrix for In Vitro Cell Growth", Biomaterials, 2003, vol. 24, pp. 3825-3834.

Sigma-Aldrich, Inc., "Nutrient Mixture F12 Ham Kaighn's Modification (F12K)", Product Description, May 2007, pp. 2.

Simpson et al., "A Tissue Engineering Approach to Progenitor Cell Delivery Results in Significant Cell Engraftment and Improved Myocardial Remodeling", Stem Cells, Sep. 2007, vol. 25, No. 9, pp. 2350-2357.

Singh, PhD, Jai Pal, "Enabling Technologies for Homing and Engraftment of Cells for Therapeutic Applications", JACC: Cardiovascular Interventions, Aug. 2009, vol. 2, No. 8, pp. 803-804.

Singh, et al. "High-Dose α-Tocopherol Therapy Does Not Affect HDL Subtractions in Patients with Coronary Artery Disease on Statin Therapy", Clinical Chemistry, 2007, vol. 53, No. 3, pp. 525-528.

Slaughter, MD et al., "Clinical Management of Continuous-Flow Left Ventricular Assist Devices in Advanced Heart Failure", The Journal of Heart and Lung Transplantation, Apr. 2010, vol. 29, No. 4S, pp. S1-39.

Smart et al., "De Novo Cardiomyocytes from Within the Activated Adult Heart After Injury", Nature, Jun. 30, 2011, vol. 474, pp. 640-646.

Smith, PhD et al., "Stem Cells in the Heart: What's the Buzz all About? Part 1: Preclinical Considerations", Heart Rhythm, May 2008, vol. 5, No. 5, pp. 749-757.

Smith, PhD et al., "Stem Cells in the Heart: What's the Buzz all About? Part 2: Arrhythmic Risks and Clinical Studies", Heart Rhythm, Jun. 2008, vol. 5, No. 6, pp. 880-887.

Smith et al., "Regenerative Potential of Cardiosphere-Derived Cells Expanded From Percutaneous Endomyocardial Biopsy Specimens", Circulation, Feb. 5, 2007, pp. 896-908, vol. 115.

Smith et al., "Unique Phenotype of Cardiospheres Derived from Human Endomyocardial Biopsies", Circulation, Supplement II, Oct. 25, 2005, pp. 2, vol. 112, No. 17.

Smith et al., "Unselected Human Cardiosphere-derived Cells are Functionally Superior to c-Kit- or CD90-Purified Cardiosphere-Derived Cells", Circulation, Supplement 2, Oct. 28, 2008, vol. 118, No. 17, p. 1.

Smits, Anke Maria, "Cell-Based Cardiac Repair", Thesis, Utrecht University, The Netherlands, 2009, pp. 180.

Srivastava et al., "Thymosin β4 Is Cardioprotective after Myocardial Infarction", Annals of the New York Academy of Sciences, Sep. 2007, vol. 1112, pp. 161-170. Abstract only.

Stańczyk, et al., "The Effect of Vitamin C and Glutathione on Ethanol Cytotoxicity and Selected Parameters of Pro- and Antioxidative Processes in Mouse Fibroblasts 3T3-L1", Polish Journal of Environmental Studies, 2005, vol. 15, No. 1, pp. 131-137.

Stewart et al. "Revision of the 1990 Working Formulation for the Standardization of Nomenclature in the Diagnosis of Heart Rejection", The Journal of Heart and Lung Transplantation, 2005, vol. 24, No. 11, pp. 1710-1720.

Stull et al., "Chronic Treatment With Allopurinol Boosts Survival and Cardiac Contractility in Murine Postischemic Cardiomyopathy", Circulation Research, Cellular Biology, Nov. 12, 2004, pp. 1005-1011.

Sussman, Mark A., "Myocardial Aging and Senescence: Where Have the Stem Cells Gone?" Annual Review of Physiology, 2004, vol. 66, pp. 29-48.

Takahashi et al., "Induction of Pluripotent Stem Cells from Adult Human Fibroblasts by Defined Factors," Cell, vol. 131, Nov. 30, 2007, pp. 861-872.

Takahashi et al., "Induction of Pluripotent Stem Cells from Fibroblast Cultures, Nature Protocols", 2007, vol. 2 No.12, pp. 3081-3089.

Takeda et al., "Human Oct3 Gene Family: cDNA Sequences, Alternative Splicing, Gene Organization, Chromosomal Location, and Expression at Low Levels in Adult Tissues", Nucleic Acids Research, 1992, vol. 20, No. 17, pp. 4613-4620.

Takehara, MD, PhD, et al., "Controlled Delivery of Basic Fibroblast Growth Factor Promotes Human Cardiosphere-Derived Cell Engraftment to Enhance Cardiac Repair for Chronic Myocardial Infarction" Journal of the American College of Cardiology, 2008, vol. 52, No. 23, pp. 1858-1865.

Takeshita et al. "Osteoblast-Specific Factor 2: Cloning of a Putative Bone Adhesion Protein with Homology with the Insect Protein Fasciclin I", Biochemical Journal, 1993, vol. 294, pp. 271-278.

Tateishi et al., "Clonally Amplified Cardiac Stem Cells are Regulated by Sca-1 Signaling for Efficient Cardiovascular Regeneration", Journal of Cell Science, 2007, vol. 120, No. 10, pp. 1791-1800.

Ten Dijke et al. "Identification of Another Member of the Transforming Growth Factor Type β Gene Family", Proceedings of the National Academy of Sciences of the United States of America (PNAS), 1988, vol. 85, pp. 4715-4719.

Terrovitis, MD, et al., "Assessment and Optimization of Cell Engraftment after Transplantation into the Heart", Circulation Research, Feb. 19, 2010, vol. 106, No. 3, pp. 479-494.

Terrovitis, MD, et al., "Noninvasive Quantification and Optimization of Acute Cell Retention by In Vivo Positron Emission Tomography after Intramyocardial Cardiac-Derived Stem Cell Delivery", Journal of the American College of Cardiology, Oct. 20, 2009, vol. 54, No. 17, pp. 1619-1626.

The Exosomes Derived from CDCs Experimental Data to Show that Unexpectedly Improved Characteristics are Exhibited, p. 1.

Tomita et al., "Cardiac Neural Crest Cells Contribute to the Dorman Multipotent Stem Cell in the Mammalian Heart", Journal of Cell Biology, Sep. 26, 2005, vol. 170, No. 7, pp. 1135-1148.

Torella et al., "Cardiac Stem Cell and Myocyte Aging, Heart Failure, and Insulin-Like Growth Factor-1 Overexpression", Circulation Research, 2004, vol. 95, pp. 514-524.

Torella et al., Resident Human Cardiac Stem Cells: Role in Cardiac Cellular Homeostasis and Potential for Myocardial Regeneration, Nature Clinical Practice: Cardiovascular Medicine, Mar. 2006, vol. 3, No. 1, pp. S8-S13.

Trevethick et al., "Treating Lung Inflammation with Agonists from the Adenosine A2A Receptor: Promises, Problems and Potential Solutions", British Journal of Pharmacology, 2008, vol. 155, pp. 463-474.

Tsagalou, MD, et al., "Depressed Coronary Flow Reserve is Associated with Decreased Myocardial Capillary Density in Patients with Heart Failure Due to Idiopathic Dilated Cardiomyopathy", Journal of the American College of Cardiology, 2008, vol. 52, No. 17, pp. 1391-1398.

Tseliou, et al., "Abstract 15925: Newt Exosomes are Bioactive on Mammalian Heart, Enhancing Proliferation of Rat Cardiomyocytes and Improving Recovery After Myocardial Infarction", Circulation, Nov. 10, 2015, vol. 132, No. 3, pp. 2.

Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.

Uemura et al., "Bone Marrow Stem Cells Prevent Left Ventricular Remodeling of Ischemic Heart Through Paracrine Signaling", Circulation Research, 2006, vol. 98, pp. 1414-1421.

Ueno et al., "Biphasic Role for Wnt/β-Catenin Signaling in Cardiac Specification in Zebrafish and Embryonic Stem Cells", Proceedings of the National Academy of Sciences of the United States of America (PNAS), Jun. 5, 2007, vol. 104, No. 23, pp. 9685-9690.

(56) References Cited

OTHER PUBLICATIONS

Ulloa-Montoya et al., "Culture Systems for Pluripotent Stem Cells", Journal of Bioscience and Bioengineering, 2005, vol. 100, No. 1, pp. 12-27.
Urbanek et al., "Cardiac Stem Cells Possess Growth Factor Receptor Systems That After Activation Regenerate the Infarcted Myocardium, Improving Ventricular Function and Long-term Survival", Circulation Research, 2005, vol. 97, pp. 663-673.
Urbanek et al., "Intense Myocyte Formation from Cardiac Stem Cells in Human Cardiac Hypertrophy", Proceedings of the National Academy of Sciences of the United States of America (PNAS), Sep. 2, 2003, vol. 100, No. 18, pp. 10440-10445.
Urbanek et al., Myocardial Regeneration by Activation of Multipotent Cardiac Stem Cells in Ischemic Heart Failure, Proceedings of the National Academy of Sciences of the United States of America (PNAS), Jun. 14, 2005, vol. 102, No. 24, pp. 8692-8697.
Van Der Geest et al., "Quantification in Cardiac MRI", Journal of Magnetic Resonance Imaging, 1999, vol. 10, pp. 602-608.
Van Gent et al., "Chromosomal Stability and the DNA Double-Stranded Break Connection", Nature, Mar. 2001, vol. 2, pp. 196-206.
Van Vliet et al., "Progenitor Cells Isolated from the Human Heart: a Potential Cell Source for Regenerative Therapy", Netherlands Heart Journal, May 2008, vol. 16, No. 5, pp. 163-169.
Van Winkle et al., "Cardiogel: A Biosynthetic Extracellular Matrix for Cardiomyocyte Culture", In Vitro Cellular & Developmental Biology—Animal, Sep. 1996, vol. 21, pp. 478-485.
Vela et al., "Quest for the Cardiovascular Holy Grail: Mammalian Myocardial Regeneration", Cardiovascular Pathology, 2008, vol. 17, No. 1-5.
Ventura et al., "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts", The Journal of Biological Chemistry, May 11, 2007, vol. 282, No. 19, pp. 14243-14252.
Von Harsdorf, R., "Can Cardiomyocytes Divide?" Heart, 2001, vol. 86, pp. 481-482.
Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.
Wagner, Richard, "The State of the Art in Antisense Research", Nature Medicine, Nov. 1995, vol. 1, No. 11, pp. 1116-1118.
Walder et al., "Up-Regulation of Neural Stem Cell Markers Suggests the Occurrence of Dedifferentiation in Regenerating Spinal Cord", Development Genes and Evolution, 2003, vol. 213, pp. 625-630.
Walravens et al., "Cardiosphere-Derived Cell and Mesenchymal Stem Cell Extracellular Vesicles Contain Distinct RNA Cargo", Scientific Program, ISEV2017, Dec. 2017, p. 173.
Wang et al. "The LIM Domain Homeobox Gene isl-1: Conversation of Human, Hamster, and Rat Complementary Deoxyribonucleic Acid Sequences and Expression in Cell Types of Non-neuroendocrine Lineage", Endocrinology, 1994, vol. 134, No. 3, pp. 1416-1422.
Wang et al., "Establishment of New Mouse Embryonic Stem Cell Lines is Improved by Physiological Glucose and Oxygen", Cloning and Stem Cells, 2006, vol. 8, No. 2, pp. 108-116.
Wernig el al., "c-Myc Is Dispensable for Direct Reprogramming of Mouse Fibroblasts", Cell Stem Cell, Jan. 2008, vol. 2, pp. 10-12.
White et al. "Intrinsic Cardiac Origin of Human Cardiosphere-Derived Cells", European Heart Journal, 2013, vol. 34, pp. 68-75.
Wilmut et al., "Viable Offspring Derived from Fetal and Adult Mammalian Cells", Nature, Feb. 27, 1997, vol. 385, pp. 810-813.
Wilson et al., "Bioluminescence Reporter Gene Imaging of Human Embryonic Stem Cell Survival, Proliferation, and Fate", Methods in Molecular Biology, 2009, vol. 574, pp. 87-103.
Wong et al., "Loss of the Y Chromosome: An Age-Related or Clonal Phenomenon in Acute Myelogenous Leukemia/Myelodysplastic Syndrome?" Archives of Pathology & Laboratory Medicine, Aug. 2008, vol. 132, pp. 1329-1332.
Wu et al., "Cellular Therapy and Myocardial Tissue Engineering: The Role of Adult Stem and Progenitor Cells", European Journal of Cardio-Thoracic Surgery, 2006, vol. 30, pp. 770-781.
Yamada et al., "Type V Collagen-Induced Oral Tolerance Plus Low-Dose Cyclosporine Prevents Rejection of MHC Class I and II Incompatible Lung Allografts", The Journal Immunology, Jul. 1, 2009, vol. 183, No. 1, pp. 237-245.
Yang et al., "Human Cardiovascular Progenitor Cells Develop from a KDR$^+$ Embryonic-Stem-Cell-Derived Population", Nature, May 22, 2008, vol. 453, pp. 524-528.
Yau MD et al., "Beneficial Effect of Autologous Cell Transplantation on Infarcted Heart Function: Comparison Between Bone Marrow Stromal Cells and Heart Cells", The Annals of Thoracic Surgery, 2003, vol. 75, No. 1, pp. 169.
Yee et al. "Allogeneic Cardiospheres Delivered via Percutaneous Transendocardial Injection Increase Viable Myocardium, Decrease Scar Size, and Attenuate Cardiac Dilation in Porcine Ischemic Cardiomyopathy", PLOS One, Dec. 2, 2014, pp. 1-29.
Yu et al., "Induced Pluripotent Stem Cell Lines Derived from Human Somatic cells," Science, December 21, 2007, vol. 318, pp. 1917-1920.
Yu et al., "miR-221 and miR-222 Promote Schwann Cell Proliferation and Migration by Targeting LASS2 after Sciatic Nerve Injury", Journal of Cell Science, Jan. 25, 2012, vol. 125, No. 11, pp. 2675-2683.
Zammit et al., "The Skeletal Muscle Satellite Cell: Stem Cell or Son of Stem Cell?" Differentiation, 2001, vol. 68, pp. 193-204.
Zha et al., "Complementary Functions of ATM and H2AX in Development and Suppression of Genomic Instability", Proceedings of the National Academy of Sciences of the United States of America (PNAS), Jul. 8, 2008, vol. 105, No. 27, pp. 9302-9306.
Zhang et al., "Do Cardiac Stem Cells Arise from Cardiomyocyte Dedifferentiation?" Circulation Research, Nov. 2006, vol. 99, No. 11, p. 1278. Abstract only.
Zhao et al., "Targeting Human CD34$^+$ Hematopoietic Stem Cells With Anti-CD45 x Anti-Myosin Light-Chain Bispecific Antibody Preserves Cardiac Function in Myocardial Infarction", Journal of Applied Physiology, Feb. 21, 2008, pp. 1793-1800, vol. 104.
Zhou et al., "Down-Regulation of microRNA-26a Promotes Mouse Hepatocyte Proliferation During Liver Regeneration", PLoS ONE, Apr. 2012, vol. 7, No. 4, e33577, pp. 1-7.
Zhou et al., "Generation of Induced Pluripotent Stem Cells Using Recombinant Proteins", Cell Stem Cell, May 1, 2009, vol. 4, No. 5, pp. 381-384.
Zuo et al., Assessment of Myocardial Blood Perfusion Improved by CD151 in a Pig Myocardial Infarction Model, Acta Pharmacologica Sinica, Jan. 2009, vol. 30, No. 1, pp. 70-77.
Agrahari et al., "How Are We Improving the Delivery to Back of the Eye? Advances and Challenges of Novel Therapeutic Approaches", Expert Opinion on Drug Delivery, 2017, vol. 14, No. 10, pp. 1145-1162.
Aminzadeh et al., "Exosome-Mediated Benefits of Cell Therapy in Mouse and Human Models of Duchenne Muscular Dystrophy", Stem Cell Reports, Mar. 13, 2018, vol. 10, No. 3, pp. 942-955.
Cooper et al., "Immunobiological Barriers to Xenotransplantation", International Journal of Surgery, 2015, vol. 23, pp. 211-216.
Dib et al., "Cell Therapy for Cardiovascular Disease: A Comparison of Methods of Delivery", Journal of Cardiovascular Translational Research, 2011, vol. 4, pp. 177-181.
Gallet et al., "Cardiosphere-Derived Cells Reverse Heart Failure with Preserved Ejection Fraction in Rats by Decreasing Fibrosis and Inflammation", JACC: Basic to Translational Science, Jan. 1, 2016, vol. 1, No. 1-2, pp. 14-28.
Ikehara et al., "Grand Challenges in Stem Cell Treatments", Frontiers in Cell and Developmental Biology, Oct. 10, 2013, vol. 1, No. 2, pp. 2.
Li et al., "IL-6 Contributes to the Defective Osteogenesis of Bone Marrow Stromal Cells from the Vertebral Body of the Glucocorticoid-Induced Osteoporotic Mouse", PLoS ONE, Apr. 29, 2016, vol. 11, No. 4, pp. 19.
Liu et al., "The Immunogenicity and Immune Tolerance of Pluripotent Stem Cell Derivatives", Frontiers in Immunology, Jun. 2017, vol. 3, No. 645, pp. 1-6.

(56) References Cited

OTHER PUBLICATIONS

Makkar et al., "Intracoronary Cardiosphere-Derived Cells for Heart Regeneration After Myocardial Infarction (CADUCEUS): A Prospective, Randomised Phase 1 Trial", Lancet, Mar. 10, 2012, vol. 379, pp. 895-904.
Malliaras et al., "Intracoronary Cardiosphere-Derived Cells After Myocardial Infarction", Journal of the American College of Cardiology, 2014, vol. 63, No. 2, pp. 110-121.
Matsumura, Tsuyoshi, "Cardiaphal Association in Muscular Dystrophy", Nanbyo To Zaitaku Care (Intractable Diseases and Home Care), 2013, vol. 19, No. 8, pp. 55-57.
Naito-Matsui, Yuko, "Lack of Neu5Gc Expression Contributes to the Severity of Duchenne Muscular Dystrophy in Humans", Trends in Glycoscience and Glycotechnology, 2011, vol. 23, No. 132, pp. 194-196.
North et al., "The Intersection Between Aging and Cardiovascular Disease", Circulation Research, Apr. 13, 2012, pp. 1097-1108.
Shi et al., "3,3'-Diindolylmethane Stimulates Exosomal Wnt11 Autocrine Signaling in Human Umbilical Cord Mesenchymal Stem Cells to Enhance Wound Healing", Theranostics, 2017, vol. 7, No. 6, pp. 1674-1688.
Takeda et al., "Induced Pluripotant Stem (IPS) Cell-Based Cell Therapy for Duchenne Muscular Dystrophy", History of Medicine, Dec. 31, 2011, vol. 239, No. 14, pp. 1440-1444.
Tsutsui, Hiroyuki, "Cardiomyopathy: Progress in Diagnosis and Treatments Topics: 1. New classification based on etiology of cardiomyopathy; 1. Classification of cardiomyopathy—its past and present status", The Japanese Society of Internal Medicine, Feb. 2014, vol. 103, No. 2, pp. 277-284.
Wu et al., "Cell Delivery in Cardiac Regenerative Therapy", Ageing Research Reviews, 2012, vol. 11, pp. 32-40.
Aminzadeh et al., "Mitigation of Skeletal Myopathy After Intramyocardial Injection of Cardiosphere-derived Cells in the Mdx Mouse Model of Duchenne Musuclar Dystrophy", Circulation Research, Dec. 4, 2015, No. 22919, pp. e122-e127.
Bryan et al., "Implications of Protein Fold Switching", Current Comments, posted Feb. 4, 2013, printed in 4 pages. https://web.archive.org/web/20160628060217/http://www.elsevierblogs.com/currentcomments/?p=962.
Cheng et al., "Focus on Mesenchymal Stem Cell-Derived Exosomes: Opportunities and Challenges in Cell-Free Therapy", Hindawi, Stem Cells International, 2017, Article ID 6305395, pp. 10.
Edelberg et al., "Platelet-Derived Growth Factor-AB Limits the Extent of Myocardial Infacrction in a Rat Model: Feasibility of Restoring Impaired Angiogenic Capacity in the Aging Heart", Circulation, 2002, vol. 150, No. 5, pp. 608-613.
Fernandez-Aviles et al., "Experimental and Clinical Regenerative Capability of Human Bone Marrow Cells After Myocardial Infarction", Circulation Research, 2004, vol. 95, pp. 742-748.
Heng et al., "Strategies for Directing the Differentiation of Stem Cells into the Cardiomyogenic Lineage in Vitro", Cardiovascular Research, 2004, vol. 62, pp. 34-42.
Hoppe et al., "Distinct Gene-Specific Mechanisms of Arrhythmia Revealed by Cardiac Gene Transfer of Two Long QT Disease Genes, HERG and KCNE1", Proceedings of the National Academy of Sciences of the United States of America, Apr. 24. 2001, vol. 98, No. 9, pp. 5335-5340.
Kobashigawa et al., "A Randomized Active-Controlled Trial of Mycophenolate Mofetil in Heart Transplant Recipients", Transplantation, Aug. 27, 1998, vol. 66, No. 4, pp. 507-515.
Limana et al., "Exogenous High-Mobility Group Box 1 Protein induces Myocardial Regeneration after Infarction via Enhanced Cardiac C-Kit+ Cell Proliferation and Differentiation", Circulation Research, Oct. 14, 2005, vol. 97, No. 8, pp. 73-83.
Maobool et al., The Substrate-Binding Protein in Bacterial ABC Transporters: Dissecting Roles in the Evolution of Substrate Specificity, Biochemical Society Transactions, 2015, vol. 43, Part 5, pp. 1011-1017.
Menasché et al., "Autologous Skeletal Myoblast Transplantation for Severe Postinfarction Left Ventricular Dysfunction", Journal of the American College of Cardiology, vol. 41, No. 7, Apr. 2, 2003, pp. 1078-1083.
Pfeffer et al., "Myocardial Infarct Size and Ventricular Function in Rats", Circulation Research, Apr. 1979, vol. 44, No. 4, pp. 503-512.
Rogers et al., "Intravenous Delivery of Cardiosphere-Derived Cells Improves Striated Muscle Function and Structure in a Murine Model of Duchenne Muscular Dystrophy", The FASEB Journal, Apr. 22-26, 2017, vol. 31, No. S1, pp. 3.
Schächinger et al., "Transplantation of Progenitor Cells and Regeneration Enhancement in Acute Myocardial Infarction: Final One-Year Results of the TOPCARE-AMI Trial", Journal of the American College of Cardiology, Oct. 19, 2004, vol. 44, No. 8, pp. 1690-1699.
Shimasaki et al., "Exosome Research and Co-culture Study", Biological and Pharmaceutical Bulletin, vol. 40, No. 9, 2018, pp. 1311-1321.
Siminiak et al., "Autologous Skeletal Myoblast Trans plantation for the Treatment of Postinfarction Myocardial Injury: Phase I Clinical Study with 12 Months of Follow-Up", American Heart Journal, Sep. 2004, vol. 148, No. 3, pp. 531-537.
Smits et al., "Catheter-Based Intramyocardial Injection of Autologous Skeletal Myoblasts as a Primary Treatment of Ischemic Heart Failure: Clinical Experience with Six-Month Follow-Up", Journal of the American College of Cardiology, 2003, vol. 42, No. 12, pp. 2063-2069.
Strauer et al., "Repair of infarcted Myocardium by Autologous Intracoronary Mononuclear Bone Marrow Cell Transplantation in Humans", Circulation, Oct. 8, 2002, vol. 106, No. 15, pp. 1913-1918.
Taylor et al., "A Randomized, Multicenter Comparison of Tacrolimus and Cyclosporine Immunosuppressive Regimens in Cardiac Transplantation: Decreased Hyperlipidemia and Hypertension with Tacrolimus", Journal Heart Lung Transplant, Apr. 1, 1999, vol. 18, No. 4, pp. 336-345.
Bioptome.com, Scholten Surgical Instruments, Inc., downloaded from http://www.bioptome.com, 2001, first date of publication unknown, printed on Nov. 1, 2005, pp. 2.
Zeger et al., "Longitudinal Data Analysis for Discrete and Continuous Outcomes", Biometrics, Mar. 1986, vol. 42, No. 1, pp. 121-130.
Ibrahim et al., "Augmenting Canonical Wnt Signaling in Therapeutically Inert Cells Converts them into Therapeutically Potent Exosome Factories", Nature Biomedical Engineering, Sep. 2019, vol. 3, pp. 695-705.
Ibrahim et al., "Small Molecule Inhibitors and Culture Conditions Enhance Therapeutic Cell and EV Potency via Activation of Beta-Catenin and Suppression of THY1", Nanomedicine: Nanotechnology, Biology, and Medicine, Dec. 13, 2020, vol. 33, p. 7.
De Couto et al., "Exosomal MicroRNA Transfer into Macrophages Mediates Cellular Postconditioning", Circulation, American Heart Association, vol. 136, No. 2, Jul. 11, 2017, pp. 200-214 (47 pages total).
Anastasiou-Nana et al., "Relative Efficiency and Risk of Endomyocardial Biopsy: Comparisons in Heart Transplant and Nontransplant Patients," Catheter Cardiovascular Diagnosis Journal, Sep. 1989, vol. 18, No. 1, pp. 7-11.
Barile et al., "Beneficial Effects of Exosomes Secreted by Cardiac-Derived Progenitor Cells and Other Cell Types in Myocardial Ischemia", Stem Cell Investigation, Nov. 18, 2017, pp. 93-99.
Carr et al., "Cardiosphere-Derived Cells Improve Function in the Infarcted Rat Heart for at Least 16 Weeks—an MRI Study", PLoS One, Oct. 2011, vol. 6, No. 10, pp. 1-10.
Catalano, Mariadelva, "Engineering Exosomes Toward Folate Receptor Expressing Cells", Dec. 7, 2017, pp. 3.
Chen et al., "Transformation of Cell-Derived Microparticles into Quantum-Dot-Labeled Nanovectors for Antitumor siRNA Delivery", Angewandte Chemie International Edition, vol. 54, No. 3, Nov. 20, 2014, pp. 1036-1040.
Declaration of Rachel Smith, PH.D., Curriculum Vitae, Exhibit A U.S. Appl. No. 13/412,051, 13 pages.
Girard et al., "A Germline-Specific Class of Small RNAs Binds Mammalian Piwi Proteins", Nature, Jul. 13, 2006, vol. 442, pp. 199-202.

(56) References Cited

OTHER PUBLICATIONS

Kasai-Brunswick et al., "Cardiosphere-Derived Cells do not Improve Cardiac Function in Rats with Cardiac Failure," Stem Cell Research & Therapy, 2017, vol. 8, No. 36, 9 pages.
Kim, PhD et al., "Engineering Macrophage-Derived Exosomes for Targeted Paclitaxel Delivery to Pulmonary Metastases:In Vitroandin Vivoevaluations", Nanomedicine, Nanotechnology, Biology, and Medicine, vol. 14, 2018, pp. 195-204.
Kim, PhD et al., "Exosome Mediated Delivery of Paclitaxel for the Treatment of Multi Drug Resistant Pulmonary Metastases", Dissertation, Chapel Hill, Dec. 31, 2016, p. 112.
Li et al., "Skeletal Myoblast-Seeded Vascularized Tissue Scaffolds in the Treatment of a Large Volumetric Muscle Defect in the Rat Biceps Femoris Muscle", Termis, Tissue Engineering: Part A, vol. 23, No. 17 & 18, 2017, pp. 989-1000.
Magarotto et al., "Muscle Functional Recovery is Driven by Extracellular Vesicles Combined with Muscle Extracellular Matrix in a Volumetric Muscle Loss Murine Model", Biomaterials 269, 2021, pp. 1-15.
Mason, "Techniques for Right and Left Ventricular Endomyocardial Biopsy", American Journal of Cardiology, 1978, vol. 41, No. 5, pp. 887-892.
Pilia et al., "Transplantation and Perfusion of Microvascular Fragments in a Rodent Model of Volumetric Muscle Loss Injury", European Cells and Materials, vol. 28, 2014, pp. 11-24.
Shen et al., "The Early Cryptic Transmission and Evolution of SARS-CoV-2 in Human Hosts", Available at SSRN 3724275, Aug. 2019, https://www.oyeyeah.com/wp-content/uploads/2020/11/SSRN-is3724275.pdf, p. 22.
Sicari et al., "An Acellular Biologic Scaffold Promotes Skeletal Muscle Formation in Mice and Humans with Volumetric Muscle Loss", Science Translational Medicine, Apr. 30, 2014, vol. 6, No. 234, pp. 1-10.
Smyth et al., "Surface Functionalization of Exosomes Using Click Chemistry", Bioconjugate Chemistry, vol. 25, No. 10, Sep. 30, 2014, pp. 1777-1784.
USPTO Patent Trial and Appeal Board., "Decision on Appeal", in U.S. Appl. No. 13/412,051, dated Jun. 8, 2020, 12 pages.
USPTO Patent Trial and Appeal Board., "Declaration of Rachel R. Smith, PhD," in U.S. Appl. No. 13/412,051, dated Oct. 13, 2017, 32 pages.
Vella et al., "PIWI-lnteracting RNA (piRNA) Signatures in Human Cardiac Progenitor Cells", The International Journal of Biochemistry & Cell Biology, 2016, vol. 76, pp. 1-11.
Wan et al., "Aptamer-Conjugated Extracellular Nanovesicles for Targeted Drug Delivery", Cancer Research, vol. 78, No. 3, Dec. 7, 2017, pp. 798-808.
Wang et al., "The Use of RGD-Engineered Exosomes for Enhanced Targeting Ability and Synergistic Therapy Toward Angiogenesis", Nanoscale, vol. 9, No. 40, Jan. 1, 2017, pp. 15598-15605.
Wang et al., Challenges in the Development and Establishment of Exosome-Based Drug Delivery Systems, Journal of Controlled Release, 2021, vol. 329, pp. 894-906.
Zhang et al., "Magnetic and Folate Functionalization Enables Rapid Isolation and Enhanced Tumor-Targeting of Cell-Derived Microvesicles", ACS Nano, vol. 11, No. 1, Jan. 24, 2017, pp. 277-290.
Zhao et al., "Exosomes as Drug Carriers for Cancer Therapy and Challenges Regarding Exosome Uptake" Biomedicine & Pharmacotherapy, 2020, vol. 128, 9 pages.

\* cited by examiner

Day 0

Day 15

C)

D)

C)

D)

Figures 12A-12D
A) Control          B) NHDF-XO
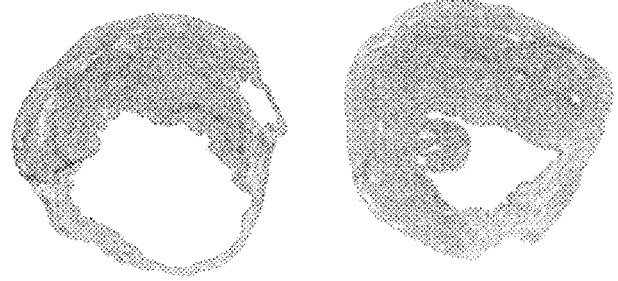
C) MSC-XO           D) CDC-XO

E)

F)

A)

B)

A) CDC-GW4869    B) CDC-DMSO

*Figure 18B*

| | | | |
|---|---|---|---|
| miR-26a | miR-425 | miR-25 | miR-146a |
| miR-125b | miR-223 | miR-100 | miR-210 |
| let-7e | miR-141 | miR-93 | miR-22 |
| let-7a | miR-7 | miR-302b | miR-24 |
| let-7c | miR-32 | miR-142-5p | miR-150 |
| miR-125a-5p | miR-124 | miR-142-3p | miR-140-3p |
| miR-155 | miR-29a | miR-122 | miR-19a |
| let-7b | miR-194 | miR-191 | miR-27b |
| miR-23b | miR-16 | miR-181b | miR-19b |
| miR-30c | miR-101 | miR-30a | miR-27a |
| miR-181a | miR-186 | miR-30d | miR-376c |
| miR-29b | miR-195 | miR-140-5p | miR-320a |
| let-7g | mir-15b | miR-17 | miR-130a |
| miR-196b | miR-92a | miR-302a | miR-9 |
| miR-28-5p | miR-144 | let-7i | miR-128 |
| miR-374a | miR-222 | miR-200c | miR-143 |
| let-7f | miR-29c | miR-30e | miR-21 |
| miR-26b | miR-18a | miR-30b | miR-185 |
| miR-423-5p | miR-106b | miR-302c | miR-23a |
| miR-151-5p | miR-96 | miR-20a | |
| miR-15a | miR-126 | | |
| miR-103 | miR-424 | | |
| miR-99a | miR-28-3p | | |
| let-7d | | | |
| 10-fold or greater downregulation | Unchanged | | 10-fold or greater upregulation |

A)

B)   C)

miR control   miR-146a

D)

E)

F)

G)

EXOSOMES AND MICRO-RIBONUCLEIC ACIDS FOR TISSUE REGENERATION

RELATED APPLICATIONS

This application is a divisional application of U.S. application Ser. No. 15/790,962, filed Oct. 23, 2017, which is divisional application of U.S. application Ser. No. 14/421,355, filed Feb. 12, 2015, which is the U.S. National Phase entry under 35 U.S.C. § 371 of International Application No. PCT/US2013/054732, filed Aug. 13, 2013, which claims the benefit of U.S. Provisional Application No. 61/682,666, filed Aug. 13, 2012, the entire disclosures of each of which is hereby incorporated by reference herein.

STATEMENT REGARDING GOVERNMENT SPONSORED GRANT

The inventions disclosed herein were made with Government support under the Research Project Grant (ROI HL083109) by the National Institutes of Health. The United States Government has certain rights in this invention.

BACKGROUND

The present application relates generally to methods and compositions for the repair or regeneration of damaged or diseased cells or tissue. Several embodiments relate to administration of exosomes (or protein and/or nucleic acids from the exosomes) isolated from cells or synthetic surrogates in order to repair and/or regenerate damage or diseased tissues. In particular, several embodiments, relate to exosomes derived from certain cell types, such as for example cardiac stem cells, and use of the exosomes in the repair and/or regeneration of cardiac tissue.

Description of the Related Art

Many diseases, injuries and maladies involve loss of or damage to cells and tissues. Examples include, but are not limited to neurodegenerative disease, endocrine diseases, cancers, and cardiovascular disease. Just these non-limiting examples are the source of substantial medical costs, reduced quality of life, loss of productivity in workplaces, workers compensation costs, and of course, loss of life. For example, coronary heart disease is one of the leading causes of death in the United States, taking more than 650,000 lives annually. Approximately 1.3 million people suffer from a heart attack (or myocardial infarction, MI) every year in the United States (roughly 800,000 first heart attacks and roughly 500,000 subsequent heart attacks). Even among those who survive the MI, many will still die within one year, often due to reduced cardiac function, associated side effects, or progressive cardiac disease. Heart disease is the leading cause of death for both men and women, and coronary heart disease, the most common type of heart disease, led to approximately 400,000 deaths in 2008 in the US. Regardless of the etiology, most of those afflicted with coronary heart disease or heart failure have suffered permanent heart tissue damage, which often leads to a reduced quality of life.

SUMMARY

There exists a need for methods and compositions to repair and/or regenerate tissue that has been damaged (or is continuing to undergo damage) due to injury, disease, or combinations thereof. While classical therapies such as pharmacological intervention or device-based intervention or surgery provide positive effects, there are provided herein methods and compositions that yield unexpectedly beneficial effects in the repair or regeneration of damaged or diseased tissues (though in some embodiments, these methods and compositions are used to complement classical therapies).

As such, there are provided herein methods for regenerating tissue in an individual having damaged tissue, comprising, identifying an individual having damaged tissue and administering a plurality of exosomes to the individual, wherein the exosomes are secreted from regenerative cells, wherein the exosomes comprise one or more microRNA fragments, and wherein after administration of the plurality of exosomes, the one or more microRNA fragments alter gene expression in the damaged tissue, improve the viability of the damaged tissue, and/or facilitate the formation of new tissue in the individual. In several embodiments, administration of the exosomes results in functional improvement in the tissue, in combination with one or more of the above-mentioned positive results. In several embodiments, the exosomes are synthetic in origin. In some such embodiments, the synthetic exosomes are generated in order to replicate, substantially, or closely mimic exosomes that are secreted from regenerative cells.

In several embodiments, the regenerative cells are mammalian in origin. In several embodiments, the regenerative cells are human cells. In some embodiments, the cells are non-embryonic human regenerative cells. In several embodiments, the regenerative cells are autologous to the individual while in several other embodiments the regenerative cells are allogeneic to the individual. Xenogeneic or syngeneic cells are used in certain other embodiments.

In several embodiments, there is provided a method of regenerating tissue in an individual having damaged tissue, comprising identifying an individual having damaged tissue and administering one or more microRNA fragments, or derivatives thereof, to the individual, wherein after administration of the one or more microRNA fragments, the one or more microRNA fragments alter gene expression in the damaged tissue, improve the viability of the damaged tissue, and/or facilitate the formation of new tissue in the individual. Thus, in some embodiments, exosomes need not be administered, but rather miRNAs (and/or proteins) that are thought to or known to be present in a certain exosome, can be directly administered to effect regeneration of damaged tissue. In several such embodiments, the microRNA fragments, or derivatives thereof, are synthetically generated. In one embodiment, the microRNA fragments, or derivatives thereof are synthesized with a sequence that mimics one or more endogenous microRNA molecules. Alternatively, in several embodiments, miRNAs are complementary to certain genes in the target cell and can reduce the expression of target genes. Combinations of complementary miRNAs (e.g., antisense molecules known as antagomiRs) and miRNAs (or miRNA mimics) are used in several embodiments. In several embodiments, modifications (e.g., chemical modifications) are made in order to enhance the stability of the microRNAs, thereby improving the ability to administer the microRNA (or fragments/derivatives thereof). In some embodiments, administration is of only microRNA fragments, mimics thereof, derivatives thereof, or chemical replicas thereof, or combinations thereof (e.g., no exosomes). However, in several embodiments, as discussed herein, administration comprises administration of a plurality of synthetic liposomes that comprise the one or more microRNA fragments, or derivatives thereof. In additional embodiments, a plurality of regenerative cells is administered along with exosomes, and/or miRNAs.

In several embodiments, the damaged tissue comprises cardiac tissue. In several embodiments, the regenerative cells comprise cardiospheres. In several embodiments, the regenerative cells comprise cardiosphere-derived cells (CDCs). In several embodiments, the use of cardiospheres and/or CDCs as a source of exosomes is particularly advantageous, as the resultant exosomes provide unexpectedly superior therapeutic benefits (as compared to exosomes from other cell types). In some embodiments, such benefits include, but are not limited to, reduced degradation, enhanced specificity for cardiac regeneration, lower immunogenicity, etc. Additionally, in several embodiments, the cardiospheres and or CDCs are screened to identify an miRNA expression profile that is unique to those cells. That profile, in several embodiments, is replicated, at least in part, by the generation and administration of synthetic exosomes and/or miRNAs. Thus, the therapeutic efficacy of cardiospheres and/or CDCs can unexpectedly be mirrored, without administration of the cells themselves. In several embodiments, this results in improved therapeutic efficacy as the exosomes and/or miRNAs result in reduced immune response in the target tissue.

In several embodiments, the damaged tissue comprises one or more of neural and/or nervous tissue, epithelial tissue, skeletal muscle tissue, endocrine tissue, vascular tissue, smooth muscle tissue, liver tissue, pancreatic tissue, lung tissue, intestinal tissue, osseous tissue, connective tissue, or combinations thereof. In several embodiments, the damaged tissue is in need of repair, regeneration, or improved function due to an acute event. Acute events include, but are not limited to, trauma such as laceration, crush or impact injury, shock, loss of blood or oxygen flow, infection, chemical or heat exposure, poison or venom exposure, drug overuse or overexposure, and the like. For example, in several embodiments, the damaged tissue is cardiac tissue and the acute event comprises a myocardial infarction. In some embodiments, administration of the exosomes results in an increase in cardiac wall thickness in the area subjected to the infarction. In additional embodiments, the tissue is damaged due to chronic disease or ongoing injury. For example, progressive degenerative diseases can lead to tissue damage that propagates over time (at times, even in view of attempted therapy). Chronic disease need not be degenerative to continue to generate damaged tissue, however. In several embodiments, chronic disease/injury includes, but it not limited to epilepsy, Alzheimer's disease, Parkinson's disease, Huntington's disease, dopaminergic impairment, dementia, ischemia including focal cerebral ischemia, ensuing effects from physical trauma (e.g., crush or compression injury in the CNS), neurodegeneration, immune hyperactivity or deficiency, bone marrow replacement or functional supplementation, arthritis, auto-immune disorders, inflammatory bowel disease, cancer, diabetes, muscle weakness (e.g., muscular dystrophy, amyotrophic lateral sclerosis, and the like), blindness and hearing loss. Cardiac tissue, in several embodiments, is also subject to damage due to chronic disease, such as for example congestive heart failure, ischemic heart disease, diabetes, valvular heart disease, dilated cardiomyopathy, infection, and the like. Other sources of damage also include, but are not limited to, injury, age-related degeneration, cancer, and infection. In several embodiments, the regenerative cells are from the same tissue type as is in need of repair or regeneration. In several other embodiments, the regenerative cells are from a tissue type other than the tissue in need of repair or regeneration. In several embodiments, the regenerative cells comprise somatic cells, while in additional embodiments, they comprise germ cells. In still additional embodiments, combinations of one or more cell types are used to obtain exosomes (or the contents of the exosomes).

In several embodiments, the exosomes are about 15 nm to about 95 nm in diameter, including about 15 nm to about 20 nm, about 20 nm to about 25 nm, about 25 nm to about 30 nm, about 30 nm to about 35 nm, about 35 nm to about 40 nm, about 40 nm to about 50 nm, about 50 nm to about 60 nm, about 60 nm to about 70 nm, about 70 nm to about 80 nm, about 80 nm to about 90 nm, about 90 nm to about 95 nm and overlapping ranges thereof. In certain embodiments, larger exosomes are obtained are larger in diameter (e.g., those ranging from about 140 to about 210 nm). Advantageously, in several embodiments, the exosomes comprise synthetic membrane bound particles (e.g., exosome surrogates), which depending on the embodiment, are configured to a specific range of diameters. In such embodiments, the diameter of the exosome surrogates is tailored for a particular application (e.g., target site or route of delivery). In still additional embodiments, the exosome surrogates are labeled or modified to enhance trafficking to a particular site or region post-administration.

In several embodiments, exosomes are obtained via centrifugation of the regenerative cells. In several embodiments, ultracentrifugation is used. However, in several embodiments, ultracentrifugation is not used. In several embodiments, exosomes are obtained via size-exclusion filtration of the regenerative cells. As disclosed above, in some embodiments, synthetic exosomes are generated, which can be isolated by similar mechanisms as those above.

In several embodiments, the exosomes induce altered gene expression by repressing translation and/or cleaving mRNA. In some embodiments, the alteration of gene expression results in inhibition of undesired proteins or other molecules, such as those that are involved in cell death pathways, or induce further damage to surrounding cells (e.g., free radicals). In several embodiments, the alteration of gene expression results directly or indirectly in the creation of desired proteins or molecules (e.g., those that have a beneficial effect). The proteins or molecules themselves need not be desirable per se (e.g., the protein or molecule may have an overall beneficial effect in the context of the damage to the tissue, but in other contexts would not yield beneficial effects). In some embodiments, the alteration in gene expression causes repression of an undesired protein, molecule or pathway (e.g., inhibition of a deleterious pathway). In several embodiments, the alteration of gene expression reduces the expression of one or more inflammatory agents and/or the sensitivity to such agents. Advantageously, the administration of exosomes, or miRNAs, in several embodiments, results in downregulation of certain inflammatory molecules and/or molecules involved in inflammatory pathways. As such, in several embodiments, cells that are contacted with the exosomes or miRNAs enjoy enhanced viability, even in the event of post-injury inflammation or inflammation due to disease.

In several embodiments, the exosomes fuse with one or more recipient cells of the damaged tissue. In several embodiments, the exosomes release the microRNA into one or more recipient cells of the damaged tissue, thereby altering at least one pathway in the one or more cells of the damaged tissue. In some embodiments, the exosomes exerts their influence on cells of the damaged tissue by altering the environment surrounding the cells of the damaged tissue. In some embodiments, signals generated by or as a result of the content or characteristics of the exosomes, lead to increases or decreases in certain cellular pathways. For example, the exosomes (or their contents/characteristics) can alter the cellular milieu by changing the protein and/or lipid profile, which can, in turn, lead to alterations in cellular behavior in this environment. Additionally, in several embodiments, the miRNA of an exosome can alter gene expression in a recipient cell, which alters the pathway in which that gene was involved, which can then further alter the cellular environment. In several embodiments, the influence of the exosomes directly or indirectly stimulates angiogenesis. In several embodiments, the influence of the exosomes directly or indirectly affects cellular replication. In several embodiments, the influence of the exosomes directly or indirectly inhibits cellular apoptosis.

The beneficial effects of the exosomes (or their contents) need not only be on directly damaged or injured cells. In some embodiments, for example, the cells of the damaged tissue that are influenced by the disclosed methods are healthy cells. However, in several embodiments, the cells of the damaged tissue that are influenced by the disclosed methods are damaged cells.

In several embodiments, regeneration comprises improving the function of the tissue. For example, in certain embodiments in which cardiac tissue is damaged, functional improvement may comprise increased cardiac output, contractility, ventricular function and/or reduction in arrhythmia (among other functional improvements). For other tissues, improved function may be realized as well, such as enhanced cognition in response to treatment of neural damage, improved blood-oxygen transfer in response to treatment of lung damage, improved immune function in response to treatment of damaged immunological-related tissues.

In several embodiments, the microRNA fragments are selected from the group consisting of miR-23a, miR-23b, miR-24, miR-26a, miR27-a, miR-30c, let-7e, mir-19b, miR-125b, mir-27b, let-7a, miR-19a, let-7c, miR-140-3p, miR-125a-5p, miR-132, miR-150, miR-155, mir-210, let-7b, miR-24, miR-423-5p, miR-22, let-7f, miR-146a, and combinations thereof. In several embodiments, one, two, three or more of these miRNAs are used to treat cardiac tissue. In one embodiment, the microRNA comprises miR-146a. In one embodiment, the microRNA comprises miR-210. In additional embodiments, the miRNA comprises one or more of miR-17, miR-21, miR-92, miR92a, miR-29, miR-29a, miR-29b, miR-29c, miR-34, mi-R34a, miR-150, miR-451, miR-145, miR-143, miR-144, miR-193a-3p, miR-133a, miR-155, miR-181a, miR-214, miR-199b, miR-199a, miR-210, miR-126, miR-378, miR-363 and miR-30b, and miR-499. In several embodiments, exosomes do not contain any of miR-92, miR-17, miR-21, miR-92, miR92a, miR-29, miR-29a, miR-29b, miR-29c, miR-34, mi-R34a, miR-150, miR-451, miR-145, miR-143, miR-144, miR-193a-3p, miR-133a, miR-155, miR-181a, miR-214, miR-199b, miR-199a, miR-126, miR-378, miR-363 and miR-30b, or miR-499. In several embodiments, the exosomes further comprise at least one protein that further facilitates regeneration and/or improved function of the tissue.

Administration can be via a variety of routes, depending on the embodiment. For example, in some embodiments, delivery is locally to the tissue. In some embodiments, delivery is systemically. In one embodiment, delivery is via an intramyocardial route, while in other embodiments, delivery is via an intracoronary route. Combinations of delivery routes are used, in certain embodiments, in order to improve the speed with which positive effects are realized and or improve the duration of treatment. For example, in some embodiments, miRNAs are delivered directly to a target tissue and exosomes are delivered via a systemic route.

In several embodiments, the method further comprises administering the regenerative cells from which the exosomes were obtained to the individual, either prior to, concurrent with, or after administration of the exosomes. Administration of these cells can be by the same route or an alternative route.

In several embodiments, there is provided a composition for the repair or regeneration of damaged or diseased cardiac tissue comprising, a plurality of exosomes isolated from a population of cardiac stem cells, wherein the cardiac stem cells comprise a population of cardiosphere-derived cells, wherein the exosomes comprise at least one microRNA, wherein the microRNA is selected from the group consisting of miR-146a, miR-22, miR-24, and miR-26a, and wherein upon administration to a subject having damaged or diseased cardiac tissue, the exosomes increase one or more of cardiac cell viability, cardiac cell proliferation, and cardiac cell function. In one embodiment, the composition further comprises a plurality of cardiac stem cells. In one embodiment, the miRNA payload of the exosome comprises, consists of, or consists essentially of miR-146a. In one embodiment, the miRNA payload of the exosome comprises, consists of, or consists essentially of miR-210. In several embodiments, there is provided a use of a composition comprising a plurality of exosomes isolated from a population of cardiosphere-derived cells for the treatment of damaged or diseased cardiac tissue. In several embodiments, there is provided a use of a composition comprising a plurality of miRNA, a plurality of exosome, and/or a plurality of cardiosphere-derived cells for the treatment of damaged or diseased cardiac tissue.

There is also provided a composition for the repair or regeneration of damaged or diseased cardiac tissue comprising synthetic microRNA-146a and a pharmaceutically acceptable carrier. In one embodiment, the synthetic miRNA consists of or consists essentially of miR-146a. In some embodiments, the synthetic miRNA also comprises a synthetic miR210. In one embodiment, the synthetic miRNA consists of or consists essentially of miR-210. In some embodiments, the microRNA is directly administered, while in some embodiments, it is administered via delivery of an exosome (either isolated or synthetically generated).

In several embodiments, there is provided a method comprising identifying a subject in need of repair of damaged tissue and instructing the administration of a composition comprising exosomes derived from regenerative cells to the subject, thereby resulting in repair of the damaged tissue.

In several embodiments, there is provided a method comprising identifying a subject in need of repair of damaged tissue and instructing the administration of a composition comprising one or more miRNA to the subject, thereby resulting in repair of the damaged tissue.

In several embodiments, there is provided a method comprising identifying a subject in need of repair of damaged tissue and instructing the administration of a composition comprising one or more of exosomes derived from regenerative cells, miRNA, and regenerative cells to the subject, thereby resulting in repair of the damaged tissue.

In several such embodiments, the repair of the damaged tissue comprises both anatomical repair (e.g., tissue regeneration) and functional repair.

In several embodiments, there is provided a method of generating exosomes, comprising obtaining a population of non-embryonic human regenerative cells, culturing the population of non-embryonic human regenerative cells, and exposing the cultured population of non-embryonic human regenerative cells to a hydrolase enzyme to induce the cells to secrete exosomes, thereby generating exosomes. In several embodiments, the method further comprises harvesting the secreted exosomes. In several embodiments, the hydrolase comprises a member of the DNAse I superfamily of enzymes. In several embodiments, the hydrolase comprises a sphingomyelinase, such as for example a sphingomyelinase of a type selected from the group consisting of lysosomal acid sphingomyelinase, secreted zinc-dependent acid sphingomyelinase, neutral sphingomyelinase, and alkaline sphingomyelinase. In several embodiments, a neutral sphingomyelinase is used. In one embodiment, the neutral sphingomyelinase comprises one or more of magnesium-dependent neutral sphingomyelinase and magnesium-independent neutral sphingomyelinase. In additional embodiments, the neutral sphingomyelinase comprises one or more of neutral sphingomyelinase type I, neutral sphingomyelinase type 2, and neutral sphingomyelinase type 3. As discussed above, in several embodiments the exosomes are synthetically manufactured in vitro by established methods to generate lipid bilayers. In such embodiments, the synthetic exosomes can advantageously be customized to regenerate a certain tissue type and optionally damage due to a specific source of damage.

The methods summarized above and set forth in further detail below describe certain actions taken by a practitioner; however, it should be understood that they can also include the instruction of those actions by another party. Thus, actions such as "administering exosomes" include "instructing the administration of exosomes."

BRIEF DESCRIPTION OF THE DRAWINGS

FIG. 2A depicts a schematic for the isolation of exosomes from cultured cells according to several embodiments disclosed herein. FIG. 2B depicts the survival of CDCs in serum free culture conditions prior in preparation for exosome isolation. FIGS. 2C and 2D show bright-field microscopic images of CDCs at Day 0 and Day 15 (respectively) of culture in serum-free conditions.

FIG. 3A depicts data related to the RNA content of the supernatant and exosome fractions of cells. FIG. 3B shows data related to the number of exosomes generated from the isolation scheme outlined in FIG. 2A. FIG. 3C shows differences in expression of various surface genes on NHDF and CDCs. FIG. 3D shows microscopic images of exosomes. FIG. 3E depicts analysis of the frequency of exosomes as compared to their diameter.

FIG. 5A shows data related to apoptosis of cells after incubation with exosomes from various sources. FIG. 5B shows data related to proliferative activity of cells after incubation with exosomes from various sources. FIG. 5C shows immunofluorescent TUNEL staining that depicts apoptosis of cells after exposure to various exosome compositions. FIG. 5D shows immunofluorescent Ki-67 staining that depicts proliferative activity of cells after exposure to various exosome compositions.

FIGS. 12A-12H depict data related to the anatomical improvements in cardiac tissue after exosome administration. FIGS. 12A-12D depict Masson's trichrome staining data after myocardial infarction and treatment with exosome preparations from various cell sources. Summary data related to tissue viability scar mass, viable mass, and wall thickness are shown in FIGS. 12E-12H, respectively.

FIG. 14A depicts dose-response data related to inhibition of secretion of CDC-derived exosomes with a neutral sphingomyelinase inhibitor (GW4869). FIG. 14B indicates cell viability in response to inhibition of exosome secretion. FIG. 1 4C summarizes cardiac functional data after administration of exosomes derived from control cells or cells treated with a neutral sphingomyelinase inhibitor (GW4869).

FIGS. 18A-18B depicts profiling of miRNA expression from exosomes isolated from CDCs, as compared to control cells (normal human dermal fibroblast: NHDF). FIG. 18A depicts relative expression of selected miRNAs in exosomes from CDCs as compared to NHDF cells. FIG. 18B shows a listing of those miRNAs that are equivalently expressed in NHDF and CDCs, those that are significantly upregulated, and those that are significantly downregulated.

FIG. 19 depicts a schematic for an in vitro study to determine the effects of administration of mi146a.

FIG. 20A depicts results of calcein staining to evaluate cell viability 6 hours after NRVM were transfected with miR146a. FIG. 20B depicts results of ETHD-1 staining to evaluate cell viability 12 hours after NRVM were transfected with miR146a. FIG. 20C depicts data showing the protective effects of miR146a on NRVM exposed to hydrogen peroxide. FIG. 20D depicts data showing the protective effects of miR146a on NRVMs exposed to cobalt chloride.

FIGS. 21A-21G relate to in vivo data showing the regenerative capacity of miR146a. FIG. 21A shows two infarcted hearts, while 21B shows Masson's Trichrome of a heart treated with control mimic miRNA and 21C shows Masson's Trichrome of a heart treated with miR146a. FIG. 21D shows the ejection fraction in control and treated mice over 30 days post-MI. FIGS. 21E, 21F, and 21G show overall viable tissue mass, scar mass, and wall thickness (respectively) of hearts from animals treated with miR146a or a control mimic miR.

FIG. 22 shows expression data related to known inflammatory molecules in cultured cardiomyocytes transfected with miR146a.

DETAILED DESCRIPTION

Figure 1:
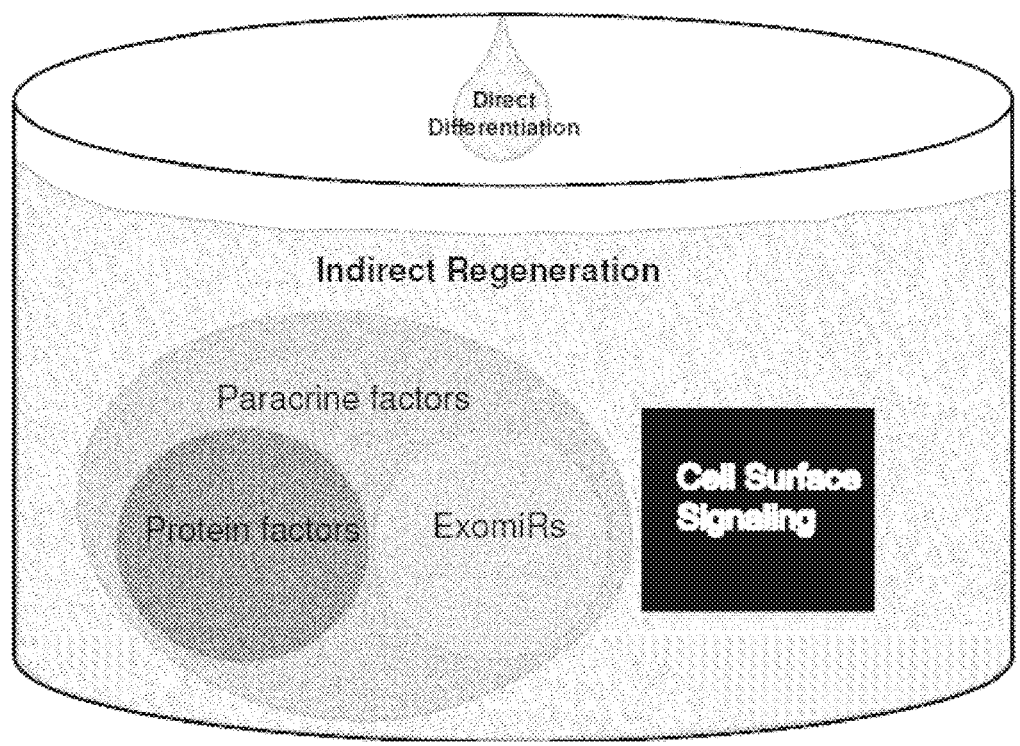
FIG. 1 depicts a general schematic of the various components of cellular and tissue regeneration, including direct and indirect mechanisms.

Several embodiments of the methods and compositions disclosed herein are useful for the treatment of tissues that are damaged or adversely affected by disease(s). The vast majority of diseases lead to at least some compromise (even if acute) in cellular or tissue function. Several embodiments of the methods and compositions disclosed herein allow for repair and/or regeneration of cells and/or tissues that have been damaged, limited in their functionality, or otherwise compromised as a result of a disease. In several embodiments, methods and compositions disclosed herein may also be used as adjunct therapies to ameliorate adverse side effects of a disease treatment that negatively impacts cells or tissues.

Treatment Modalities for Damaged or Diseased Tissues

Generally, the use of one or more relatively common therapeutic modalities are used to treat damaged or diseased tissues in an effort to halt progression of the disease, reverse damage that has already occurred, prevent additional damage, and generally improve the well-being of the patient. For example, many conditions can be readily treated with holistic methodologies or changes in lifestyle (e.g., improved diet to reduce risk of cardiovascular disease, diabetes, and the like). Often more serious conditions require more advanced medical intervention. Drug therapy or pharmaceutical therapies are routinely administered to treat patients suffering from a particular disease. For example, a patient suffering from high blood pressure might be prescribed an angiotensin-converting-enzyme (ACE) inhibitor, in order to reduce the tension of blood vessels and blood volume, thereby treating high blood pressure. Further, cancer patients are often prescribed panels of various anticancer compounds in an attempt to limit the spread and/or eradicate a cancerous tumor. Surgical methods may also be employed to treat certain diseases or injuries. In some cases, implanted devices are used in addition to or in place of pharmaceutical or surgical therapies (e.g., a cardiac pacemaker). Recently, additional therapy types have become very promising, such as, for example, gene therapy, protein therapy, and cellular therapy.

Cell therapy, generally speaking, involves the administration of population of cells to subject with the intent of the administered cells functionally or physically replacing cells that have been damaged, either by injury, by disease, or combinations thereof. A variety of different cell types can be administered in cell therapy, with stem cells being particularly favored (in certain cases) due to their ability to differentiate into multiple cell types, thus providing flexibility for what disease or injury they could be used to treat.

Protein therapy involves the administration of exogenous proteins that functionally replace deficient proteins in the subject suffering from a disease or injury. For example, synthesized acid alpha-glucosidase is administered to patients suffering from glycogen storage disease type II.

In addition, nucleic acid therapy is being investigated as a possible treatment for certain diseases or conditions. Nucleic acid therapy involves the administration of exogenous nucleic acids, or short fragments thereof, to the subject in order to alter gene expression pathways through a variety of mechanisms, such as, for example, translational repression of the target gene, cleavage of a target gene, such that the target gene product is never expressed.

With the knowledge that certain cellular therapies provide profound regenerative effects, several embodiments disclosed herein involve methods and compositions that produce those regenerative effects without the need for administration of cells to a subject (though cells may optionally be administered in certain embodiments).

Exosomes and Vesicle Bound Nucleic Acid and Protein Products

Nucleic acids are generally not present in the body as free nucleic acids, as they are quickly degraded by nucleases. Certain types of nucleic acids are associated with membrane-bound particles. Such membrane-bound particles are shed from most cell types and consist of fragments of plasma membrane and contain DNA, RNA, mRNA, microRNA, and proteins. These particles often mirror the composition of the cell from which they are shed. Exosomes are one type of such membrane bound particles and typically range in diameter from about 15 nm to about 95 nm in diameter, including about 15 nm to about 20 nm, 20 nm to about 30 nm, about 30 nm to about 40 nm, about 40 nm to about 50 nm, about 50 nm to about 60 nm, about 60 nm to about 70 nm, about 70 nm to about 80 nm, about 80 nm to about 90 nm, about 90 nm to about 95 nm, and overlapping ranges thereof. In several embodiments, exosomes are larger (e.g., those ranging from about 140 to about 210 run, including about 140 nm to about 150 nm, 150 nm to about 160 run, 160 nm to about 170 run, 170 nm to about 180 nm, 180 nm to about 190 run, 190 nm to about 200 run, 200 nm to about 210 nm, and overlapping ranges thereof). In some embodiments, the exosomes that are generated from the original cellular body are 100, 200, 300, 400, 500, 600, 700, 800, 900, 1000, 2000, 5000, 10,000 times smaller in at least one dimension (e.g., diameter) than the original cellular body.

Alternative nomenclature is also often used to refer to exosomes. Thus, as used herein the term "exosome" shall be given its ordinary meaning and may also include terms including microvesicles, epididimosomes, argosomes, exosome-like vesicles, microparticles, promininosomes, prostasomes, dexosomes, texosomes, dex, tex, archeosomes and oncosomes. Exosomes are secreted by a wide range of mammalian cells and are secreted under both normal and pathological conditions. Exosomes, in some embodiments, function as intracellular messengers by virtue of carrying mRNA, miRNA or other contents from a first cell to another cell (or plurality of cells). In several embodiments, exosomes are involved in blood coagulation, immune modulation, metabolic regulation, cell division, and other cellular processes. Because of the wide variety of cells that secret exosomes, in several embodiments, exosome preparations can be used as a diagnostic tool (e.g., exosomes can be isolated from a particular tissue, evaluated for their nucleic acid or protein content, which can then be correlated to disease state or risk of developing a disease).

Exosomes, in several embodiments, are isolated from cellular preparations by methods comprising one or more of filtration, centrifugation, antigen-based capture and the like. For example, in several embodiments, a population of cells grown in culture are collected and pooled. In several embodiments, monolayers of cells are used, in which case the cells are optionally treated in advance of pooling to improve cellular yield (e.g., dishes are scraped and/or enzymatically treated with an enzyme such as trypsin to liberate cells). In several embodiments, cells grown in suspension are used. The pooled population is then subject to one or more rounds of centrifugation (in several embodiments ultracentrifugation and/or density centrifugation is employed) in order to separate the exosome fraction from the remainder of the cellular contents and debris from the population of cells. In some embodiments, centrifugation need not be performed to harvest exosomes. In several embodiments, pre-treatment of the cells is used to improve the efficiency of exosome capture. For example, in several embodiments, agents that increase the rate of exosome secretion from cells are used to improve the overall yield of exosomes. In some embodiments, augmentation of exosome secretion is not performed. In some embodiments, size exclusion filtration is used in conjunction with, or in place of centrifugation, in order to collect a particular size (e.g., diameter) of exosome. In several embodiments, filtration need not be used. In still additional embodiments, exosomes (or subpopulations of exosomes are captured by selective identification of unique markers on or in the exosomes (e.g., transmembrane proteins)). In such embodiments, the unique markers can be used to selectively enrich a particular exosome population. In some embodiments, enrichment, selection, or filtration based on a particular marker or characteristic of exosomes is not performed.

Upon administration (discussed in more detail below) exosomes can fuse with the cells of a target tissue. As used herein, the term "fuse" shall be given its ordinary meaning and shall also refer to complete or partial joining, merging, integration, or assimilation of the exosome and a target cell. In several embodiments, the exosomes fuse with healthy cells of a target tissue. In some embodiments, the fusion with healthy cells results in alterations in the healthy cells that leads to beneficial effects on the damaged or diseased cells (e.g., alterations in the cellular or intercellular environment around the damaged or diseased cells). In some embodiments, the exosomes fuse with damaged or diseased cells. In some such embodiments, there is a direct effect on the activity, metabolism, viability, or function of the damaged or diseased cells that results in an overall beneficial effect on the tissue. In several embodiments, fusion of the exosomes with either healthy or damaged cells is not necessary for beneficial effects to the tissue as a whole (e.g., in some embodiments, the exosomes affect the intercellular environment around the cells of the target tissue). Thus, in several embodiments, fusion of the exosome to another cell does not occur. In several embodiments, there is no cell-exosome contact, yet the exosomes still influence the recipient cells.

Administration and Therapy

There are provided herein methods and compositions for use in the repair or regeneration of cells or tissue after the cells or tissue have been subject to injury, damage, disease, or some other event that leads to loss of function and/or viability. Methods and compositions for preventing damage and/or for shuttling nucleic acids (or proteins) between cells are also provided, regardless of whether tissue damage is present.

In addition, methods are provided for facilitating the generation of exosomes. In several such embodiments, a hydrolase is used to facilitate the liberation (e.g., secretion) of exosomes from cells. In certain embodiments, hydrolases that cleave one or more of ester bonds, sugars (e.g., DNA), ether bonds, peptide bonds, carbon-nitrogen bonds, acid anhyrides, carbon-carbon bonds, halide bonds, phosphorous-nitrogen bonds, sulpher-nitrogen bonds, carbon-phosphorous bonds, sulfur-sulfur bonds, and/or carbon-sulfur bonds are used. In some embodiments, the hydrolases are DNAses (e.g., cleave sugars). Certain embodiments employ specific hydrolases, such as for example, one or more of lysosomal acid sphingomyelinase, secreted zinc-dependent acid sphingomyelinase, neutral sphingomyelinase, and alkaline sphingomyelinase.

In several embodiments, exosomes are administered to a subject in order to initiate the repair or regeneration of cells or tissue. In several embodiments, the exosomes are derived from a stem cell. In several embodiments, the stem cells are non-embryonic stem cells. In some embodiments, the non-embryonic stem cells are adult stem cells. However, in certain embodiments, embryonic stem cells are optionally used as a source for exosomes. In some embodiments, somatic cells are used as a source for exosomes. In still additional embodiments, germ cells are used as a source for exosomes.

In several embodiments employing stem cells as an exosome source, the nucleic acid and/or protein content of exosomes from stem cells are particularly suited to effect the repair or regeneration of damaged or diseased cells. In several embodiments, exosomes are isolated from stem cells derived from the tissue to be treated. For example, in some embodiments where cardiac tissue is to be repaired, exosomes are derived from cardiac stem cells. Cardiac stem cells are obtained, in several embodiments, from various regions of the heart, including but not limited to the atria, septum, ventricles, auricola, and combinations thereof (e.g., a partial or whole heart may be used to obtain cardiac stem cells in some embodiments). In several embodiments, exosomes are derived from cells (or groups of cells) that comprise cardiac stem cells or can be manipulated in culture to give rise to cardiac stem cells (e.g., cardiospheres and/or cardiosphere derived cells (CDCs)). Further information regarding the isolation of cardiospheres can be found in U.S. Pat. No. 8,268,619, issued on Sep. 18, 2012, which is incorporated in its entirety by reference herein. In several embodiments, the cardiac stem cells are cardiosphere-derived cells (CDCs). Further information regarding methods for the isolation of CDCs can be found in U.S. patent application Ser. No. 11/666,685, filed on Apr. 21, 2008, and Ser. No. 13/412,051, filed on Mar. 5, 2012, both of which are incorporated in their entirety by reference herein. Other varieties of stem cells may also be used, depending on the embodiment, including but not limited to bone marrow stem cells, adipose tissue derived stem cells, mesenchymal stem cells, induced pluripotent stem cells, hematopoietic stem cells, and neuronal stem cells.

In several embodiments, administration of exosomes is particularly advantageous because there are reduced complications due to immune rejection by the recipient. Certain types of cellular or gene therapies are hampered by the possible immune response of a recipient of the therapy. As with organ transplants or tissue grafts, certain types of foreign cells (e.g., not from the recipient) are attacked and eliminated (or rendered partially or completely non-functional) by recipient immune function. One approach to overcome this is to co-administer immunosuppressive therapy, however this can be costly, and leads to a patient being subject to other infectious agents. Thus, exosomal therapy is particularly beneficial because the immune response is limited. In several embodiments, this allows the use of exosomes derived from allogeneic cell sources (though in several embodiments, autologous sources may be used). Moreover, the reduced potential for immune response allows exosomal therapy to be employed in a wider patient population, including those that are immune-compromised and those that have hyperactive immune systems. Moreover, in several embodiments, because the exosomes do not carry a full complement of genetic material, there is a reduced risk of unwanted cellular growth (e.g., teratoma formation) post-administration. Advantageously, the exosomes can be derived, depending on the embodiment, from cells obtained from a source that is allogeneic, autologous, xenogeneic, or syngeneic with respect to the eventual recipient of the exosomes. Moreover, master banks of exosomes that have been characterized for their expression of certain miRNAs and/or proteins can be generated and stored long-term for subsequent use in defined subjects on an "off-the-shelf" basis. However, in several embodiments, exosomes are isolated and then used without long-term or short-term storage (e.g., they are used as soon as practicable after their generation).

In several embodiments, exosomes need not be administered; rather the nucleic acid and/or protein carried by exosomes can be administered to a subject in need of tissue repair. In such embodiments, exosomes are harvested as described herein and subjected to methods to liberate and collect their protein and/or nucleic acid contents. For example, in several embodiments, exosomes are lysed with a detergent (or non-detergent) based solution in order to disrupt the exosomal membrane and allow for the collection of proteins from the exosome. As discussed above, specific methods can then be optionally employed to identify and selected particularly desired proteins. In several embodiments, nucleic acids are isolated using chaotropic disruption of the exosomes and subsequent isolation of nucleic acids. Other established methods for nucleic acid isolation may also be used in addition to, or in place of chaotropic disruption. Nucleic acids that are isolated may include, but are not limited to DNA, DNA fragments, and DNA plasmids, total RNA, mRNA, tRNA, snRNA, saRNA, miRNA, rRNA, regulating RNA, non-coding and coding RNA, and the like. In several embodiments in which RNA is isolated, the RNA can be used as a template in an RT-PCR-based (or other amplification) method to generate large copy numbers (in DNA form) of the RNA of interest. In such instances, should a particular RNA or fragment be of particular interest, the exosomal isolation and preparation of the RNA can optionally be supplemented by the in vitro synthesis and co-administration of that desired sequence.

In several embodiments, exosomes derived from cells are administered in combination with one or more additional agents. For example, in several embodiments, the exosomes are administered in combination with one or more proteins or nucleic acids derived from the exosome (e.g., to supplement the exosomal contents). In several embodiments, the cells from which the exosomes are isolated are administered in conjunction with the exosomes. In several embodiments, such an approach advantageously provides an acute and more prolonged duration of exosome delivery (e.g., acute based on the actual exosome delivery and prolonged based on the cellular delivery, the cells continuing to secrete exosomes post-delivery).

In several embodiments, exosomes are delivered in conjunction with a more traditional therapy, e.g., surgical therapy or pharmaceutical therapy. In several embodiments such combinations of approaches result in synergistic improvements in the viability and/or function of the target tissue. In some embodiments, exosomes may be delivered in conjunction with a gene therapy vector (or vectors), nucleic acids (e.g., those used as siRNA or to accomplish RNA interference), and/or combinations of exosomes derived from other cell types.

The compositions disclosed herein can be administered by one of many routes, depending on the embodiment. For example, exosome administration may be by local or systemic administration. Local administration, depending on the tissue to be treated, may in some embodiments be achieved by direct administration to a tissue (e.g., direct injection, such as intramyocardial injection). Local administration may also be achieved by, for example, lavage of a particular tissue (e.g., intra-intestinal or peritoneal lavage). In several embodiments, systemic administration is used and may be achieved by, for example, intravenous and/or intra-arterial delivery. In certain embodiments, intracoronary delivery is used. In several embodiments, the exosomes are specifically targeted to the damaged or diseased tissues. In some such embodiments, the exosomes are modified (e.g., genetically or otherwise) to direct them to a specific target site. For example, modification may, in some embodiments, comprise inducing expression of a specific cell-surface marker on the exosome, which results in specific interaction with a receptor on a desired target tissue. In one embodiment, the native contents of the exosome are removed and replaced with desired exogenous proteins or nucleic acids. In one embodiment, the native contents of exosomes are supplemented with desired exogenous proteins or nucleic acids. In some embodiments, however, targeting of the exosomes is not performed. In several embodiments, exosomes are modified to express specific nucleic acids or proteins, which can be used, among other things, for targeting, purification, tracking, etc. In several embodiments, however, modification of the exosomes is not performed. In some embodiments, the exosomes do not comprise chimeric molecules.

In some embodiments, subcutaneous or transcutaneous delivery methods are used. Due to the relatively small size, exosomes are particularly advantageous for certain types of therapy because they can pass through blood vessels down to the size of the microvasculature, thereby allowing for significant penetration into a tissue. In some embodiments, this allows for delivery of the exosomes directly to central portion of the damaged or diseased tissue (e.g., to the central portion of a tumor or an area of infarcted cardiac tissue). In addition, in several embodiments, use of exosomes is particularly advantageous because the exosomes can deliver their payload (e.g., the resident nucleic acids and/or proteins) across the blood brain barrier, which has historically presented an obstacle to many central nervous system therapies. In certain embodiments, however, exosomes may be delivered to the central nervous system by injection through the blood brain barrier. In several embodiments, exosomes are particularly beneficial for administration because they permit lower profile delivery devices for administration (e.g., smaller size catheters and/or needles). In several embodiments, the smaller size of exosomes enables their navigation through smaller and/or more convoluted portions of the vasculature, which in turn allows exosomes to be delivered to a greater portion of most target tissues.

The dose of exosomes administered, depending on the embodiment, ranges from about $1.0 \times 10^5$ to about $1.0 \times 10^9$ exosomes, including about $1.0 \times 10^5$ to about $1.0 \times 10^6$, about $1.0 \times 10^6$ to about $1.0 \times 10^7$, about $1.0 \times 10^7$ to about $5.0 \times 10^7$, about $5.0 \times 10^7$ to about $1.0 \times 10^8$, about $1.0 \times 10^8$ to about $2.0 \times 10^8$, about $2.0 \times 10^8$ to about $3.5 \times 10^8$, about $3.5 \times 10^8$ to about $5.0 \times 10^8$, about $5.0 \times 10^8$ to about $7.5 \times 10^8$, about $7.5 \times 10^8$ to about $1.0 \times 10^9$, and overlapping ranges thereof. In certain embodiments, the exosome dose is administered on a per kilogram basis, for example, about $1.0 \times 10^5$ exosomes/kg to about $1.0 \times 10^9$ exosomes/kg. In additional embodiments, exosomes are delivered in an amount based on the mass of the target tissue, for example about $1.0 \times 10^5$ exosomes/gram of target tissue to about $1.0 \times 109$ exosomes/gram of target tissue. In several embodiments, exosomes are administered based on a ratio of the number of exosomes the number of cells in a particular target tissue, for example exosome:target cell ratio ranging from about $10^9$:1 to about 1:1, including about $10^8$:1, about $10^7$:1, about $10^6$:1, about $10^5$:1, about $10^4$:1, about $10^3$:1, about $10^2$:1, about 10:1, and ratios in between these ratios. In additional embodiments, exosomes are administered in an amount about 10-fold to an amount of about 1,000,000-fold greater than the number of cells in the target tissue, including about 50-fold, about 100-fold, about 500-fold, about 1000-fold, about 10,000-fold, about 100,000-fold, about 500,000-fold, about 750,000-fold, and amounts in between these amounts. If the exosomes are to be administered in conjunction with the concurrent therapy (e.g., cells that can still shed exosomes, pharmaceutical therapy, nucleic acid therapy, and the like) the dose of exosomes administered can be adjusted accordingly (e.g., increased or decreased as needed to achieve the desired therapeutic effect).

In several embodiments, the exosomes are delivered in a single, bolus dose. In some embodiments, however, multiple doses of exosomes may be delivered. In certain embodiments, exosomes can be infused (or otherwise delivered) at a specified rate over time. In several embodiments, when exosomes are administered within a relatively short time frame after an adverse event (e.g., an injury or damaging event, or adverse physiological event such as an MI), their administration prevents the generation or progression of damage to a target tissue. For example, if exosomes are administered within about 20 to about 30 minutes, within about 30 to about 40 minutes, within about 40 to about 50 minutes, within about 50 to about 60 minutes post-adverse event, the damage or adverse impact on a tissue is reduced (as compared to tissues that were not treated at such early time points). In some embodiments, the administration is as soon as possible after an adverse event. In some embodiments the administration is as soon as practicable after an adverse event (e.g., once a subject has been stabilized in other respects). In several embodiments, administration is within about 1 to about 2 hours, within about 2 to about 3 hours, within about 3 to about 4 hours, within about 4 to about 5 hours, within about 5 to about 6 hours, within about 6 to about 8 hours, within about 8 to about 10 hours, within about 10 to about 12 hours, and overlapping ranges thereof. Administration at time points that occur longer after an adverse event are effective at preventing damage to tissue, in certain additional embodiments.

As discussed above, exosomes provide, at least in part, a portion of the indirect tissue regeneration effects seen as a result of certain cellular therapies. Thus, in some embodiments, delivery of exosomes (alone or in combination with an adjunct agent such as nucleic acid) provide certain effects (e.g., paracrine effects) that serve to promote repair of tissue, improvement in function, increased viability, or combinations thereof. In some embodiments, the protein content of delivered exosomes is responsible for at least a portion of the repair or regeneration of a target tissue. For example, proteins that are delivered by exosomes may function to replace damaged, truncated, mutated, or otherwise misfunctioning or nonfunctional proteins in the target tissue. In some embodiments, proteins delivered by exosomes, initiate a signaling cascade that results in tissue repair or regeneration. In several embodiments, miRNA delivery by exosomes is responsible, in whole or in part, for repair and/or regeneration of damaged tissue. As discussed above, miRNA delivery may operate to repress translation of certain messenger RNA (for example, those involved in programmed cell death), or may result in messenger RNA cleavage. In either case, and in some embodiments, in combination, these effects alter the cell signaling pathways in the target tissue and, as demonstrated by the data disclosed herein, can result in improved cell viability, increased cellular replication, beneficial anatomical effects, and/or improved cellular function, each of which in turn contributes to repair, regeneration, and/or functional improvement of a damaged or diseased tissue as a whole.

Causes of Damage or Disease

The methods and compositions disclosed herein can be used to repair or regenerate cells or tissues affected by a wide variety of types of damage or disease. The compositions and methods disclosed herein can be used to treat inherited diseases, cellular or body dysfunctions, combat normal or abnormal cellular ageing, induce tolerance, modulate immune function. Additionally, cells or tissues may be damaged by trauma, such as blunt impact, laceration, loss of blood flow and the like. Cells or tissues may also be damaged by secondary effects such as post-injury inflammation, infection, auto-digestion (for example, by proteases liberated as a result of an injury or trauma). The methods and compositions disclosed herein can also be used, in certain embodiments, to treat acute events, including but not limited to, myocardial infarction, spinal cord injury, stroke, and traumatic brain injury. In several embodiments, the methods and compositions disclosed herein can be used to treat chronic diseases, including but not limited to neurological impairments or neurodegenerative disorders (e.g., multiple sclerosis, amyotrophic lateral sclerosis, heat stroke, epilepsy, Alzheimer's disease, Parkinson's disease, Huntington's disease, dopaminergic impairment, dementia resulting from other causes such as AIDS, cerebral ischemia including focal cerebral ischemia, physical trauma such as crush or compression injury in the CNS, including a crush or compression injury of the brain, spinal cord, nerves or retina, and any other acute injury or insult producing neurodegeneration), immune deficiencies, facilitation of repopulation of bone marrow (e.g., after bone marrow ablation or transplantation), arthritis, auto-immune disorders, inflammatory bowel disease, cancer, diabetes, muscle weakness (e.g., muscular dystrophy, amyotrophic lateral sclerosis, and the like), progressive blindness (e.g. macular degeneration), and progressive hearing loss.

In several embodiments, exosomes can be administered to treat a variety of cancerous target tissues, including but not limited to those affected with one or of acute lymphoblastic leukemia (ALL), acute myeloid leukemia (AML), adrenocortical carcinoma, kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, craniopharyngioma, ependymoblastoma, ependymoma, medulloblastoma, medulloepithelioma, breast cancer, bronchial tumors, burkitt lymphoma, cervical cancer, colon cancer, chronic lymphocytic leukemia (CLL), chronic myelogenous leukemia (CML), chronic myeloproliferative disorders, ductal carcinoma, endometrial cancer, esophageal cancer, gastric cancer, Hodgkin lymphoma, non-Hodgkin lymphoma hairy cell leukemia, renal cell cancer, leukemia, oral cancer, liver cancer, lung cancer, lymphoma, melanoma, ocular cancer, ovarian cancer, pancreatic cancer, prostate cancer, pituitary cancer, uterine cancer, and vaginal cancer.

Alternatively, in several embodiments, exosomes are delivered to an infected target tissue, such as a target tissue infected with one or more bacteria, viruses, fungi, and/or parasites. In some embodiments, exosomes are used to treat tissues with infections of bacterial origin (e.g., infectious bacteria is selected the group of genera consisting of *Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia,* and mutants or combinations thereof). In several embodiments, the exosomes inhibit or prevent one or more bacterial functions, thereby reducing the severity and/or duration of an infection. In several embodiments, administration of exosomes sensitizes the bacteria (or other pathogen) to an adjunct therapy (e.g., an antibiotic).

In some embodiments, the infection is viral in origin and the result of one or more viruses selected from the group consisting of adenovirus, Coxsackievirus, Epstein-Barr virus, hepatitis a virus, hepatitis b virus, hepatitis c virus, herpes simplex virus type 1, herpes simplex virus type 2, cytomegalovirus, ebola virus, human herpes virus type 8, HIV, influenza virus, measles virus, mumps virus, human papillomavirus, parainfluenza virus, poliovirus, rabies virus, respiratory syncytial virus, rubella virus, and varicella-zoster virus. Exosomes can be used to treat a wide variety of cell types as well, including but not limited to vascular cells, epithelial cells, interstitial cells, musculature (skeletal, smooth, and/or cardiac), skeletal cells (e.g., bone, cartilage, and connective tissue), nervous cells (e.g., neurons, glial cells, astrocytes, Schwann cells), liver cells, kidney cells, gut cells, lung cells, skin cells or any other cell in the body.

Therapeutic Compositions

In several embodiments, there are provided compositions comprising exosomes for use in repair or regeneration of tissues that have been adversely impacted by damage or disease. In several embodiments, the compositions comprise, consist of, or consist essentially of exosomes. In some embodiments, the exosomes comprise nucleic acids, proteins, or combinations thereof. In several embodiments, the nucleic acids within the exosomes comprise one or more types of RNA (though certain embodiments involved exosomes comprising DNA). The RNA, in several embodiments, comprises one or more of messenger RNA, snRNA, saRNA, miRNA, and combinations thereof. In several embodiments, the miRNA comprises one or more of miR-26a, miR27-a, let-7e, mir-19b, miR-125b, mir-27b, let-7a, miR-19a, let-7c, miR-140-3p, miR-125a-5p, miR-150, miR-155, mir-210, let-7b, miR-24, miR-423-5p, miR-22, let-7f, miR-146a, and combinations thereof. In several embodiments, the compositions comprise, consist of, or consist essentially of a synthetic microRNA and a pharmaceutically acceptable carrier. In some such embodiments, the synthetic microRNA comprises miR146a. In several embodiments the miRNA is pre-miRNA (e.g., not mature), while in some embodiments, the miRNA is mature, and in still additional embodiments, combinations of pre-miRNA and mature miRNA are used.

In several embodiments, the compositions comprise exosomes derived from a population of cells, as well as one or more cells from the population (e.g., a combination of exosomes and their "parent cells"). In several embodiments, the compositions comprise a plurality of exosomes derived from a variety of cell types (e.g., a population of exosomes derived from a first and a second type of "parent cell"). As discussed above, in several embodiments, the compositions disclosed herein may be used alone, or in conjunction with one or more adjunct therapeutic modalities (e.g., pharmaceutical, cell therapy, gene therapy, protein therapy, surgery, etc.).

EXAMPLES

Examples provided below are intended to be non-limiting embodiments of the invention.

Example 1—Isolation and Characterization of Exosomes

Prior studies in the area of cardiac tissue repair and regeneration have demonstrated that the repair and/or regeneration of cardiac tissue is a result of both direct and indirect factors. For example, it has been shown that CDCs account for approximately 10% of regenerated cardiac tissue. Such studies suggest that alternative mechanisms, such as indirect effects, are at play. As discussed above, exosomes and their nucleic acid content may be involved, at least in part, in providing cellular or tissue repair and/or regeneration via indirect mechanisms. The present example was designed to characterize exosomes and their nucleic acid content.

Figure 2A:
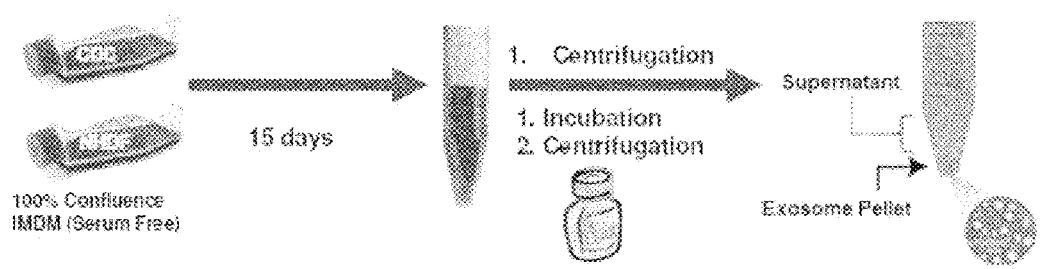
FIGS. 2A-2D depict information related to the isolation of exosomes and characterization of cells during the isolation protocol.
Figure 2B:
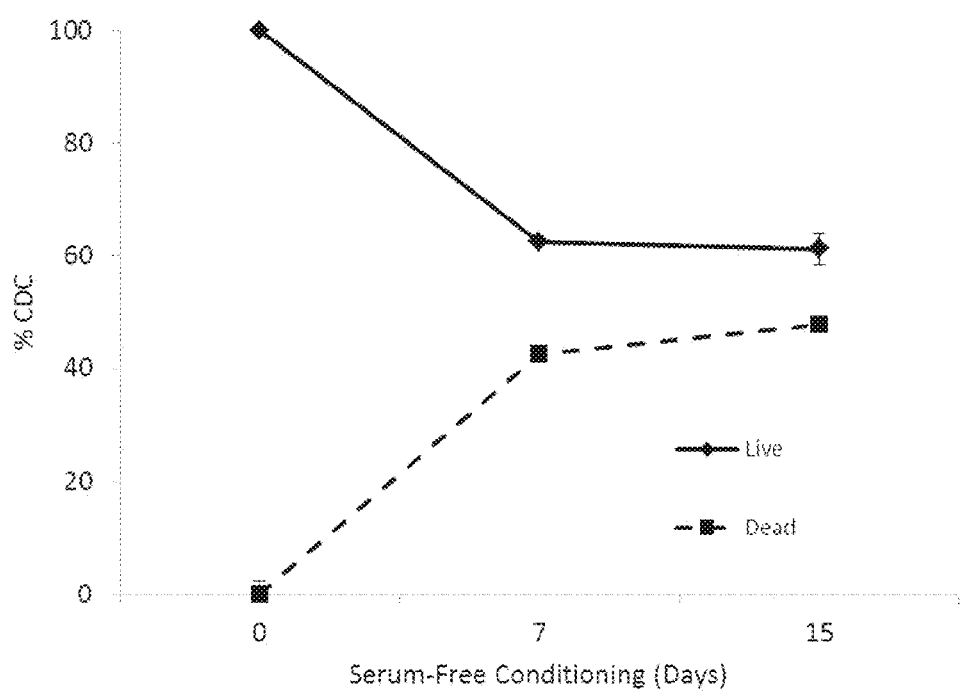
Figure 2C:
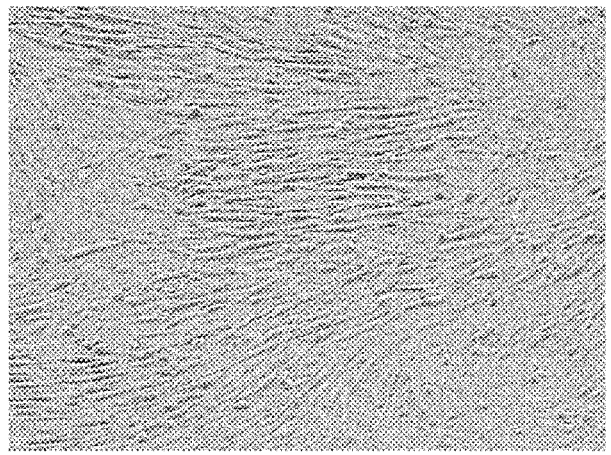
Figure 2D:
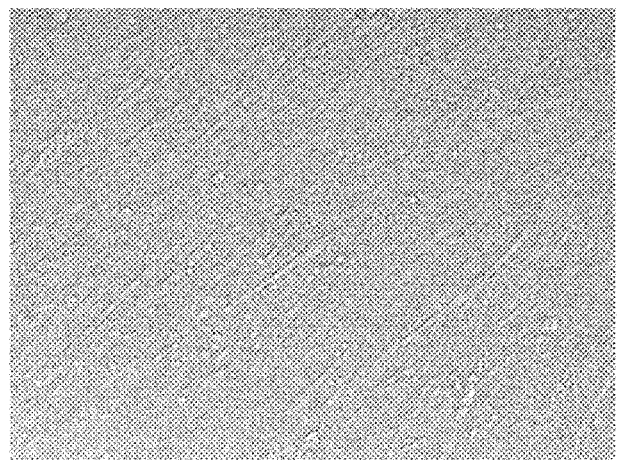
Figure 3A:
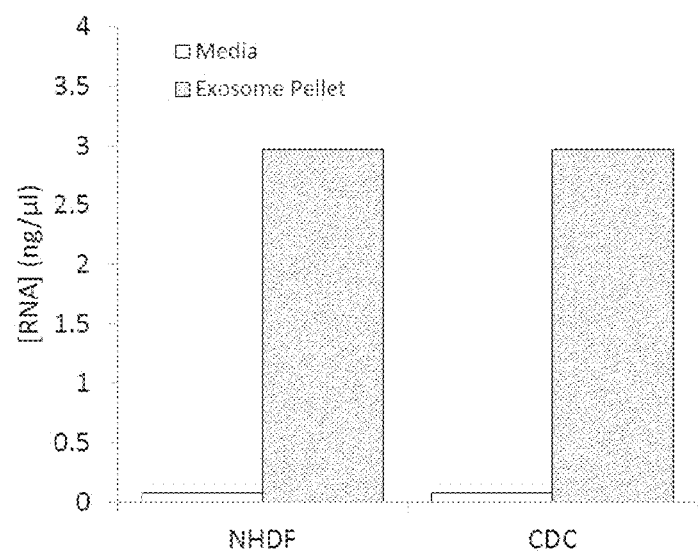
FIGS. 3A-3E depict exosome characterization data.
Figure 3B:
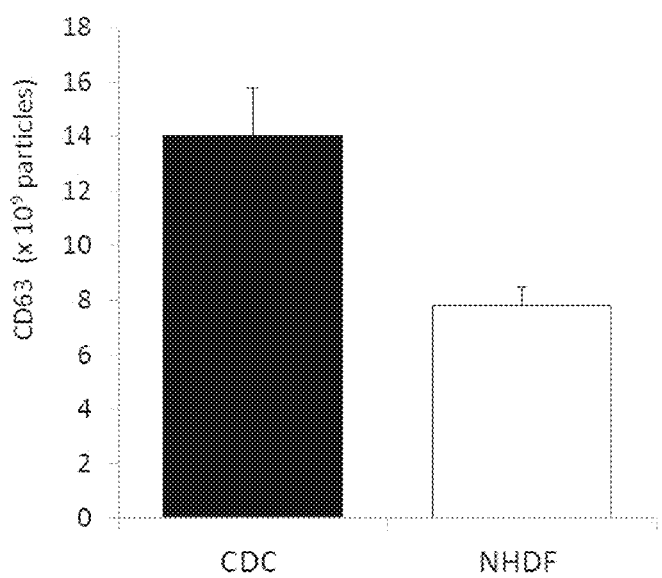
Figure 3C:
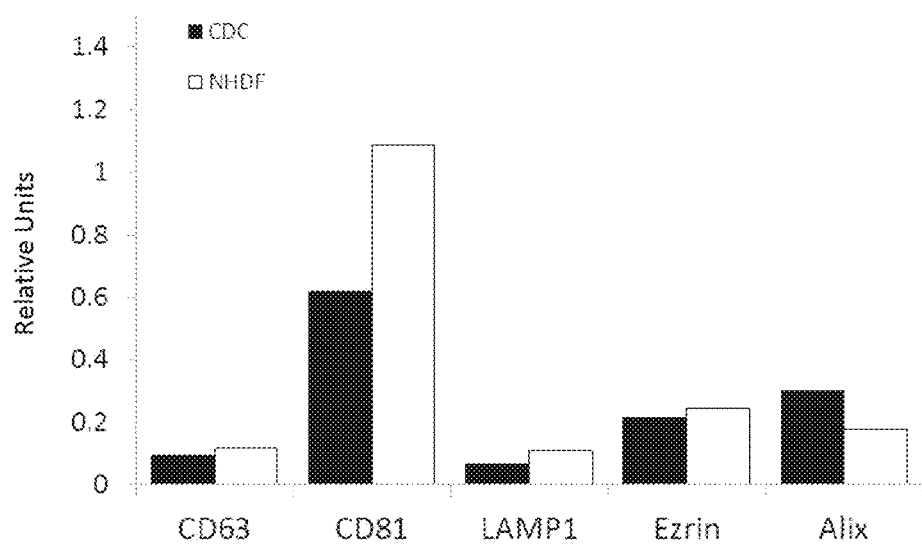
Figure 3D:
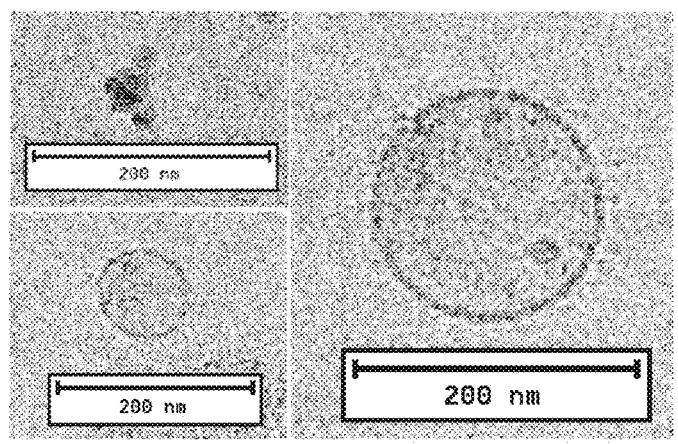
Figure 3E:
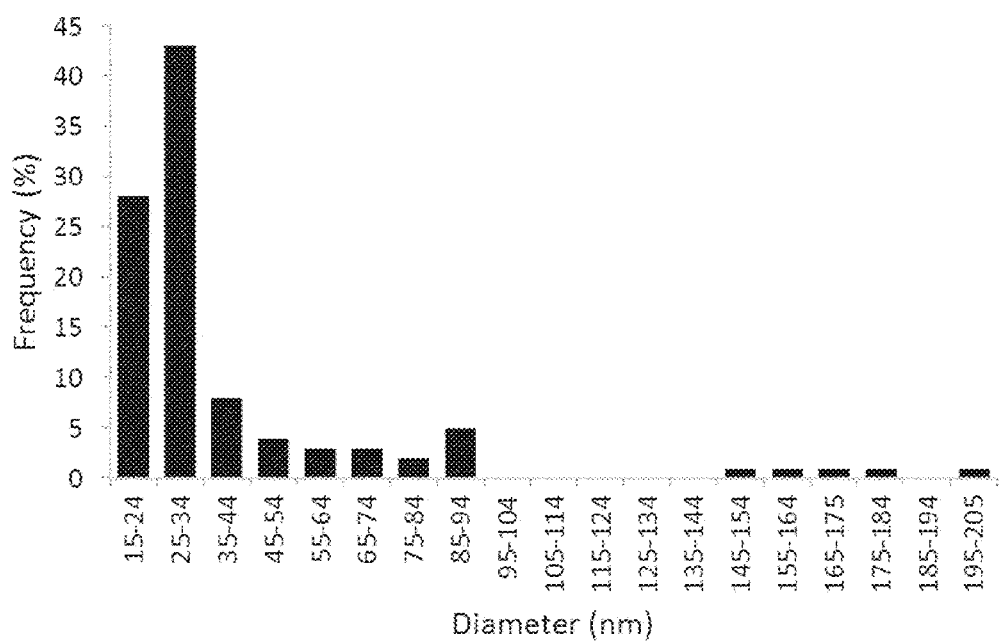

In order to isolate exosomes, cultured cells were grown to 100% confluence in serum free media. For this experiment, exosome yield and RNA content was compared between cultured CDCs and normal human dermal fibroblast (NHDF) cells. It shall be appreciated that, in several embodiments, exosomes may be isolated from other cell types, and may be harvested at time points were confluence is less than 100%. After about 15 days in culture, the cells were displaced from the culture vessel and centrifuged to remove cellular debris. After incubation in EXOQUICK exosome precipitation solution (System Biosciences, Mountain View, Calif., USA), the cells were centrifuged (1500×g for 30 min; though in some embodiments, other conditions are used) to yield an exosome pellet fraction and a supernatant fraction. In some embodiments, the incubation in exosome precipitation solution enhances isolation of exosomes (or the contents thereof) without the need for ultracentrifugation. However, m some embodiments, ultracentrifugation is optionally used. In some embodiments, other reagents and/or incubation conditions may be used, depending on the downstream use of the exosomes (or their contents) following exosome isolation. For example, in several embodiments, PBS incubations are used when exosomes are to be studied by electron microscopy or flow cytometry. Cell growth medium (exosome depleted in some embodiments) is used in certain embodiments wherein functional studies are to be performed. Lysis buffer is used in certain embodiments, wherein protein and/or RNA is to be isolated from the exosomes. A schematic of the isolation process is shown in FIG. 2A. The RNA concentration was determined for both cell types, and both isolated fractions. As shown in FIG. 3A, the exosome pellet fraction for both CDCs and NHDF cells contain the vast majority of RNA The amount of proteinaceous material isolated from CDCs, as compared to NHDF cells, was compared by evaluating CD63 (a marker of transmembrane proteins) content of the exosome pellet fraction. Data are shown in FIG. 3B. FIG. 3C shows additional gene expression data comparing CDCs and NHDF. CD81 encodes a protein that is a member of the transmembrane 4 superfamily (also known as the tetraspanin family). This family of proteins mediate a variety of signal transduction events involved in, for example, regulation of cell development, activation, growth and motility. These proteins also complex with integrins and thus may play a role in cell attachment and fusion. LAMP 1 (also known as CD107a) encodes a protein that is a membrane glycoprotein that is related to activation of immune cells. Ezrin (or cytovillin) encodes a peripheral membrane protein that functions as a tyrosine-kinase substrate and serves as a functional linker between the membrane of cells and the actin cytoskeleton. As such, this protein has important function in maintenance of cell adhesion, cell migration and cellular organization. ALIX (Apoptosis-Linked gene 2 Interacting protein X) encodes a cytoplasmic protein, but it has previously been established as being concentrated in Exosomes and phagosomes. Thus, it serves as an additional marker of exosomes that can be used to characterization preparations from various cells. FIG. 3D depicts scanning electron microscopic images of at various magnifications. FIG. 3E shows a histogram of exosome diameter versus frequency. Exosomes range in diameter from between about 15 nm to about 205 nm, with the majority of the exosomes in the range of about 15 nm to about 95 nm in diameter.

These data indicate that CDCs are a rich source of both mRNA and protein, which may play a role in the indirect regenerative effects realized after CDC administration.

Example 2—Exosomes Promote Survival and Proliferation of Other Cells

Figure 4:
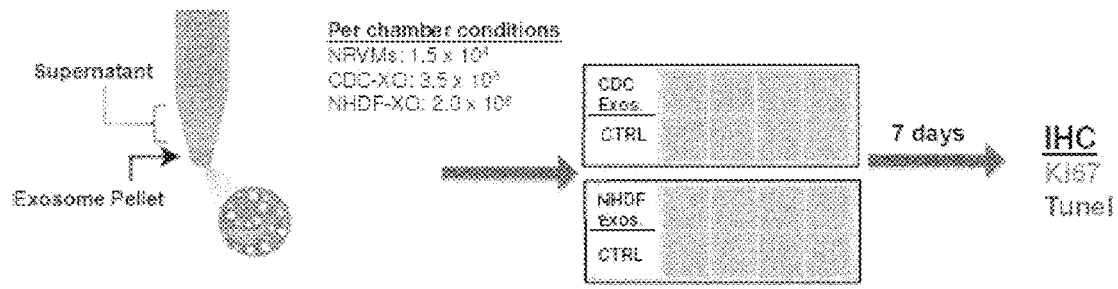
FIG. 4 depicts a schematic protocol for the evaluation of the effects of exosome treatment on cellular proliferation and cell death.
Figures 5A, 5B:
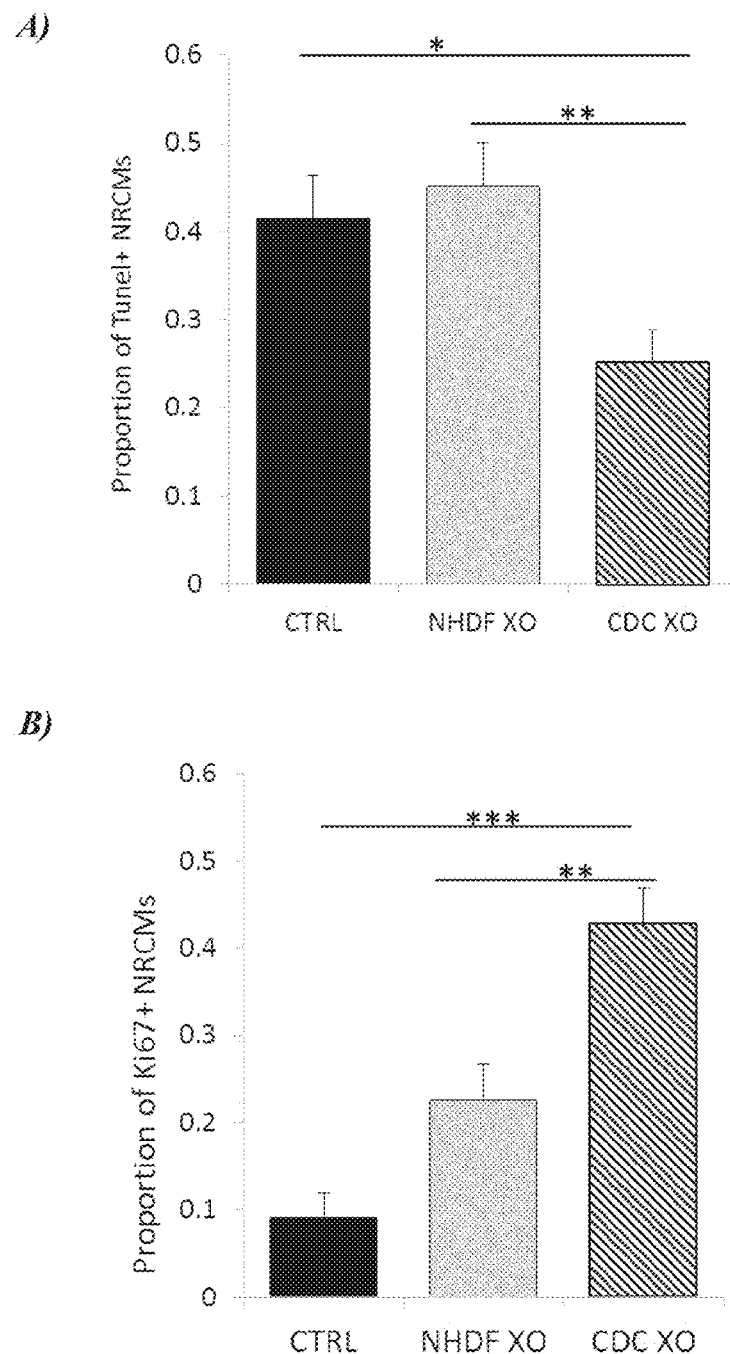
FIGS. 5A-5D depict data related to the effects of exosome treatment on cell death and cellular proliferation.
Figure 5C:
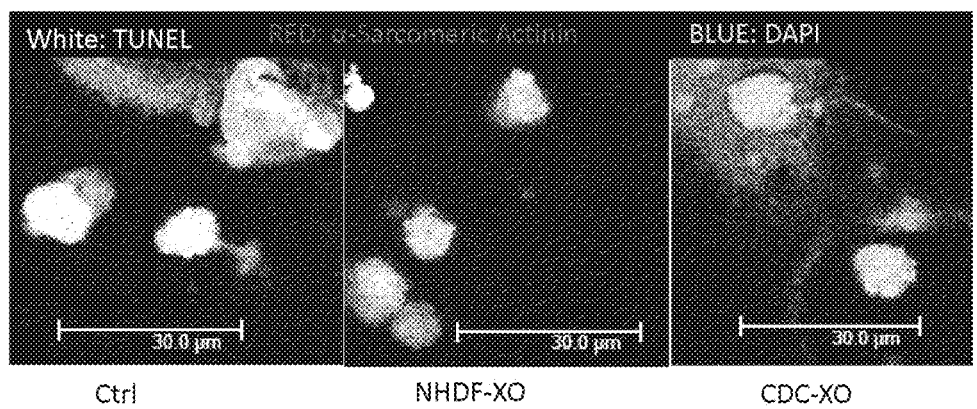
Figure 5D:
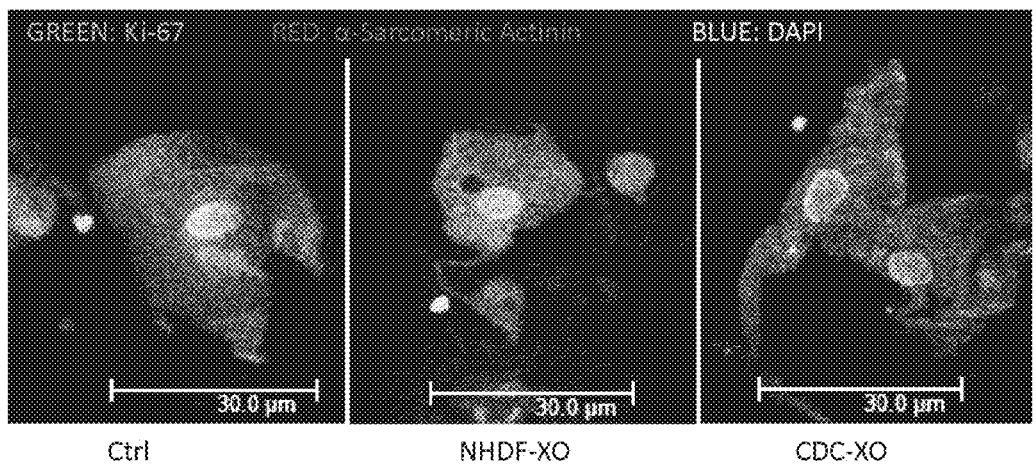

In vitro experiments were undertaken to evaluate the pro-regenerative and anti-apoptotic effects of exosomes on other cell types. Exosomes were isolated from CDCs or NHDF cells as discussed above. A portion of the exosome pellet fraction was then co-incubated with cultured neonatal rat ventricular myocytes (NRVM) in chamber slides for approximately 7 days. At the end of seven days, the co-cultures were evaluated by immunohistochemistry for changes in indices of proliferation or cell death (as measured by markers of apoptosis). A schematic for this protocol is shown in FIG. 4. FIG. 5A shows data related to death of the NRVM cells, as measured by TUNEL staining. Incubation of NRVM cells with exosomes isolated from CDCs resulted in a significantly lower degree of apoptosis, as compared to both control cells and cells incubated with exosomes from NHDF cells (CDC: 25.2±0.04%; NHDF: 45.1±0.05%, p<0.01); Control: 41.4±0.05%, n=4, p<0.05). FIG. 5B indicates that incubation of NRVM cells with exosomes isolated from CDCs resulted in a significantly more cellular proliferative activity (as measured by Ki67), as compared to both control cells and cells incubated with exosomes from NHDF cells (CDC: 42.7±0.04%; NHDF 22.5±0.04%; control: 9.1%±0.03%, n=4, p<0.001). FIG. 5C shows confocal fluorescent microscopic analysis of TUNEL staining in NRCM incubated without exosomes, with exosomes from NHDF cells, or with exosomes from CDCs. As in FIG. 5A, incubation of NRCM with exosomes reduced apoptosis (less TUNEL-positive staining), with CDC-derived exosomes providing a more significant reduction than those from NHDF. FIG. 5D shows confocal fluorescent microscopic analysis of Ki67 staining. Again, recapitulating the data shown in FIG. 5B, CDC-derived exosomes result in an increased proliferative activity of NRCMs. Taken together, these data suggest, that in comparison to other cell types, CDCs provide exosomes that may be particularly beneficial in the context of tissue repair and/or regeneration, based on their ability to reduce cell death and increase proliferative activity. These effects, in several embodiments, if realized in an acutely damaged cell or tissue, or even a chronically damaged or diseased cell or tissue, aid in the repair or regeneration of the damaged cells or tissue.

Example 3—Exosomes Promote Angiogenesis

Figure 6:
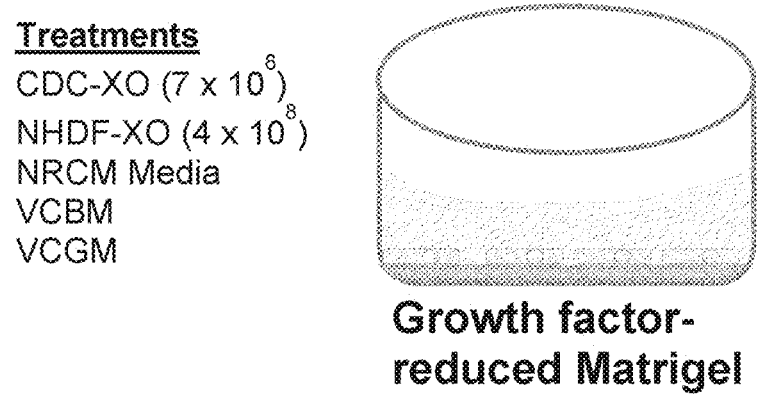
FIG. 6 depicts a schematic protocol for the evaluation of the effects of exosome treatment on angiogenesis.
Figure 7:
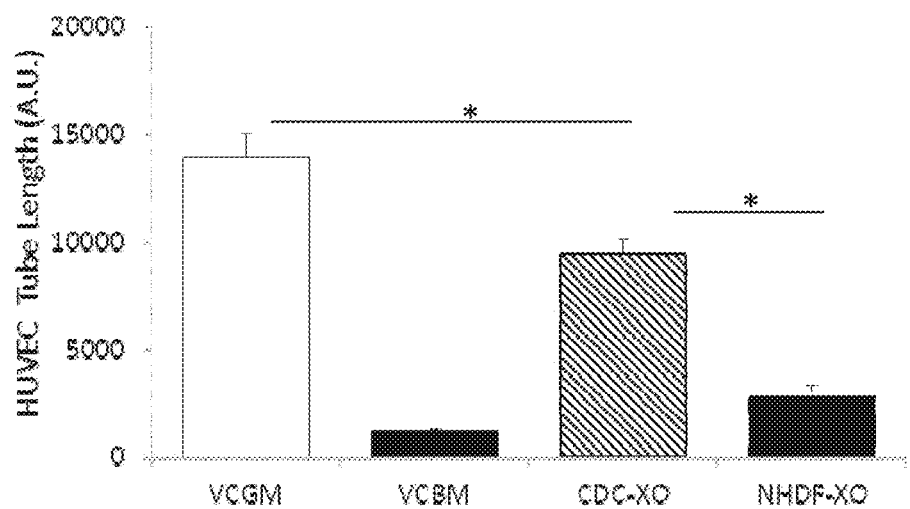
FIG. 7 depicts summary data related to angiogenesis after treatment of endothelial cells with various media and exosome preparations.

In addition to increased proliferation and/or reduced death of cells or tissue in a region of damage or disease, reestablishment or maintenance of blood flow may play a pivotal role in the repair or regeneration of cells or tissue. As such, the ability of exosomes to promote angiogenesis was evaluated. Human umbilical vein endothelial cells (HUVEC) were subjected to various co-incubation conditions. These conditions are depicted in FIG. 6. Briefly, HUVEC cells were grown in culture dishes on growth factor reduced MATRIGEL. The cells were grown in either neonatal rat cardiomyocyte media (NRCM), MRCM supplemented with CDC-derived exosomes, MRCM supplemented with NHDF-derived exosomes, vascular cell basal media (VCBM), or vascular cell growth media (VCGM). As shown in FIG. 7, VCGM induced robust tube formation as compared to VCBM (CDC: 9393±689; NHDF: 2813±494.5, control, 1097±116.1, n=3, p<0.05). Media from NRCM resulted in tube formation similar to VCBM (data not shown). As shown, media supplemented with exosomes derived from CDCs also induced a significant tube formation, while media supplemented with exosomes derived from NHDF showed less tube formation. Representative photomicrographs of tube formation resulting from the various treatment conditions are shown in FIG. 8A-8E. These data demonstrate that, in addition to the positive effects on cellular proliferation and the reduction in cell death that exosomes derived from certain cell types have the ability to promote tube formation, which is representative of the capacity to generate new vasculature in vivo. Thus, in several embodiments, administration of exosomes (or the contents of exosomes, e.g. mRNA or proteins) to a region of damage or diseased tissue results in increased angiogenesis. This in turn, has the capacity to improve the viability and/or the function of the cells and tissue in the target region.

Example 4—Effects of Exosomes In Vivo

Figure 9:
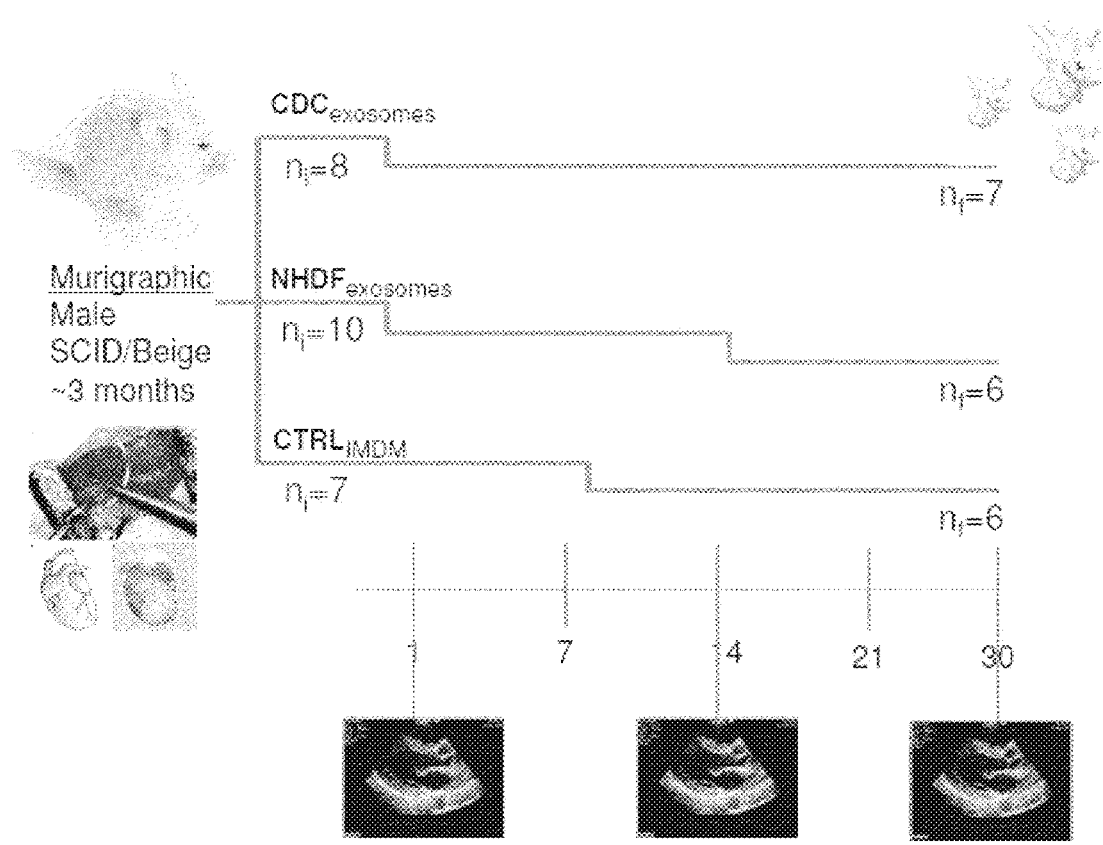
FIG. 9 depicts data related to the survival of mice subject to myocardial infarction and treated with various exosome preparations.
Figure 10:
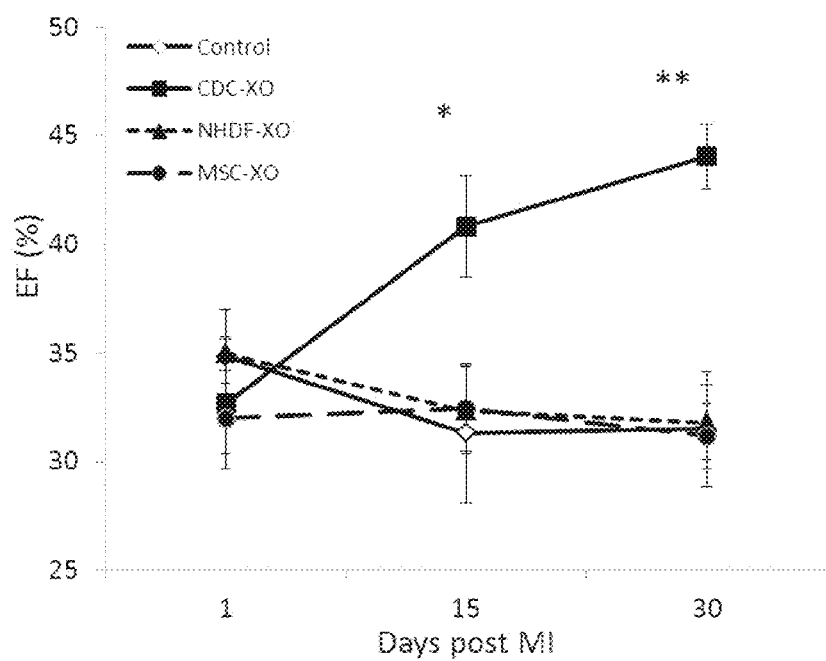
FIG. 10 depicts cardiac functional data after myocardial infarction and treatment with exosome preparations.

In view of the in vitro experimental results described above, in vivo experiments were performed to determine the effects of exosomes administration on cardiac tissue regeneration after myocardial infarction. Acute myocardial infarction (MI) was created in SCID/Beige mice of approximately 3 months of age by ligation of the mid-left anterior descending coronary artery and exosome preparations or vehicle was injected under direct visualization at two peri-infarct sites. As disclosed herein, other delivery routes (e.g., intracoronary, intramyocardially, IV, etc.) are used in some embodiments. Animals received either control solution (Iscove's Modified Dulbecco's Medium; IMDM), exosomes isolated from mesenchymal stem cells (MSC-XO), exosomes isolated from NHDF (NHDF-XO), or exosomes isolated from CDCs (CDC-XO). After injection, the survival rate of each of the experimental groups was tracked over time. In addition, MM images were collected at one day post infarct, 14 days post infarct, and 30 days post infarct, to characterize the dimensions of the cardiac tissue. FIG. 9 summarizes the results of the survival experiment. Notably, seven of eight CDC exosome-injected mice survived for 30 days. In contrast, only six of ten NHDF exosome-injected mice survived for 30 days. Six of seven control mice survived for 30 days. MSC-XO data not shown. In addition to improved overall survival, administration of exosomes isolated from CDCs resulted in improved function. These data are depicted in FIG. 10, which shows left ventricular ejection fraction (LVEF) that was improved significantly at both two weeks and four weeks post-myocardial infarction in the group treated with exosomes derived from CDCs. The improvement in LVEF as a result of treatment with exosomes derived from CDCs is surprising in view of the decline in cardiac function seen in the NHDF exosome group (which was no different than control or cells treated with MSC-XO). At two weeks, LVEF in the CDC exosome group was 40.8±2.33% (compared to 32.34±2.0% in the NHDF group, 32.41±1.9% in the MSC-XO group, and 31.31±3.2% in the control group; any n=6, $p<0.05$). At four weeks, LVEF in the CDC exosome group was 44.03±1.5% (compared to 31.8±1.7% in the NHDF group, 31.17±1.5% in the MSC-XO group, and 31.5±2.7% in the control group; any n=6, $p<0.05$).

Figure 11A:
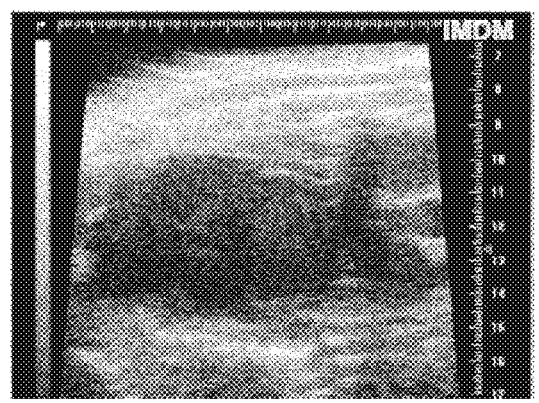
FIGS. 11A-11C depicts echocardiography (ECHO) data after myocardial infarction and treatment with exosome preparations.
Figure 11B:
Figure 11C:

In addition to these functional improvements, administration of exosomes derived from CDCs resulted in an increase in the amount of regenerated cardiac tissue (see e.g., FIG. 11C as compared to FIGS. 11A-11B). Echo data for MSC-XO not shown. Additional data relating to anatomical improvements (e.g. regenerated myocardium) is shown in FIG. 12. FIGS. 12A-12D depict representative Masson's trichrome stained sections of cardiac tissue from each of the various treatment groups. Comparing FIG. 12D to FIG. 12A, demonstrates that exosomes derived from CDC's increase the wall thickness and reduce the chamber volume, which translates to improved cardiac function. Exosomes derived from NHDF (12B) also increased wall thickness as compared to control, but not to the same extent as exosomes from CDCs. In contrast, exosomes from MSCs failed to regenerate myocardium to the same degree as either NHDF or CDCs.

Figure 12E:
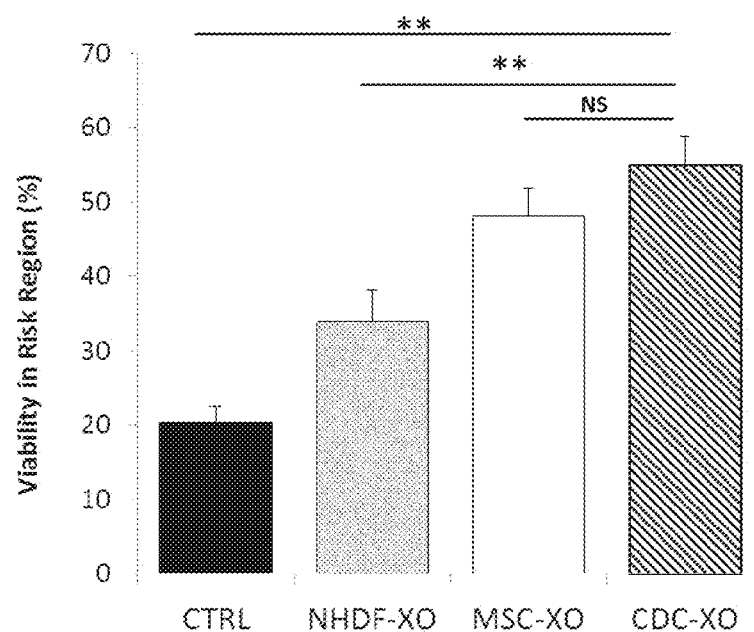

FIG. 12E depicts data relating to the percent viability of tissue in the risk region (the area around the infarct site). Exosomes derived from CDCs significantly improved cell viability as compared to control ($p<0.01$) as well as compared to NHDF exosomes ($p<0.01$). The viability in the risk region was not significantly different when compared to MSC-XO treated mice.

Figure 12F:
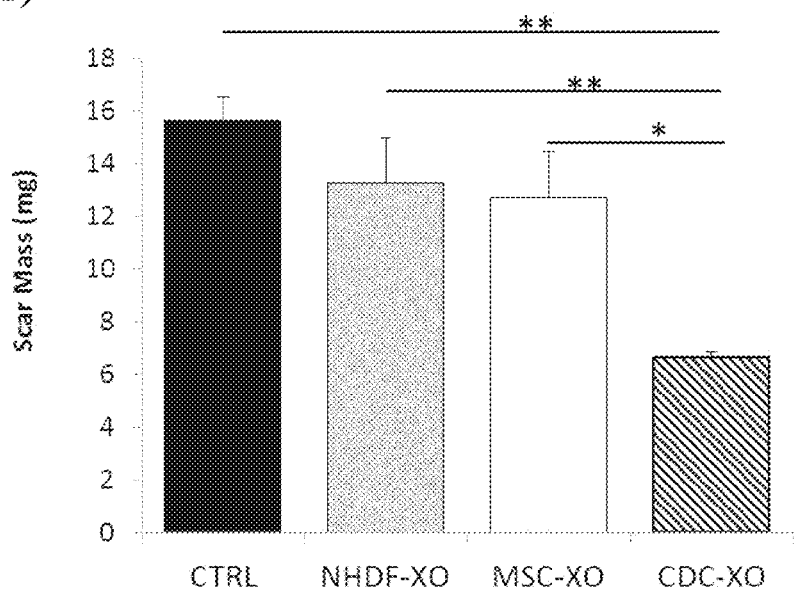
Figure 12G:
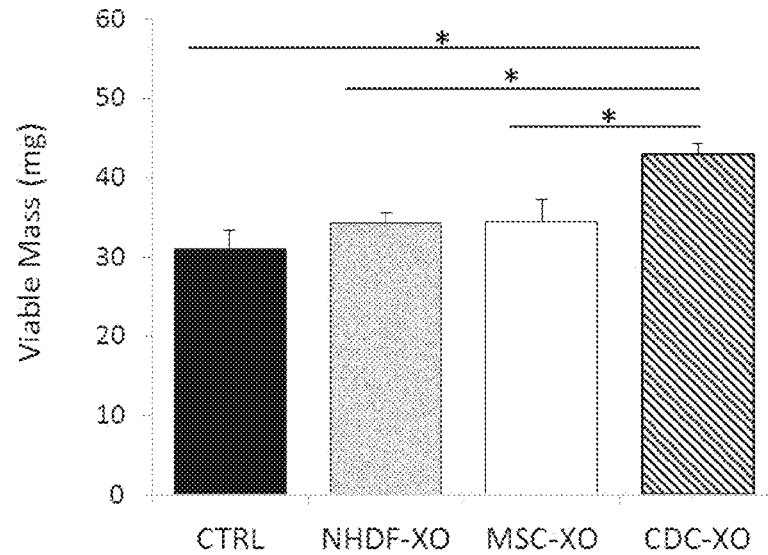
Figure 12H:
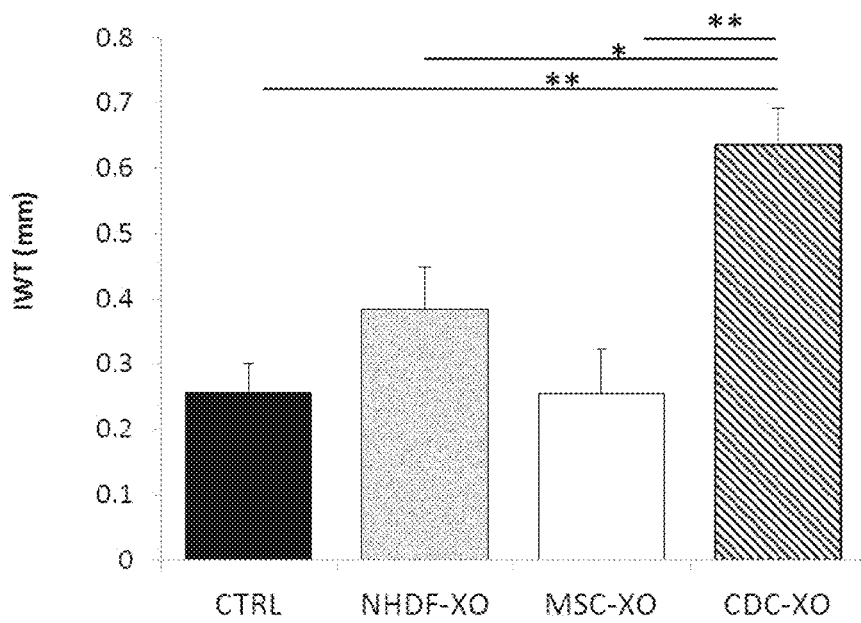

Further indications of anatomical improvements are shown in FIGS. 12F-12H. FIG. 12F shows the absolute amounts of scar mass resulting from the induced myocardial infarction. NHDF exosomes did not significantly reduce scar mass as compared to control, however, exosomes derived from CDCs significantly reduced the scar mass, not only compared to control, but as compared to all other treatment groups ($p<0.05$ v. MSC-XO, $p<0.01$ v. control and NHDF-XO). Not only does this represent an anatomical improvement, because scar tissue has reduced contractility, but the reduction in scar tissue is often associated with improved functionality. FIG. 12G indicates that exosomes derived from CDCs yield a significant increase in the overall viable mass of cardiac tissue as compared to control or any other treatment group ($p<0.05$). Finally, FIG. 12H indicates that exosomes derived from CDCs result in a significant increase in cardiac wall thickness in the infarct region (as compared to both control and MSC exosomes, $p<0.01$, and compared to NHDF exosomes, $p<0.05$). Again, this increased thickness, in several embodiments, contributes, at least in part, to increased cardiac function.

These data indicate that, in several embodiments, functional improvements result from the administration of exosomes. In several embodiments, anatomical improvements result. In still additional embodiments, both functional and anatomical improvements are realized. Moreover, administration of exosomes, in several embodiments, results in an increase in the viability of cells or tissue in the region of damage or disease. In some embodiments, exosomes themselves need not be administered, but rather the contents or a portion of the contents of the exosomes can be administered (e.g., nucleic acids, proteins, or combinations thereof) to result in functional and/or anatomical improvements.

Figure 13:
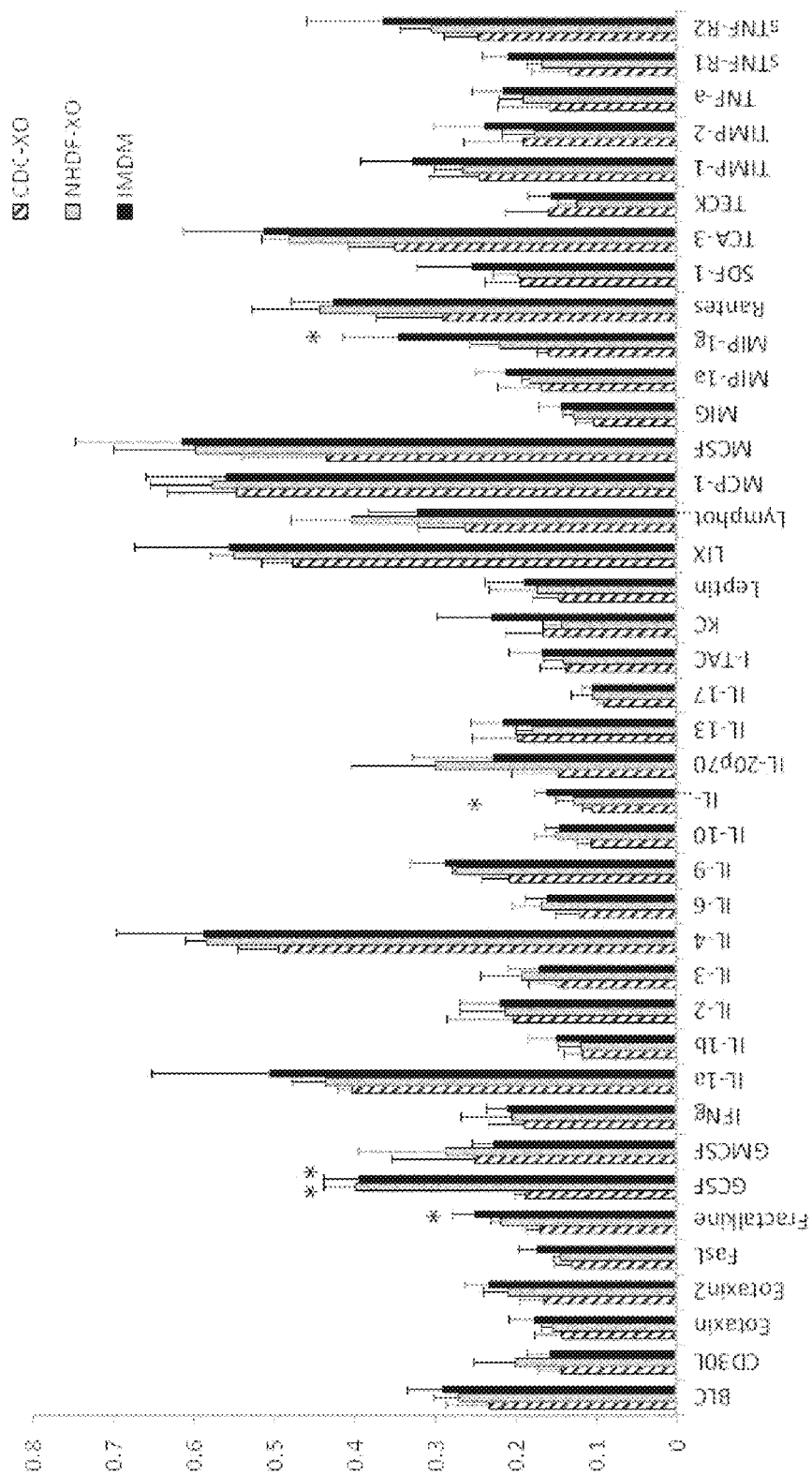
FIG. 13 depicts data related to the reduced myocardial levels of inflammatory markers after treatment with exosomes derived from cardiosphere-derived cells (CDCs).

In addition to these anatomical and functional improvements, in several embodiments, administration of exosomes to a damaged or diseased tissue can ameliorate one or more secondary effects of the damage or disease, such secondary effects, often leading to potentiation of injury or loss of function in the damaged tissue. In several embodiments, inflammation is one such secondary effect. The infiltration of inflammatory cells into a tissue that has been damaged or is subject to disease, can oftentimes induce additional damage and or, loss of function. For example, inflammatory cells may initiate certain pathways, which result in the further destruction of cells, including those that are not directly injured or diseased. In order to evaluate the effect of exosome delivery on secondary effects, the expression level of a panel of inflammatory markers was evaluated one month post myocardial infarction. These data are shown in FIG. 13. As depicted, exosomes derived from CDCs (the left bar in each group), are associated with lower levels of inflammatory associated markers. Depending on the marker, exosomes derived from CDCs display significantly reduced expression of the inflammatory marker (see e.g., expression for fractalkine, GCSF, IL12p40p70, MIP-1g). In several embodiments, the methods disclosed herein result in a decrease in the expression of (or inflammatory activity associated with) one or more of BLC, CD30L, eotaxin, eotaxin 2, FasL, fractalkine, GCSF, GM-CSF, interferon gamma, IL-1a, IL-1b, IL-2, IL-3, IL-4, IL-6, IL-9, IL-10, IL-12p40p70, IL-20p70, IL-13, IL-17, I-TAC, KC, leptin, LIX, lymphotactin, MCP-1, MCSF, MIG, MIP-1a, MIP-1g, RANTES, SDF-1, TCA-3, TECK, TIMP-2, tumor necrosis factor alpha, sTNF-R1, and sTNF-R2. In some embodiments, administration of exosomes results in a reduction in inflammatory markers at time points earlier than 30 days.

For example, in some embodiments, immediate reduction in inflammatory markers post injury results in less subsequent damage to the tissue due to inflammation. Thus, in some embodiments, inflammatory markers are reduced by exosomes administration on a timeframe ranging from about 2 to about 5 hours, about five to about seven hours, about seven to about 10 hours, about 10 to about 15 hours, about 15 to about 20 hours, about 20 to about 24 hours, and overlapping ranges thereof. In still additional embodiments, exosomes administration results in a reduction of inflammatory markers on a timeframe from about one day to about three days, about three days to about five days, about five days to about 10 days, about 10 days to about 15 days, about 15 days to about 20 days, about 20 days to about 30 days, and overlapping ranges thereof. Additionally, in several embodiments, administration of exosomes reduces the expression and/or infiltration of inflammatory mediators for longer periods of time.

Example 5—Mechanisms of Exosome Secretion

Not only is the understanding that exosomes are capable of facilitating repair and/or regeneration of diseased or damaged tissues important, it is also important to understand processes for the efficient collection of exosomes. Understanding the mechanisms involved in exosomes secretion, and several embodiments, allow for optimization of the efficiency of exosome isolation.

Figure 14A:
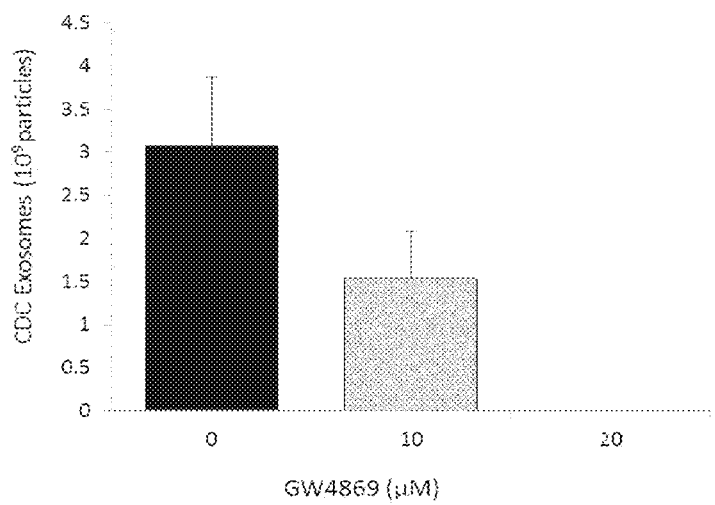
FIGS. 14A-14C depicts data related to mechanisms of exosome secretion.
Figure 14B:
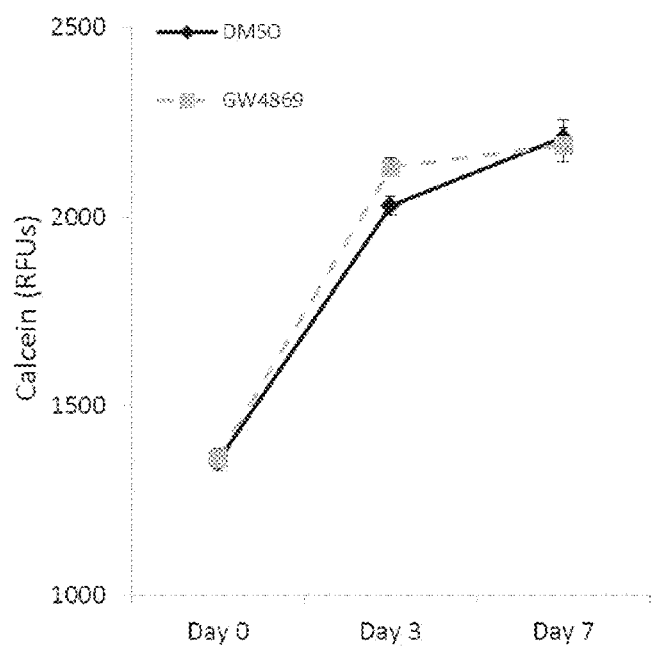
Figure 14C:
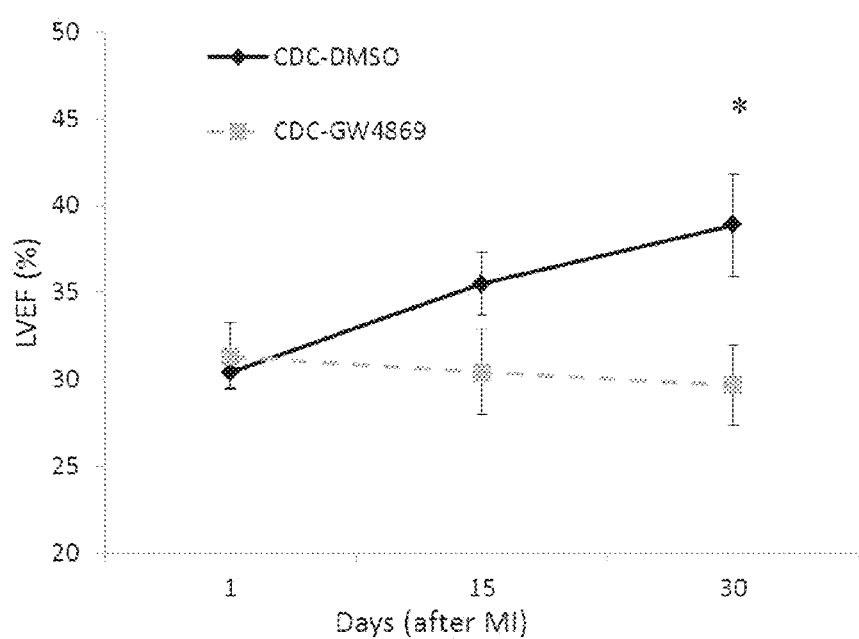
Figure 15A:
FIGS. 15A-15B depict ECHO data after administration of exosomes derived from cells treated with a neutral sphingomyelinase inhibitor (GW4869) or control cells (CDCs).
Figure 15B:

Generally speaking, exosomes are membrane bound bodies that are derived from the endocytic recycling pathway. During endocytosis, endocytic vesicles form at the plasma membrane and fuse to form early endosomes. After maturing into late endosomes, intraluminal vesicles known as multivesicular bodies (MVB) bud off into the intracytoplasmic lumen. Instead of fusing with the lysosome, however, MVB directly fuse with the plasma membrane and release exosomes into the extracellular space. In many cases, specific signaling molecules, or complexes of molecules are necessary to achieve exosomal release. Sphingomyelinases are enzymes that cleave certain lipids and may play a role in exosomal release. To investigate this, experiments were performed with an inhibitor of neutral sphingomyelinase (GW4869, Cayman Chemical). CDCs were incubated with either DMSO (control) or GW4869 and thereafter, exosomes were collected as described above. FIG. 14A shows data related to the dose-dependent reduction in exosome secretion from CDCs due to exposure of cultured CDCs to GW4869. FIG. 14B shows data that confirms that the reduction in secretion is not due to reduced CDC viability. As shown, CDCs exposed to DMSO (as a control) or GW4869 showed no significant differences in viability (based on calcein staining). To test the in vivo effects of sphingomyelinase inhibition, mice were subjected to acute myocardial infarction (as above) and treated with either exosomes derived from CDCs that were exposed to DMSO (control) or exosomes derived from CDCs that were exposed to GW4869. FIG. 14C shows that, as a result of exposure to GW4869, LVEF failed to improve, whereas, in contrast, exosomes derived from CDCs exposed to DMSO (solvent control) resulted in improvements in LVEF. These improvements in LVEF were statistically significant, even as 30 days after the MI. FIGS. 15A-15B show MM data depicting greater anatomical improvements with administration of the exosomes from DMSO exposed CDCs (15B), and lack of anatomical improvements after administration of exosomes from CDCs exposed to GW4869.

Figure 16A:
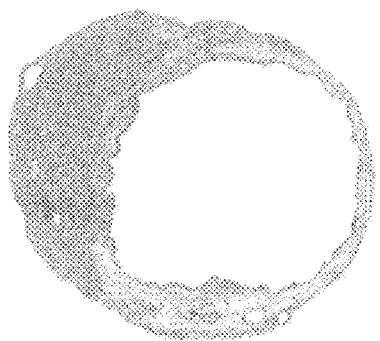
FIGS. 16A-16B depict Masson's trichrome staining of cardiac tissue treated with exosomes derived from cells treated with a neutral sphingomyelinase inhibitor (GW4869) or control cells (CDCs).
Figure 16B:
Figures 17A, 17B:
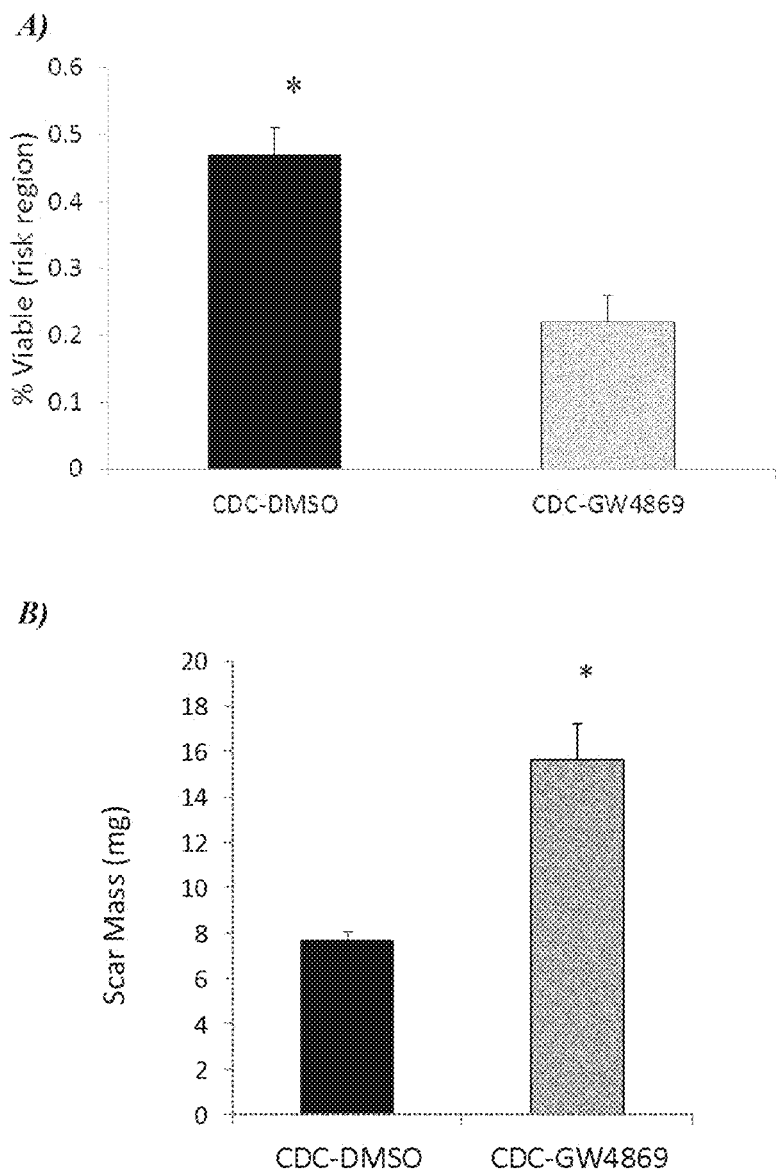
FIGS. 17A-17D depict data related to the amount of viable tissue (in the risk region, 17A), scar mass (17B), overall viable mass (17C) or infarct thickness (17D) after animals were treated with exosomes derived from cells treated with a neutral sphingomyelinase inhibitor (GW4869) or control cells (CDCs).
Figure 17C:
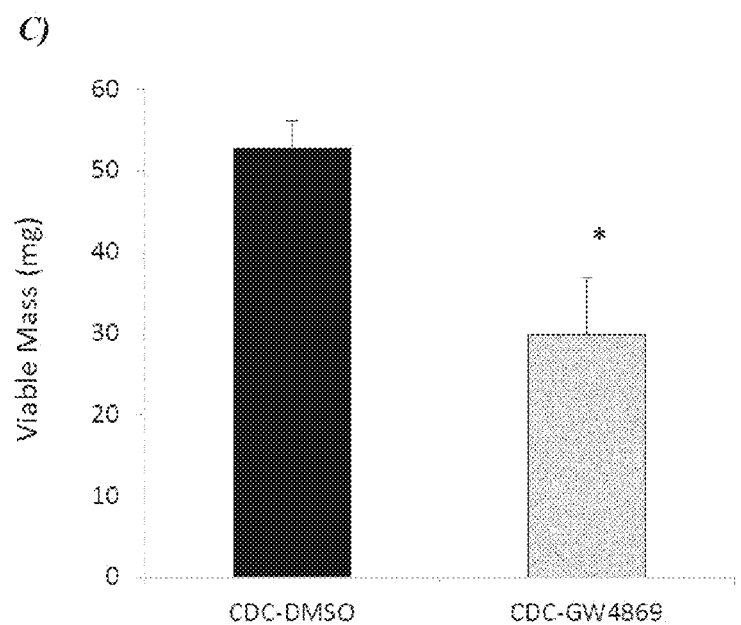
Figure 17D:
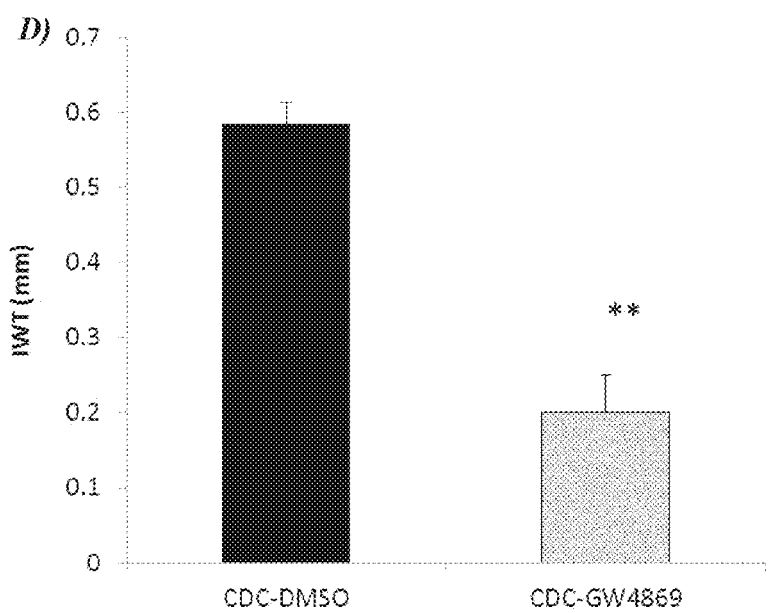

FIGS. 16A-16B further demonstrate that exosomes play a critical role in cardiac tissue repair and regeneration resulting from CDC administration. As shown in FIG. 16A, treatment of CDCs with the inhibitor of exosome secretion GW4869 and administration of the resultant exosomes results in decreased cardiac wall thickness after acute MI. In contrast, as shown in FIG. 16B, incubation of CDCs with DMSO does not adversely impact the beneficial effects of the exosomes, as demonstrated by the increased wall thickness. Additional data, shown in FIGS. 17A-17D further demonstrate inhibition of exosome release from CDCs results in reduced positive benefits (e.g., reduced cell viability in the infarct region, increased scar mass, reduced viable tissue mass, and decreased wall thickness). In several embodiments, cells that are to be used as a source of exosomes can be treated with one or more agents that prevent inhibition of exosome release and/or one or more agents that promote exosome release. Thus, in several embodiments, the eventual efficacy of cellular repair or regeneration using exosomes can be modified by particular treatments of the cells that give rise to the exosomes. In some embodiments, exosomes alone are administered to result in cellular repair regeneration, while in some embodiments, exosomes are administered in combination with the cells that give rise to those exosomes (e.g., a combination cell-exosome therapy). The latter approach, in some embodiments, potentiates the regenerative effects because the cells can continue to produce exosomes post-administration. However, in certain embodiments, neither exosomes nor cells need be administered, rather isolated products from the exosomes or the cells (e.g., nucleic acids or proteins, or combinations thereof) can be administered to yield the positive regenerative effects.

Example 6—Exosome MicroRNA Profiling and Regenerative Efficacy

Figures 8A, 8B, 8C, 8D, 8E:
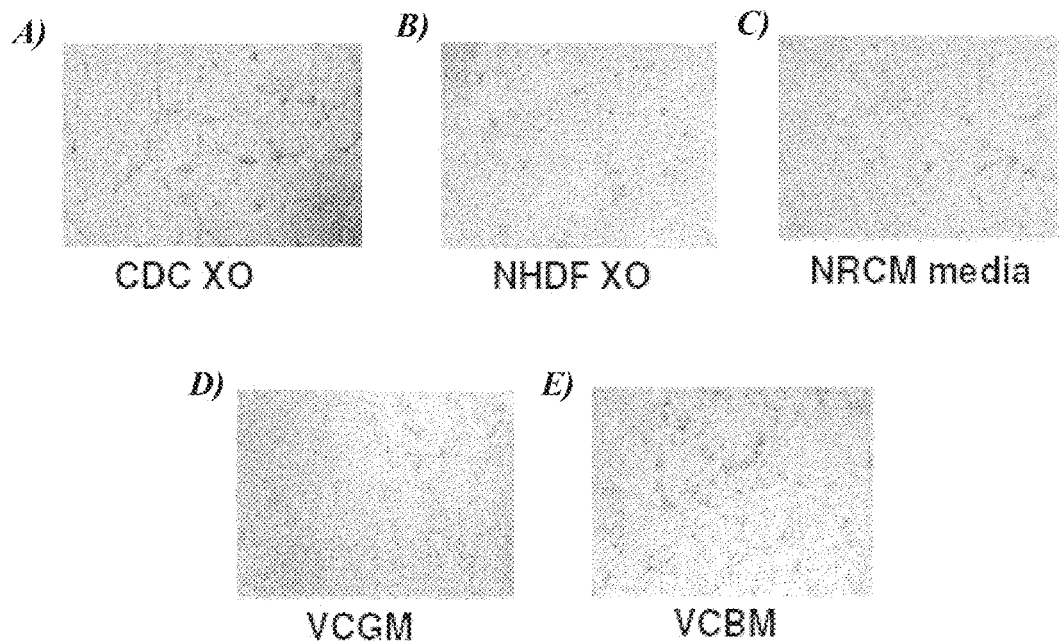
FIGS. 8A-8E depict photomicrographs of the results of an angiogenesis by tube formation assay.
Figure 18A:
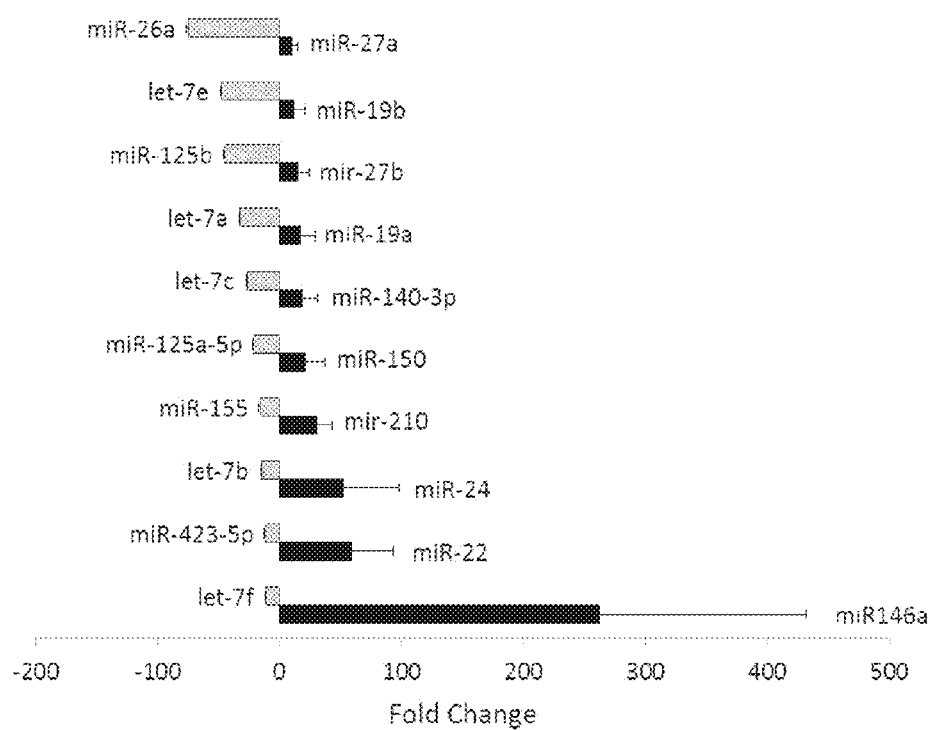

As discussed above, in some embodiments, products from exosomes (e.g., nucleic acids or proteins, or combinations thereof) can be administered in order to provide regenerative effects on damaged or diseased cells or tissues. In certain embodiments, DNA can be isolated from exosomes, while in some embodiments, RNA can be isolated from exosomes (in addition to or in place of DNA). Certain types of RNA are known to be carried by exosomes, such as, for example, microRNA (miRNA or miR). As discussed above, miRNAs function as post-transcriptional regulators, often through binding to complementary sequences on target messenger RNA transcripts (mRNAs), thereby resulting in translational repression, target mRNA degradation and/or gene silencing. In order to gain a better understanding of the miRNA contained in exosomes, an miRNA profiling experiment was performed. Exosomes were prepared as described above from both CDCs and NHDF, and total RNA was isolated from the exosomes by established methods. cDNA was generated from the total RNA and used as a template in RT PCR reactions to determine the expression levels of a panel of miRNAs. FIG. 1 8A depicts expression levels of various miRNA in CDCs as compared to NHDF cells (data are expressed as fold change relative to NHDF expression, which is the "0" value on the X-axis). As depicted, there are a variety of miRNAs that exhibit differential expression between the CDCs and the control cells. In some embodiments, miRNAs that exhibit an increase in expression over control cell are candidates for subsequent use in tissue regeneration (e.g., by administration of exosomes containing such miRNAs, or alternatively, direct administration of the miRNAs). In particular, miR146a exhibits over a 250 fold increased expression in CDCs. FIG. 18B shows a listing of those miRNA that are equivalently expressed in NHDF cells as compared to CDCs (equivalence was set for this embodiment as a less than 10-fold change in expression), those that are significantly upregulated in CDCs (right) and those that are significantly downregulated in CDCs (left). In some embodiments, however, other miRNAs exhibit altered expression, depending on the cell types tested. For example, in some embodiments, miRNAs that exhibit a decrease in expression as compared to control cells are candidates for subsequent use in tissue regeneration. Whether the miRNA expression is up or down regulated may be related to whether the miRNA is involved in a pathway in the context of subsequent suppression of translation, or alternatively, disk inhibition of translation.

Figure 19:
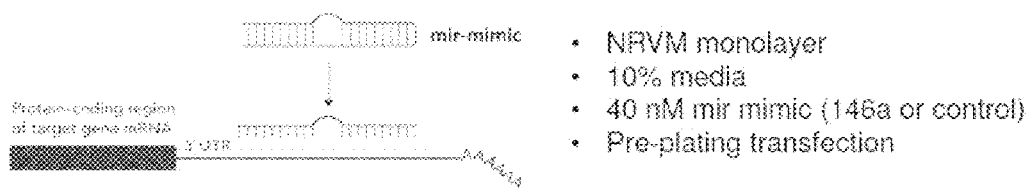
Figure 20A:
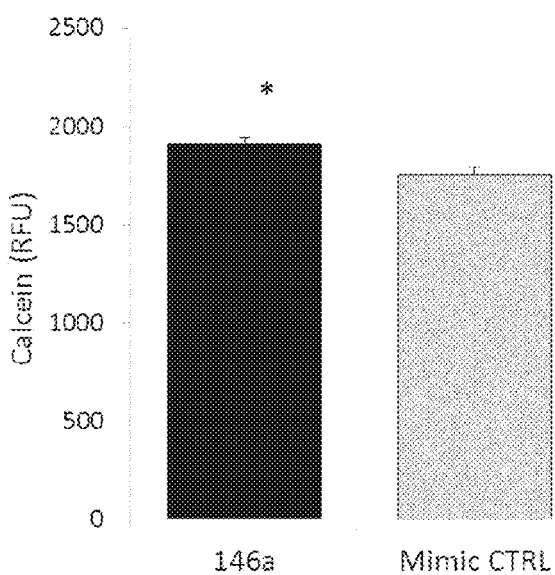
FIGS. 20A-20D depict data related to cell viability and death after cells were treated with either mi146a or a control miRNA.
Figure 20B:
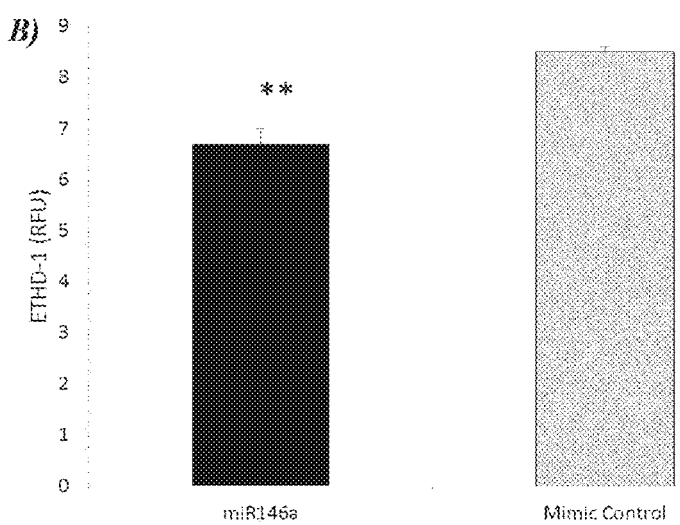
Figure 20C:
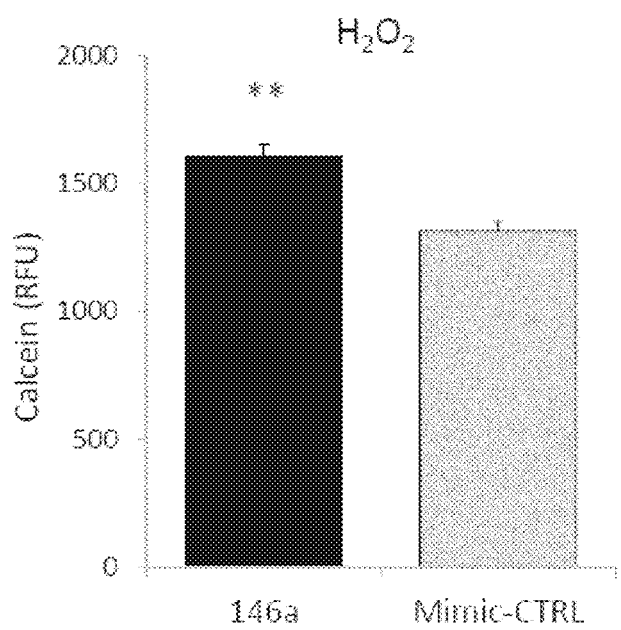
Figure 20D:
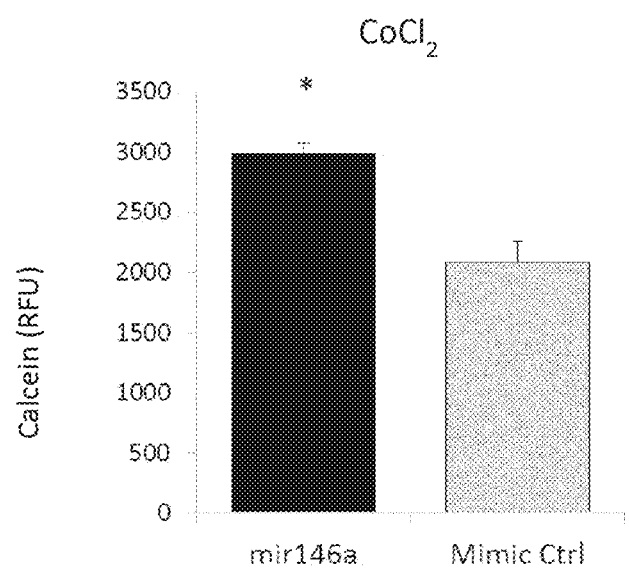

Given the large expression of mi146a, in vitro studies were performed to determine the ability of the miRNA itself to provide regenerative effects. A schematic for the experiment is shown in FIG. 19, where an miR-mimic is produced (corresponding to mi146a in size and structure, but derived from C. elegans, so it has no specificity to human mRNA) that is complementary to a protein coding region of a target gene that is important for NRVM survival. NRVM were transfected with 40 nM of either mi146a or control miRNA and grown as a monolayer (10% media). Cellular viability was assessed at 6 by calcein fluorescence and 12 hours by ETHD-1 fluorescence, respectively (FIGS. 20A and 20B, respectively). As shown in FIG. 20A, at 6 hours, cells transfected with mi146a express significantly more calcein fluorescence, which is indicative of viable cells (calcein AM, is the non-fluorescent, hydrophobic compound that easily permeates intact, live cells and hydrolysis of Calcein AM by intracellular esterases produces calcein, a hydrophilic, strongly fluorescent compound that is well-retained in the cell cytoplasm). Further, at 12 hours, cells transfected with mi146a express significantly less ETHD-1 fluorescence (20B), which also indicates enhanced cell viability (ETHD-1 produces fluorescence in damaged or dead cells). FIG. 20C shows that miR146a induces a protective effect when transfected into cells that are subsequently exposed to oxidizing conditions. Cultured NRVM that had been transfected with either miR146a or a control mimic were exposed to hydrogen peroxide to mimic oxidative conditions that result from tissue ischemia (using established protocols). Calcein staining was used to evaluate viability and these data show that the miR146a transfected NRVM show significantly greater viability than control NRVM. Similarly, when exposed to cobalt chloride (mimicking hypoxia, FIG. 20D), miR146a provides a protective effect. These data therefore indicate that mi146a alone (e.g., without the source exosome or cell) is capable of resulting in increased cell viability, despite adverse conditions that, as shown by the control data, reduce viability of untreated cells. As such, in some embodiments, cellular regeneration is accomplished through the administration of micro RNAs alone (e.g., with a suitable physiological carrier, but without exosomes or cells). In some embodiments, the administration of exosomes and/or cells can be potentiated by administration of micro RNA prior to, concurrently with, or subsequent to administration of exosomes and/or cells.

To further evaluate the regenerative capacity of miRNAs themselves, miR146a was evaluated in an in vivo MI model. According to the MI protocol above an infarction was generated in mice that had received miR146a or a mimic control. The miRNAs were delivered at a concentration of 50 nm by peri-infarct injection. Functional evaluation was performed at 15 and 30 days post-MI, and tissue regeneration was assessed at 30 days post-MI by methods discussed above. Also as discussed above, other concentrations or delivery routes of miRNAs (or exosomes and/or cells) can be used, depending on the embodiment.

Figure 21A:
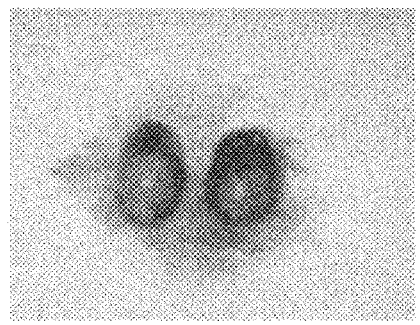
Figure 21B:
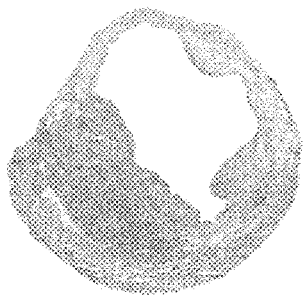
Figure 21C:
Figure 21D:
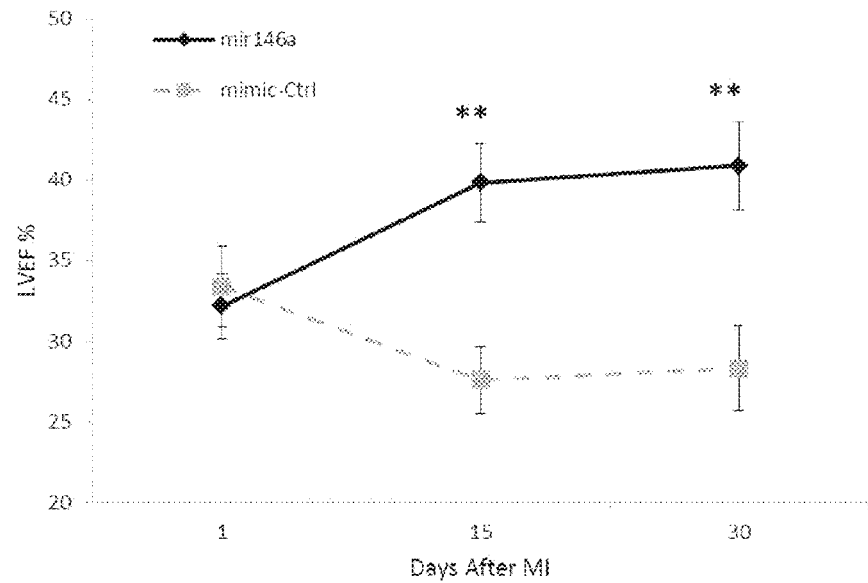
Figure 21E:
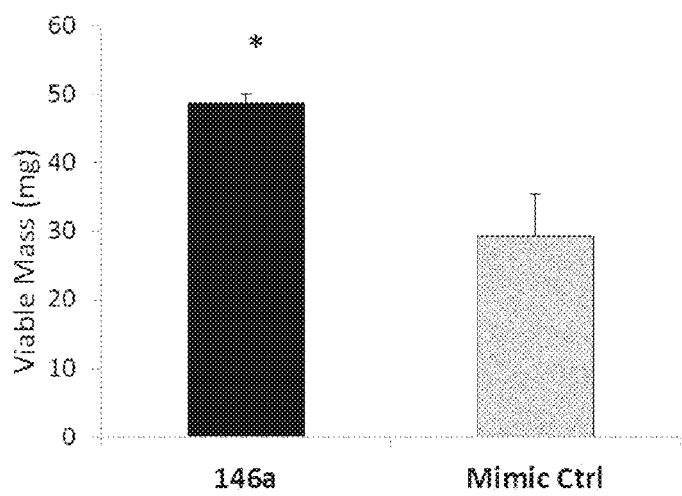
Figure 21F:
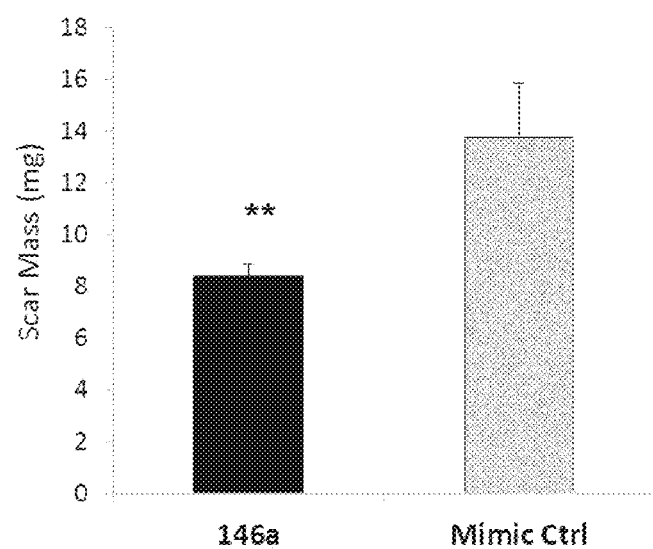
Figure 21G:
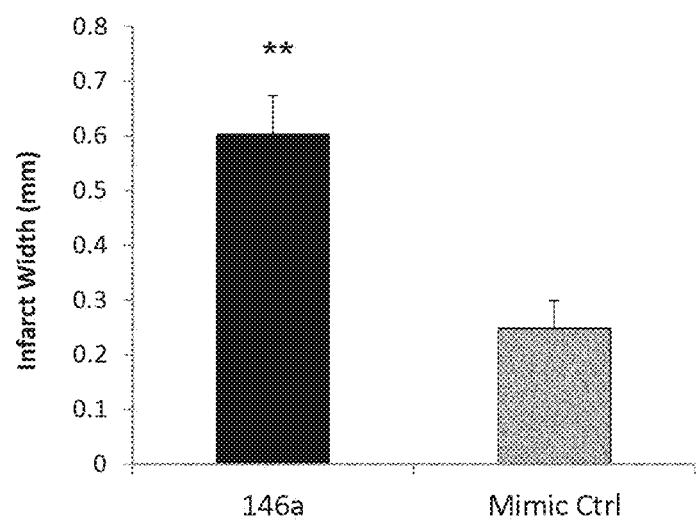

As shown in FIG. 21A, hearts from mice receiving control mimic miRNA (left heart) have a larger infarct region as grossly compared to those receiving miR146a (right heart). FIGS. 21B and 21C further corroborate that gross comparison. FIG. 21B shows Masson's Trichrome staining of an infarcted heart from a mouse that received miR mimic as a control. The wall thickness is notably thinner and has less muscle fiber than the heart shown in FIG. 21C, which is from an infarcted heart of a mouse treated with miR-146a. This histological analysis indicates that treatment with miR-146a results in reduction of collagen (e.g., scar formation) and tissue regeneration post-infarct. Not only is there an increase in tissue, that increase is also associated with an increase in cardiac function. As shown in FIG. 21D, mice that were treated with miR146a had significantly greater ejection fraction at 15 and 30 days post-MI. This increase in function, coupled with the increase in wall thickness leads, in several embodiments, to significantly improved clinical outcomes. FIGS. 21E-21G reaffirm the histological data shown in 21B and 21C. Overall viable tissue mass was significantly greater ($p<0.05$) in mice treated with miR146a (FIG. 21E). Scar mass was significantly less ($p<0.01$) in miR146a treated mice (FIG. 21F) and infarct width (e.g., wall thickness) was significantly greater in miR146a-treated mice (FIG. 21G). Taken together, these data confirm that miR146a, even if administered alone (e.g., without associated stem cells, such as CDCs, and without exosomes) are highly efficacious in repairing damaged cardiac tissue, not only anatomically by reducing scar size and increasing viable tissue, but also in terms of function. This dual impact is clinically profound, as regeneration of cardiac tissue or reduction in scar size alone, while important in development of cardiac therapy, falls short of the ultimate goal of treating a patient post-MI. Thus, in several embodiments, the administration of microRNAs, such as, for example those that are upregulated in therapeutically efficacious cells, such as CDCs, leads unexpectedly to both functional and anatomical repair of damaged cardiac tissue. In several embodiments, miR146a is particularly efficacious.

Figure 22:
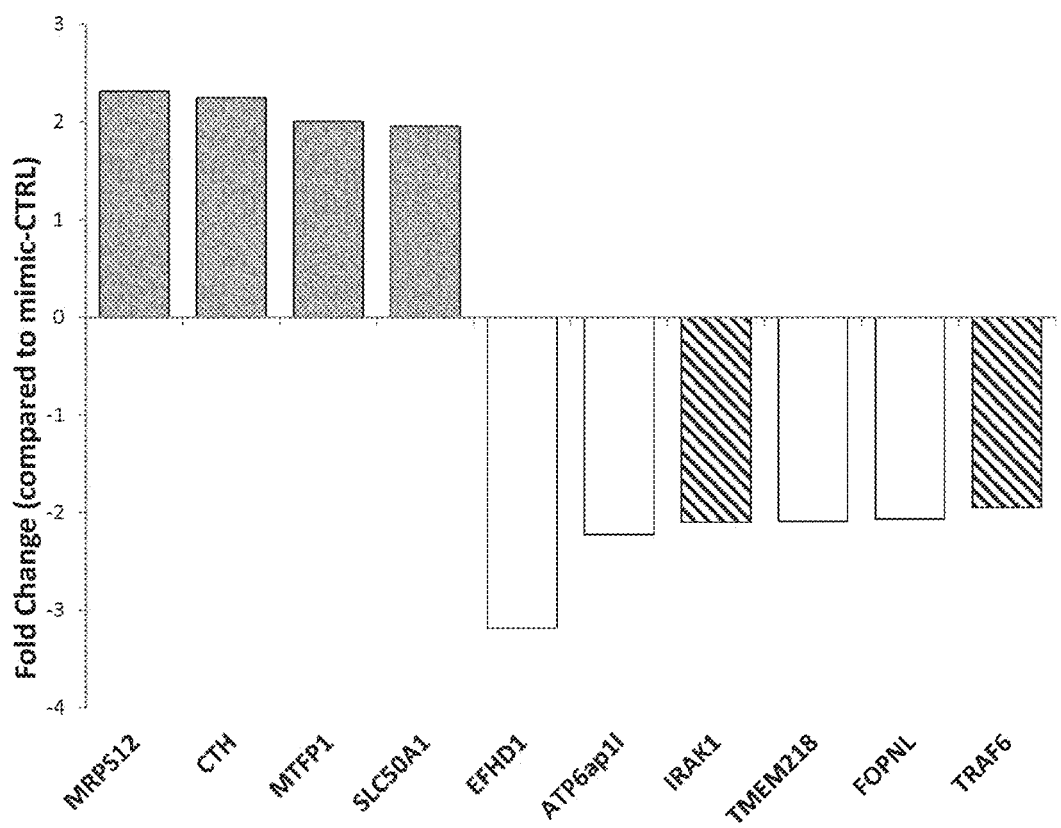

The efficacy of the miRNAs alone may be due, at least in part, various physiological mechanisms induced by the miRNA. For example, the administration of miRNA may support increased metabolic activity of cells and/or increased protein synthesis, which may enable cells to better survive adverse conditions that result from cardiac injury or disease. microRNA may also be efficacious due to the limited induction of inflammation that results from miRNA administration. FIG. 22 shows differential gene expression data that was collected after cardiomyocytes were transfected with miR146a or a mimic control in vitro. Data was collected by gene chip analysis by established methods. As shown, cardiomyocytes treated with miR146a resulted in upregulation of MRPS12 (a mitochondrial ribosomal protein), CTH (cystothionase), MTFP 1 (mitochondrial fission process protein 1), and SLC50A1 (a sugar transporter), which may be related to increased metabolic activity of the treated cardiomyoctes and/or protein synthesis. Notably, cardiomyocytes treated with miR146a show reduced levels of IRAK1 (interleukin-I receptor-associated kinase 1) and TRAF6 (a member of the TNF receptor associated factor family), both of which are established as being involved in early signaling stages of inflammatory pathways. As such, the reduction in expression of these genes (as compared to cardiomyocytes treated with control mimic miRNA) may decrease the amount and/or intensity of immune activity in the cardiomyocytes. As a result, the treated cardiomyocytes may enjoy improved viability, despite the inflammatory response that can result after cardiac injury. This improved viability may in turn, in several embodiments, be a mechanism by which miRNAs can provide positive therapeutic benefits (both anatomic and functional).

Figure 23:
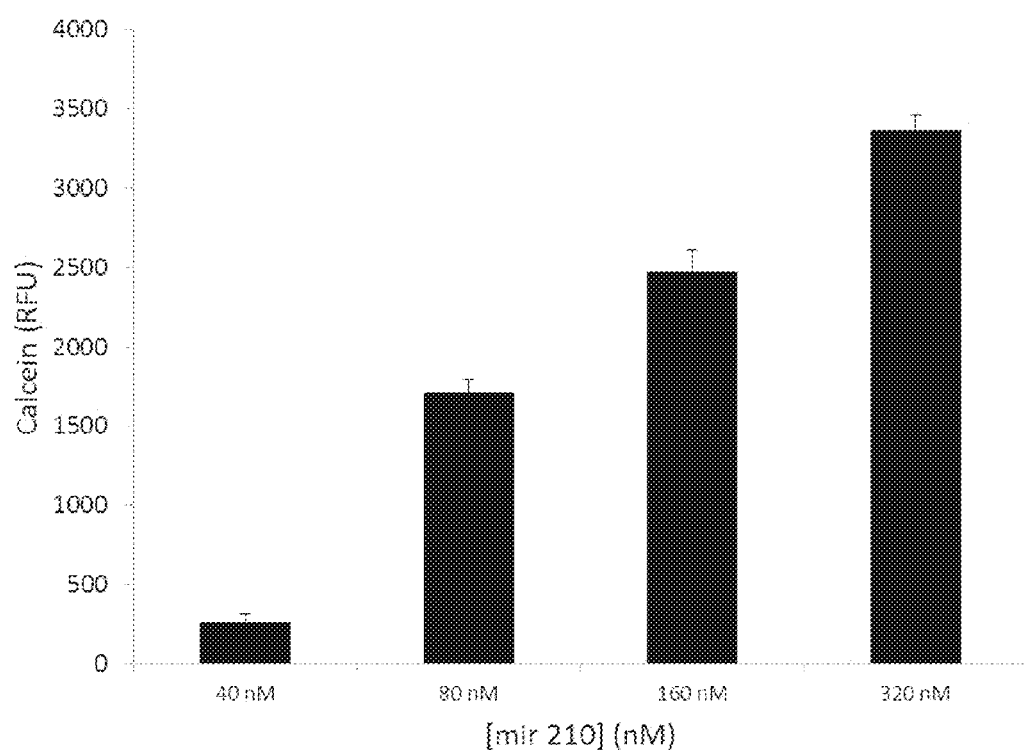
FIG. 23 shows data related to cell viability of cultured cardiomyocytes transfected with miR210 after exposure to hydrogen peroxide.

Other miRNAs that are upregulated also, in several embodiments, can be used to effect positive therapeutic outcomes. For example, miR210, which is upregulated in CDCs approximately 30-fold (as compared to NHDF), improved cardiomyocyte viability in a dose-response fashion, when cardiomyocytes were exposed to $H_2O_2$. FIG. 23 shows this data. Increasing the amount of miR210 transfected from 40 nM up to 320 nM resulted in greater than a 10-fold increase in cardiomyocyte viability (based on calcein fluorescence). Accordingly, the improved ability of cells such as cardiomyocytes to survive adverse conditions after being contacted with selected miRNAs supports the use, according to several embodiments disclosed herein, of miRNAs alone to treat cardiac tissue damage. In several embodiments, the administration of miRNAs in a therapeutic context comprises delivery of the miRNAs directly to a target cell (such as a cardiomyocyte). In several embodiments, that delivery is accomplished by administering the miRNA in a vehicle that enables the miRNA to contact and/or enter the target cell. This may include, depending on the embodiment, a lipid-based transfection agent, a viral agent (e.g., adenovirus, adeno-associated virus, lentivirus, etc.) or particle based agents (e.g., gene guns). The miRNA can be delivered, in several embodiments, in concentrations ranging from about 10 nM to about 10 including about 10 nM to about 20 nM, about 20 nM to about 30 nM, about 30 nM to about 40 nM, about 40 nM to about 50 nM, about 50 nM to about 60 nM, about 60 nM to about 70 nM, about 70 nM to about 80 nM, about 80 nM to about 90 nM, about 90 nM to about 100 nM, about 100 nM to about 150 nM, about 150 nM to about 200 nM, about 200 nM to about 400 nM, about 400 nM to about 800 nM, about 800 nM to about 1 about 1 µM to about 2 about 2 µM to about 4 about 4 µM to about 6 about 6 µM to about 8 about 8 µM to about 10 and any concentration between these ranges.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering exosomes" include "instructing the administration of exosomes." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

What is claimed is:

1. A preparation of exosomes harvested from cardiospheres or cardiosphere-derived cells (CDCs).
2. The preparation of claim 1, wherein the preparation comprises exosomes having a diameter from about 15 nm to about 205 nm.
3. The preparation of claim 1, wherein the preparation comprises exosomes having a diameter from about 20 nm to about 90 nm.
4. The preparation of claim 1, wherein the preparation comprises exosomes having a diameter from about 15 nm to about 95 nm.
5. The preparation of claim 1, wherein said exosomes comprise miR-146a.
6. The preparation of claim 5, wherein said exosomes further comprise miR-210.
7. The preparation of claim 6, wherein said exosomes further comprise one or more additional miRNAs selected from the group consisting of miR-26a, miR27-a, let-7e, miR-19b, miR-125b, miR-27b, let-7a, miR-19a, let-7c, miR-140-3p, miR-125a-5p, miR-150, miR-155, mir-210, let-7b, miR-24, miR-423-5p, miR-22, let-7f, miR-146a, and combinations thereof.
8. A preparation of exosomes harvested from cardiosphere-derived cells (CDCs).
9. The preparation of claim 8, wherein the preparation comprises exosomes having a diameter from about 15 nm to about 205 nm.
10. The preparation of claim 8, wherein the preparation comprises exosomes having a diameter from about 20 nm to about 90 nm.
11. The preparation of claim 8, wherein the preparation comprises exosomes having a diameter from about 15 nm to about 95 nm.
12. The preparation of claim 8, wherein said exosomes comprise miR-146a.
13. The preparation of claim 12, wherein said exosomes further comprise miR-210.
14. The preparation of claim 13, wherein said exosomes further comprise one or more additional miRNAs selected from the group consisting of miR-26a, miR27-a, let-7e, miR-19b, miR-125b, miR-27b, let-7a, miR-19a, let-7c, miR-140-3p, miR-125a-5p, miR-150, miR-155, mir-210, let-7b, miR-24, miR-423-5p, miR-22, let-7f, miR-146a, and combinations thereof.

* * * * *